United States Patent
Cho et al.

(10) Patent No.: US 8,501,714 B2
(45) Date of Patent: Aug. 6, 2013

(54) **INHIBITORS OF *FLAVIVIRIDAE* VIRUSES**

(75) Inventors: Aesop Cho, Mountain View, CA (US);
Lee S. Chong, Newark, CA (US);
Michael O'Neil Hanrahan Clarke, Redwood City, CA (US); Edward Doerffler, Union City, CA (US);
Choung U. Kim, San Carlos, CA (US);
Qi Liu, San Mateo, CA (US); William J. Watkins, Saratoga, CA (US); Jennifer R. Zhang, Foster City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 13/392,467

(22) PCT Filed: Sep. 7, 2010

(86) PCT No.: PCT/US2010/047983
§ 371 (c)(1),
(2), (4) Date: Mar. 13, 2012

(87) PCT Pub. No.: WO2011/031669
PCT Pub. Date: Mar. 17, 2011

(65) Prior Publication Data
US 2012/0156166 A1    Jun. 21, 2012

Related U.S. Application Data

(60) Provisional application No. 61/240,874, filed on Sep. 9, 2009.

(51) Int. Cl.
*A61K 31/67* (2006.01)
*A61K 31/675* (2006.01)
*C07F 9/6558* (2006.01)
*C07F 9/6553* (2006.01)

(52) U.S. Cl.
USPC ............... 514/81; 514/89; 514/92; 514/95; 544/244; 546/22; 548/119; 549/6

(58) Field of Classification Search
USPC . 424/85.4; 549/6; 548/119; 544/244; 546/22; 514/95, 92, 81, 89, 43
See application file for complete search history.

(56) References Cited

U.S. PATENT DOCUMENTS

| | | | |
|---|---|---|---|
| 5,861,421 | A | 1/1999 | Christensen, IV et al. |
| 6,881,741 | B2 | 4/2005 | Kong et al. |
| 6,887,877 | B2 | 5/2005 | Kong et al. |
| 7,402,608 | B2 | 7/2008 | Kong et al. |
| 7,521,473 | B2 | 4/2009 | Lee et al. |
| 7,569,600 | B2 | 8/2009 | Denis et al. |
| 2002/0002199 | A1 | 1/2002 | Jeppesen et al. |
| 2003/0229053 | A1 | 12/2003 | Kong et al. |
| 2004/0116509 | A1 | 6/2004 | Kong et al. |
| 2005/0119332 | A1 | 6/2005 | Jeppesen et al. |
| 2006/0142347 | A1 | 6/2006 | Kong et al. |
| 2006/0276533 | A1 | 12/2006 | Denis et al. |
| 2007/0099929 | A1 | 5/2007 | Thede et al. |
| 2008/0299080 | A1 | 12/2008 | Kong et al. |
| 2009/0274655 | A1 | 11/2009 | Grimes et al. |
| 2011/0020278 | A1 | 1/2011 | Canales et al. |
| 2011/0178058 | A1 | 7/2011 | Canales et al. |
| 2011/0178129 | A1 | 7/2011 | Canales et al. |

FOREIGN PATENT DOCUMENTS

| | | |
|---|---|---|
| WO | WO-2002/100846 | 12/2002 |
| WO | WO-2002/100851 | 12/2002 |
| WO | WO 2004052885 A1 * | 6/2004 |
| WO | WO-2005/095386 | 10/2005 |
| WO | WO-2006/072347 | 7/2006 |
| WO | WO-2006/072348 | 7/2006 |
| WO | WO-2007/093365 | 8/2007 |
| WO | WO-2008/058393 | 5/2008 |
| WO | WO-2010/065668 | 6/2010 |
| WO | WO-2011/011303 | 1/2011 |
| WO | WO-2011/068715 | 6/2011 |
| WO | WO-2011/088345 | 7/2011 |
| WO | WO-2012/006055 | 1/2012 |

OTHER PUBLICATIONS

U.S. Appl. No. 13/549,130, filed Jul. 13, 2012, Watkins et al.
International Search Report and Written Opinion for Application No. PCT/US2011/021279, mailed May 2, 2011.
International Search Report and Written Opinion for Application No. PCT/US2011/021335, mailed Feb. 22, 2011.
International Search Report and Written Opinion for Application No. PCT/US2010/042394, mailed Sep. 29, 2010.
Office Action for U.S. Appl. No. 12/838,684, mailed Aug. 2, 2012.
Notice of Allowance for U.S. Appl. No. 13/006,761, mailed Oct. 3, 2012.
Office Action for U.S. Appl. No. 13/007,150, mailed Oct. 3, 2012.
Boyer, N, et al. (2000) "Pathogenesis, diagnosis and management of hepatitis C," *Journal of Hepatology* 32 (suppl 1):98-112.

(Continued)

*Primary Examiner* — Kristin Bianchi
(74) *Attorney, Agent, or Firm* — Kilpatrick Townsend & Stockton LLP

(57) ABSTRACT

Provided are compounds of Formula I: and pharmaceutically acceptable salts and esters thereof. The compounds, compositions, and methods provided are useful for the treatment of Flaviviridae virus infections, particularly hepatitis C infections.

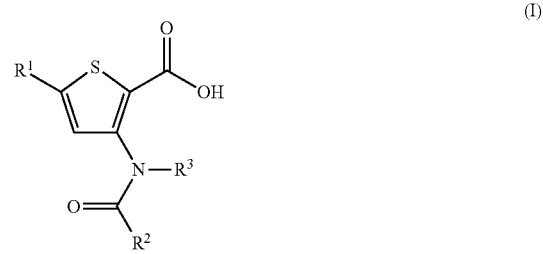

(I)

28 Claims, No Drawings

OTHER PUBLICATIONS

Calisher, C. et al. (1989) "Antigenic Relationships between Flaviviruses as Determined by Cross-neutralization Tests with Polyclonal Antisera," *J.gen. Virol.* 70:37-43.

Di Besceglie, A. et al. (1999) "Some 1.8 percent of the U.S. adult population are infected with the hepatitis C virus, most without knowing it" *Scientific American* Oct. pp. 80-85.

Domingo, E. et al. (1985) "The quasispecies (extremely heterogeneous) nature of viral RNA genome populations: biological relevance—a review" *Gene* 40:1-8.

Dymock, B. et al. (2000) "Novel approaches to the treatment of hepatitis C virus infection," *Antiviral Chemistry & Chemotherapy* 11(2):79-86.

Fukumoto, T. et al. (1996) "Viral Dynamics of Hepatitis C Early After Orthotopic Liver Transplantation: Evidence for Rapid Turnover of Serum Virions," *Hepatolgy* 24:1351-1354.

Gordon, C. et al. (2005) "Control of Hepatitis C: A Medicinal Chemistry Perspective," *Journal of Medicinal Chemistry* 48(1):1-20.

Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.

Maradpour, D. et al. (2007) "Replication of Hepatitis C Virus," *Nature Reviews/Microbiolory* 596):453-463.

Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.

Moennig, V. et al. (1992) "The Pestiviruses," *Advances in Virus Research* 41:53-98.

Neumann, A. (1998) "Hepatitis C Viral Dynamics in Vivo and the Antiviral Efficacy of Interferon-$\alpha$ Therapy," *Science* 282:103-107.

Schul, W. (2007) " A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-$\alpha$-2b Plus Ribavirin," *Drugs* 62:507-556.

U.S. Appl. No. 13/801,011, filed Mar. 13, 2013, Watkins et al.

U.S. Appl. No. 13/801,039, filed Mar. 13, 2013, Evans et al.

U.S. Appl. No. 13/800,991, filed Mar. 13, 2013, Hashash et al.

International Search Report and Written Opinion for PCT/US2010/047983 mailed Nov. 15, 2010.

International Search Report and Written Opinion for PCT/US2012/046741 mailed Aug. 22, 2012.

Office Communications for U.S. Appl. No. 12/838,684.

Office Communications for U.S. Appl. No. 13/006,761.

Office Communications for U.S. Appl. No. 13/007,150.

\* cited by examiner

INHIBITORS OF *FLAVIVIRIDAE* VIRUSES

FIELD OF THE INVENTION

The present application includes novel inhibitors of Flaviviridae viruses, compositions containing such compounds, therapeutic methods that include the administration of such compounds.

BACKGROUND OF THE INVENTION

Viruses comprising the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, Oct.: 80-85, (1999); Gordon, C. P., et al., *J. Med. Chem.* 2005, 48, 1-20; Maradpour, D., et al., *Nat. Rev. Micro.* 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., *Science* 1998, 282, 103-7; Fukimoto, et al., *Hepatology*, 1996, 24, 1351-4; Domingo, et al., *Gene*, 1985, 40, 1-8; Martell, et al., *J. Viral.* 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit.

Combined, infections from the Flaviviridae virus family cause significant mortality, morbidity and economic losses throughout the world. Alkynyl substituted thiophenes with anti-Flaviviridae virus activity have been disclosed by Chan, et al., WO 2008058393; Wunberg, et al., WO 2006072347; and Chan, et al., WO 2002100851; but none of these are currently clinically approved antiviral therapeutics. Therefore, there remains a need to develop effective treatments for Flaviviridae virus infections.

SUMMARY OF THE INVENTION

In one aspect, provided is a compound of Formula I:

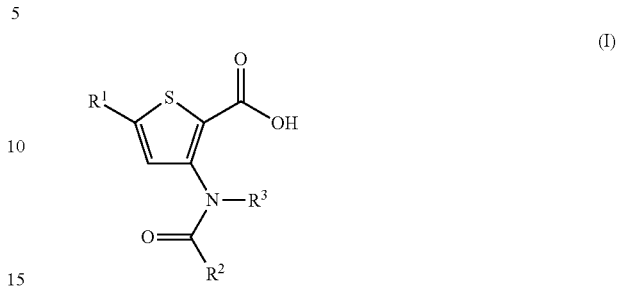

or a pharmaceutically acceptable salt or ester thereof, wherein;

$R^1$ is -$(L^1)_m$-$(L^2)_n$-$X^1$;

$L^1$ is selected from the group consisting of alkynylene and optionally substituted arylene;

m is 1;

when $L^1$ is substituted, $L^1$ is substituted with one or more $Q^6$;

$L^2$ is selected from the group consisting of —NHC(O)— and optionally substituted alkylene;

n is 0 or 1;

when $L^2$ is substituted, $L^2$ is substituted with one or more $Q^6$;

$X^1$ is selected from the group consisting of
a) —P(O)$R^xR^y$,
b) —P(O)OR$^x$R$^y$,
c) —OP(O)R$^x$R$^y$ and
d) optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

each of $R^x$ and $R^y$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^x$ and $R^y$ taken together with the atoms to which they are attached form a 3 to 10 membered heterocyclyl;

when either $R^x$ or $R^y$ is substituted, $R^x$ or $R^y$ is substituted with one or more $Q^6$;

when $X^1$ is selected from d) and is substituted, $X^1$ is substituted with one or more $Q^1$;

each $Q^1$ individually is selected from the group consisting of halogen, oxo, oxide, —NO$_2$, —SR$^{11}$, —S(O)R$^{10}$, —S(O)$_2$R$^{10}$, —S(O)$_2$NR$^{12}$R$^{11}$, —NR$^{12}$C(O)R$^{11}$, —NR$^{12}$C(O)NR$^{11}$R$^{12}$, —NR$^{11}$S(O)R$^{10}$, —NR$^{11}$S(O)$_2$R$^{10}$, —NR$^{12}$S(O)$_2$NR$^{11}$R$^{12}$, —CR$^{12}$(=NNR$^{11}$R$^{12}$), —CR$^{12}$(=NOR$^{11}$), —ONR$^{12}$R$^{11}$, —ON(=CR$^{12}$R$^{11}$), —NR$^{12}$OR$^{11}$, —OH, —NR$^{11}$R$^{12}$, —C(O)OR$^{12}$, —CN, —N$_3$, —C(=NR$^{13}$)NR$^{11}$R$^{12}$, —NR$^{12}$C(=NR$^{13}$)NR$^{11}$R$^{12}$, —NR$^{12}$C(O)OR$^{11}$, —OC(O)NR$^{11}$R$^{12}$, —OP(O)R$^{11}$R$^{12}$, —P(O)R$^{11}$R$^{12}$, —P(O)OR$^{11}$R$^{12}$, —C(O)NR$^{11}$R$^{12}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(±)-3-14 membered heteroaryl, optionally substituted —C(O)$C_{6-12}$ arylalkyl and optionally substituted-3-10 membered heterocyclyl;

wherein each $R^{10}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{11}$ and $R^{12}$, independently, is selected from the group consisting of H, optionally substituted $C_{1-12}$ alkyl, optionally substituted $O_{2-12}$ alkenyl, optionally substituted $O_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{11}$ and $R^{12}$ taken together with the atoms to which they are attached form a 4 to 10 membered heterocyclyl;

or $R^{10}$ and $R^{11}$ taken together with the atoms to which they are attached form a 4 to 10 membered heterocyclyl;

each $R^{13}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{8-18}$ arylalkyl, —CN, —C(O)$R^{14}$, —CHO and —S(O)$_2R^{14}$;

where each $R^{14}$ individually is optionally substituted $C_{1-12}$ alkyl;

when $Q^1$ is substituted, $Q^1$ is substituted with one or more $Q^6$;

$R^2$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein, when $R^2$ is substituted, $R^2$ is substituted with one or more $Q^2$;

where each $Q^2$ individually is selected from the group consisting of halogen, oxo, oxide, —NO$_2$, —SR$^{21}$, —S(O)R$^{20}$, —S(O)$_2$R$^{20}$, —S(O)$_2$NR$^{22}$R$^{21}$, —NR$^{22}$C(O)R$^{21}$, —NR$^{22}$C(O)NR$^{21}$R$^{22}$, —NR$^{21}$S(O)R$^{20}$, —NR$^{21}$S(O)$_2$R$^{20}$, —NR$^{22}$S(O)$_2$NR$^{21}$R$^{22}$, —CR$^{22}$(=NNR$^{21}$R$^{22}$), —CR$^{22}$(=NOR$^{21}$), —ONR$^{22}$R$^{21}$, —ON(=CR$^{22}$R$^{21}$), —NR$^{22}$OR$^{21}$, —OH, —NR$^{21}$R$^{22}$, —C(O)OR$^{22}$, —CN, —N$_3$, —C(=NR$^{23}$)N R$^{21}$R$^{22}$, —NR$^{22}$C(=NR$^{23}$)N R$^{21}$R$^{22}$, —NR$^{22}$C(O)OR$^{21}$, and —OC(O)NR$^{21}$R$^{22}$, —OP(O)R$^{21}$R$^{22}$, —P(O)R$^{21}$R$^{22}$, —P(O)OR$^{21}$R$^{22}$, —C(O)NR$^{21}$R$^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-8}$ cycloalkyl, optionally substituted —C(O)$C_{6-12}$ aryl, optionally substituted —C(±)-3-14 membered heteroaryl, optionally substituted —C(O)$C_{6-12}$ arylalkyl and optionally substituted 3-10 membered heterocyclyl;

wherein each $R^{20}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{21}$ and $R^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{21}$ and $R^{22}$ taken together with the atoms to which they are attached form a 4 to 10 membered heterocyclyl;

or $R^{20}$ and $R^{21}$ taken together with the atoms to which they are attached form a 4 to 10 membered heterocyclyl;

each $R^{23}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{24}$, CHO and —S(O)$_2$R$^{24}$;

where each $R^{24}$ individually is optionally substituted $C_{1-12}$ alkyl;

when $Q^2$ is substituted, $Q^2$ is substituted with one or more $Q^6$;

$R^3$ is -(L$^3$)$_p$-(L$^4$)$_q$-(X$^3$);

L$^3$ is selected from the group consisting of optionally substituted $C_{1-12}$ alkylene, optionally substituted $C_{2-12}$ alkenylene, optionally substituted $C_{2-12}$ alkynylene, optionally substituted $C_{3-12}$ cycloalkylene, optionally substituted $C_{1-12}$ haloalkylene, optionally substituted $C_{6-14}$ arylene, optionally substituted 3-12 membered heterocyclylene, optionally substituted 3-18 membered heteroarylalkylene and optionally substituted $C_{6-18}$ arylalkylene;

p is 0 or 1;

when L$^3$ is substituted, L$^3$ is substituted with one or more $Q^3$, each $Q^3$ individually is selected from the group consisting of halogen, oxo, oxide, —NO$_2$, —SR$^{31}$, —S(O)R$^{30}$, —S(O)$_2$R$^{30}$, —S(O)$_2$NR$^{32}$R$^{31}$, —NR$^{32}$C(O)R$^{31}$, —NR$^{32}$C(O)NR$^{31}$R$^{32}$, —NR$^{31}$S(O)R$^{30}$, —NR$^{31}$S(O)$_2$R$^{30}$, —NR$^{32}$S(O)$_2$NR$^{31}$R$^{32}$, —CR$^{32}$(=NNR$^{31}$R$^{32}$), —CR$^{32}$(=NOR$^{31}$), —ONR$^{32}$R$^{31}$, —ON(=CR$^{32}$R$^{31}$), —NR$^{32}$OR$^{31}$, —OH, —NR³¹R³², —C(O)OR³², —CN, —N₃, —C(=NR³³)NR³¹R³², —NR³⁰C(=NR³³)N R³¹R³², —NR³⁰C(O)OR³¹, and —OC(O)NR³¹R³², —OP(O)R³¹R³², —P(O)R³¹R³², —P(O)OR³¹R³², —C(O)NR³¹R³², optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl and optionally substituted 3-10 membered heterocyclyl;

wherein each R³⁰, independently, is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl and optionally substituted O$_{6-18}$ arylalkyl;

wherein each R³¹ and R³², independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{e-14}$ aryl, optionally substituted 3-14 membered heteroaryl, optionally substituted 3-12 membered heterocyclyl, optionally substituted 3-18 membered heteroarylalkyl and optionally substituted C$_{6-18}$ arylalkyl;

or R³¹ and R³² taken together with the atoms to which they are attached form a 4 to 10 membered heterocyclyl;

or R³⁰ and R³¹ taken together with the atoms to which they are attached form a 4 to 10 membered heterocyclyl;

each R³³ independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ aryfalkyl, —CN, —C(O)R³⁴, CHO and —S(O)₂R³⁴;

where each R³⁴ individually is optionally substituted C$_{1-12}$ alkyl;

when Q³ is substituted, Q³ is substituted with one or more Q⁶;

L⁴ is selected from the group consisting of —NH— and optionally substituted C$_{1-12}$ alkylene;

q is 0, 1 or 2;

when L⁴ is substituted, L⁴ is substituted with one or more Q⁶;

X³ is selected from the group consisting of:

e) —P(O)R$^x$R$^y$, f) —P(O)OR$^x$R$^y$, g) —OP(O)R$^x$R$^y$, h) —P(O)(OR$^x$)(OR$^y$), i)

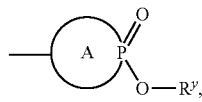

wherein each A is a 4 to 6 membered ring, including the depicted P atom, j)

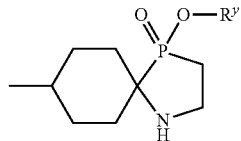

and k) optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl and optionally substituted C$_{6-18}$ arylalkyl;

each of R$^x$ and R$^y$ individually is as defined above;

when X³ is selected from k) and is substituted, X³ is substituted with one or more Q⁴;

each Q⁴ individually is selected from the group consisting of halogen, oxo, oxide, —NO₂, —SR⁴¹, —S(O)R⁴⁰, —S(O)₂R⁴⁰, —S(O)₂NR⁴²R⁴¹, S(O)₂NR⁴²R⁴¹, —NR⁴²C(O)R⁴¹, —NR⁴²C(O)NR⁴¹R⁴², —NR⁴¹S(O)R⁴⁰, —NR⁴¹S(O)₂R⁴⁰, —NR⁴²S(O)₂NR⁴¹R⁴², —CR⁴²(=NNR⁴¹R⁴²), —CR⁴² (=NOR⁴¹), —ONR⁴²R⁴¹, —ON(=CR⁴²R⁴¹), —NR⁴²OR⁴¹, —OH, —NR⁴¹R⁴², —C(O)OR⁴², —CN, —N₃, —C(=NR⁴³)NR⁴¹R⁴², —NR⁴²C(=NR⁴³)NR⁴¹R⁴², —NR⁴²C(O)OR⁴¹, and —OC(O)NR⁴¹R⁴², —OP(O)R⁴¹R⁴², —P(O)R⁴¹R⁴², —P(O)OR⁴¹R⁴², —C(O)NR⁴¹R⁴², optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O) C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(±)-3-14 membered heteroaryl, optionally substituted —C(O)C$_{6-12}$ arylalkyl and optionally substituted-3-10 membered heterocyclyl;

wherein each R⁴⁰, independently, is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl and optionally substituted C$_{6-18}$ arylalkyl;

wherein each R⁴¹ and R⁴², independently, is selected from the group consisting of H, optionally substituted C$_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{41}$ and $R^{42}$ taken together with the atoms to which they are attached form a 4 to 10 membered heterocyclyl;

or $R^{40}$ and $R^{41}$ taken together with the atoms to which they are attached form a 4 to 10 membered heterocyclyl;

each $R^{43}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-16}$ arylalkyl, —CN, —C(O)$R^{44}$, CHO and —S(O)$_2R^{44}$;

where each $R^{44}$ individually is optionally substituted $C_{1-12}$ alkyl;

when $Q^4$ is substituted, $Q^4$ is substituted with one or more $Q^6$; and each $Q^6$ individually is selected from the group consisting of halogen, oxo, oxide, —NO$_2$, —N(=O), —SR$^{61}$, —S(O)R$^{60}$, —S(O)$_2R^{60}$, —S(O)$_2NR^{62}R^{61}$, —NR$^{62}$C(O)R$^{61}$, —NR$^{62}$C(O)NR$^{61}R^{62}$, —NR$^{61}$S(O)R$^{60}$, —NR$^{61}$S(O)$_2R^{60}$, —NR$^{62}$S(O)$_2NR^{61}R^{62}$, —CR$^{62}$(=NNR$^{61}R^{62}$), —CR$^{62}$(=NOR$^{61}$), —ONR$^{62}R^{61}$, —ON(=CR$^{62}R^{61}$), —NR$^{62}$OR$^{61}$, —OH, —NR$^{61}R^{62}$, C(O)OR$^{62}$, —CN, —N$_3$, —C(=NR$^{63}$)N R$^{61}R^{62}$, —NR$^{62}$C(=NR$^{63}$)N R$^{61}R^{62}$, —NR$^{62}$C(O)OR$^{61}$, and —OC(O)NR$^{61}R^{62}$, —OP(O)R$^{61}R^{62}$, P(O)R$^{61}R^{62}$, —P(O)OR$^{61}R^{62}$, —P(O)(OR$^{61}$)OR$^{62}$, —C(O)NR$^{61}R^{62}$, $C_{1-6}$ alkyl, $C_{2-6}$ alkenyl, $C_{2-6}$ alkynyl, $C_{3-6}$ cycloalkyl, $C_{6-12}$ arylalkyl, $C_{6-12}$ aryl, 3-14 membered heteroaryl, $C_{1-6}$ alkyloxy, $C_{2-6}$ alkenyloxy, $C_{2-6}$ alkynyloxy, $C_{3-6}$ cycloalkyloxy, $C_{6-12}$ aryloxy, 3-14 membered heteroaryloxy, 4-12 membered heterocyclyloxy, —C(O)$C_{1-6}$ alkyl, —C(O)$C_{2-6}$ alkenyl, —C(O)$C_{2-6}$ alkynyl, —C(O)$C_{3-6}$ cycloalkyl, —C(O)$C_{1-6}$ haloalkyl, —C(O)$C_{6-12}$ aryl, —C(O)— 3-14 membered heteroaryl, —C(O)$C_{6-12}$ arylalkyl and 3-10 membered heterocyclyl;

wherein each $R^{60}$, independently, is selected from the group consisting of $C_{1-12}$ alkyl, $O_{2-12}$ alkenyl, $C_{2-12}$ alkynyl, $C_{3-12}$ cycloalkyl, $C_{1-12}$ haloalkyl, $C_{6-14}$ aryl, 3-14 membered heteroaryl, 3-12 membered heterocyclyl, 3-18 membered heteroarylalkyl and $C_{6-18}$ arylalkyl;

wherein each $R^{61}$ and $R^{62}$, independently, is selected from the group consisting of H, $C_{1-12}$ alkyl, $C_{2-12}$ alkenyl, $C_{2-12}$ alkynyl, $C_{3-12}$ cycloalkyl, $C_{1-12}$ haloalkyl, $C_{6-14}$ aryl, 3-14 membered heteroaryl, 3-12 membered heterocyclyl, 3-18 membered heteroarylalkyl and $C_{6-18}$ arylalkyl;

or $R^{61}$ and $R^{62}$ taken together with the atoms to which they are attached form a 4 to 10 membered heterocyclyl;

or $R^{60}$ and $R^{61}$ taken together with the atoms to which they are attached form a 4 to 10 membered heterocyclyl;

each $R^{63}$ independently is selected from the group consisting of H, $C_{1-12}$ alkyl, $C_{2-12}$ alkenyl, $C_{2-12}$ alkynyl, $C_{3-12}$ cycloalkyl, $C_{6-14}$ aryl, 3-14 membered heteroaryl, 3-12 membered heterocyclyl, 3-18 membered heteroarylalkyl, $C_{6-18}$ arylalkyl, —CN, —C(O)$R^{64}$, —CHO and —S(O)$_2R^{64}$;

where each $R^{64}$ individually is $C_{1-12}$ alkyl;

provided, however, that when $X^1$ is selected from d), then $X^3$ is selected from the group consisting of e), f), g), h), i) and j).

In another aspect, a method for treating Flaviviridae viral infections is provided comprising administering a therapeutically effective amount of a compound of Formula I to a mammal in need thereof. The compound of Formula I is administered to a human subject in need thereof, such as a human being who is infected with viruses of the Flaviviridae family. In another embodiment, the compound of Formula I is administered to a human subject in need thereof, such as a human being who is infected with a HCV virus. In one embodiment, the treatment results in the reduction of one or more of the in viral loads or clearance of viral RNA in a patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula I, or a pharmaceutically acceptable salt or ester thereof.

In another aspect, provided is the use of a compound of Formula I for the manufacture of a medicament for the treatment of Flaviviridae viral infections. In another aspect, provided is a compound of Formula I for use in treating a Flaviviridae viral infection. In one embodiment, the Flaviviridae viral infection is acute or chronic HCV infection. In one embodiment of each aspect of use and compound, the treatment results in the reduction of one or more of the viral loads or clearance of RNA in the patient.

In another aspect, provided is a method for treating or preventing HCV comprising administering an effective amount of a compound of Formula I to a patient in need thereof. In another aspect, provided is the use of a compound of the present invention for the manufacture of a medicament for the treatment or prevention of HCV.

In another aspect, provided is a use of a compound of Formula I for the treatment of a Flaviviridae viral infection or a Hepatitis C virus infection.

In another aspect, provided is a pharmaceutical composition comprising a compound of Formula I or a pharmaceutically acceptable salt or ester thereof and one or more pharmaceutically acceptable carriers or excipients. The pharmaceutical composition of Formula I may further comprise one or more additional therapeutic agents. The one or more additional therapeutic agent may be, without limitation, selected from: interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

In another aspect, provided is a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another embodiment, provided are compounds of Formula I and pharmaceutically acceptable salts and esters thereof and all racemates, enantiomers, diastereomers, tautomers, polymorphs, pseudopolymorphs and amorphous forms thereof.

In another aspect, provided are processes and novel intermediates disclosed herein which are useful for preparing Formula I compounds.

In other aspects, novel methods for synthesis, analysis, separation, isolation, purification, characterization, and testing of the compounds of Formula I are provided.

The present invention includes combinations of aspects and embodiments, as well as preferences, as herein described throughout the present specification.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined herein.

Each document referenced herein is incorporated by reference in its entirety for all purposes.

In one embodiment of Formula I, $R^1$ is -$(L^1)_m$-$(L^2)_n$-$X^1$, $L^1$ is alkynylene and n is 0. In another aspect of this embodiment, $L^1$ is ethynylene. In another aspect of this embodiment, $X^1$ is optionally substituted $C_{1-12}$ alkyl, optionally substituted $C_{2-12}$ alkenyl, optionally substituted $C_{2-12}$ alkynyl or optionally substituted $C_{3-12}$ cycloalkyl. In another aspect of this embodiment, $X^1$ is optionally substituted $C_{1-12}$ alkyl. In another aspect of this embodiment, $X^1$ is optionally substituted $C_3$-$C_7$ secondary or tertiary alkyl. In another aspect of this embodiment, $X^1$ is optionally substituted $C_3$-$C_5$ cycloalkyl. In another aspect of this embodiment, $X^1$ is prop-2-yl (isopropyl) or 2-methylprop-2-yl (1-butyl).

In one embodiment of Formula I, $R^1$ is -$(L^1)_m$-$(L^2)_n$-$X^1$, $L^1$ is alkynylene and n is 1. In another aspect of this embodiment, $L^1$ is ethynylene. In another aspect of this embodiment, $L^2$ is optionally substituted $C_{1-12}$ alkylene. In another aspect of this embodiment, $L^2$ is optionally substituted $C_5$-$C_7$ alkylene. In another aspect of this embodiment, $X^1$ is —P(O)$R^xR^y$. In another aspect of this embodiment, $X^1$ is —P(O)$R^xR^y$ wherein each $R^x$ and $R^y$ is independently optionally substituted $C_{1-12}$ alkyl. In another aspect of this embodiment, $X^1$ is —P(O)(CH$_3$)$_2$. In another aspect of this embodiment, $X^1$ is —P(O)OR$^x$R$^y$. In another aspect of this embodiment, $X^1$ is —P(O)OR$^x$R$^y$ wherein each $R^x$ and $R^y$ is independently optionally substituted $C_{1-12}$ alkyl. In another aspect of this embodiment, $X^1$ is —P(O)(OCH$_3$)(CH$_3$). In another aspect of this embodiment, $X^1$ is —OP(O)$R^xR^y$. In another aspect of this embodiment, $X^1$ is —OP(O)$R^xR^y$ wherein each $R^x$ and $R^y$ is independently optionally substituted $C_{1-12}$ alkyl. In another aspect of this embodiment, $X^1$ is —OP(O)(CH$_3$)$_2$.

In one embodiment of Formula I, $R^1$ is -$(L^1)_m$-$(L^2)_n$-$X^1$, $L^1$ is optionally substituted arylene and n is 0. In another aspect of this embodiment, $L^1$ is phenylene. In another aspect of this embodiment, $X^1$ is optionally substituted 3-14 membered heteroaryl. In another aspect of this embodiment, $X^1$ is a 5-10 membered heteroaryl comprising one to three nitrogen atoms.

In one embodiment of Formula I, $R^1$ is -$(L^1)_m$-$(L^2)_n$-$X^1$, $L^1$ is optionally substituted arylene and n is 1. In another aspect of this embodiment, t: is phenylene. In another aspect of this embodiment, $L^2$ is optionally substituted $C_{1-12}$ alkylene. In another aspect of this embodiment, $L^2$ is optionally substituted $C_5$-$C_7$ alkylene. In another aspect of this embodiment, $L^2$ is methylene. In another aspect of this embodiment, $L^2$ is —NHC(O)—. In another aspect of this embodiment, $X^1$ is —P(O)$R^xR^y$. In another aspect of this embodiment, $X^1$ is —P(O)$R^xR^y$ wherein each $R^x$ and $R^y$ is independently optionally substituted $C_{1-12}$ alkyl. In another aspect of this embodiment, $X^1$ is —P(O)(CH$_3$)$_2$. In another aspect of this embodiment, $X^1$ is —P(O)OR$^x$R$^y$. In another aspect of this embodiment, $X^1$ is —P(O)R$^x$R$^y$ wherein each $R^x$ and $R^y$ is independently optionally substituted $C_{1-12}$ alkyl. In another aspect of this embodiment, $X^1$ is —P(O)(OR$^x$)(CH$_3$). In another aspect of this embodiment, $X^1$ is —P(O)(OR$^x$)(CH$_3$) wherein $R^x$ is H or $C_{1-6}$ alkyl. In another aspect of this embodiment, $X^1$ is —OP(O)$R^xR^y$. In another aspect of this embodiment, $X^1$ is —OP(O)$R^xR^y$ wherein each $R^x$ and $R^y$ is independently optionally substituted $C_{1-12}$ alkyl. In another aspect of this embodiment, $X^1$ is —OP(O)(CH$_3$)$_2$. In another aspect of this embodiment, $X^1$ is optionally substituted 3-14 membered heteroaryl. In another aspect of this embodiment, $X^1$ is thiazolyl.

In another embodiment of Formula I, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

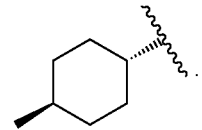 [SMILES: *[C@H]1CC[C@H](C)CC1]

In another preferred aspect of this embodiment, $R^2$ is

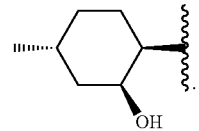 [SMILES: *[C@@H]1CC[C@@H](C)C[C@@H]1O]

In another preferred aspect of this embodiment, $R^2$ is

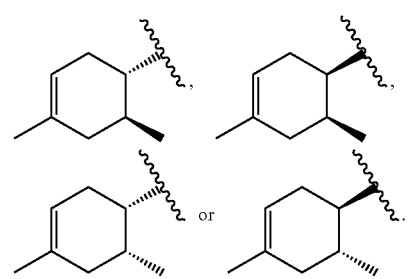

In another preferred aspect of this embodiment, R² is

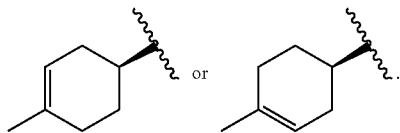

In one embodiment of Formula I, R³ is -(L³)$_p$-(L⁴)$_q$-(X³) wherein p and q are each 0. In another aspect of this embodiment X³ is optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl or optionally substituted C$_{6-18}$ arylalkyl. In another aspect of this embodiment, X³ is optionally substituted C$_{3-12}$ cycloalkyl. In another aspect of this embodiment, X³ is optionally substituted cyclohexyl. In another aspect of this embodiment, X³ is

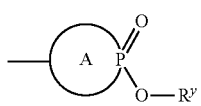

wherein each A is a 4 to 6 membered ring, including the depicted P atom. In another aspect of this embodiment, X³ is

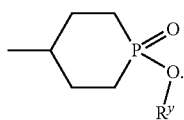

In another aspect of this embodiment, X³ is

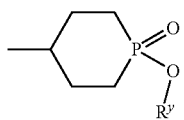

wherein R$^y$ is H or C$_{1-6}$ alkyl.

In one embodiment of Formula I, R³ is -(L³)$_p$-(L⁴)$_q$-(X³) wherein p is 1 and q is 0. In another aspect of this embodiment, L³ is optionally substituted C$_{1-12}$ alkylene, optionally substituted C$_{2-12}$ alkenylene, optionally substituted C$_{2-12}$ alkynylene, optionally substituted C$_{3-12}$ cycloalkylene or optionally substituted 3-12 membered heterocyclylene. In another aspect of this embodiment, L³ is optionally substituted C$_{1-12}$ alkylene. In another aspect of this embodiment, L³ is optionally substituted ethylene. In another aspect of this embodiment, L³ is optionally substituted C$_{3-12}$ cycloalkylene. In another aspect of this embodiment, L³ is optionally substituted C$_{4-6}$ cycloalkylene. In another aspect of this embodiment, L³ is optionally substituted cyclohexylene. In another aspect of this embodiment, L³ is optionally substituted 3-12 membered heterocyclylene. In another aspect of this embodiment, L³ is optionally substituted 5-6 membered N-containing heterocyclene. In another aspect of this embodiment, L³ is piperidinylene. In another aspect of this embodiment, X³ is —P(O)R$^x$R$^y$. In another aspect of this embodiment, X³ is —P(O)R$^x$R$^y$ wherein each R$^x$ and R$^y$ is independently optionally substituted C$_{1-12}$ alkyl. In another aspect of this embodiment, X³ is —P(O)R$^x$R$^y$ wherein each R$^x$ and R$^y$ is independently ethyl or methyl. In another aspect of this embodiment, X³ is —P(O)OR$^x$R$^y$. In another aspect of this embodiment, X³ is —P(O)OR$^x$R$^y$ wherein each R$^x$ and R$^y$ ia independently optionally substituted C$_{1-12}$ alkyl. In another aspect of this embodiment, X³ is —P(O)(OR$^x$)(CH₃). In another aspect of this embodiment, X³ is —P(O)(OR$^x$)(CH₃) wherein R$^x$ is H or C$_{1-6}$ alkyl. In another aspect of this embodiment, X³ is —OP(O)R$^x$R$^y$. In another aspect of this embodiment, X³ is —OP(O)R$^x$R$^y$ wherein each R$^x$ and R$^y$ is independently optionally substituted C$_{1-12}$ alkyl. In another aspect of this embodiment, X³ is —OP(O)(CH₃)₂. In another aspect of this embodiment, X³ is —OP(O)R$^x$R$^y$ wherein each R$^x$ and R$^y$ is independently methyl, ethyl, or optionally substituted phenyl. In another aspect of this embodiment, X³ is —OP(O)R$^x$R$^y$ wherein each R$^x$ and R$^y$ is independently methyl or ethyl. In another aspect of this embodiment, X³ is —P(O)(OR$^x$)(OR$^y$). In another aspect of this embodiment, X³ is

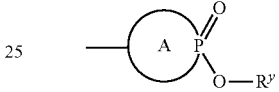

wherein each A is a 4 to 6 membered ring, including the depicted P atom. In another aspect of this embodiment, X³ is

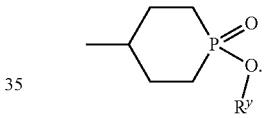

In another aspect of this embodiment, X³ is

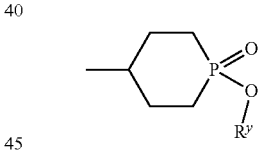

wherein R$^y$ is H or C$_{1-6}$ alkyl.

In one embodiment of Formula I, R³ is -(L³)$_p$-(L⁴)$_q$-(X³) wherein p is 1 and q is 1. In another aspect of this embodiment, L³ is optionally substituted C$_{1-12}$ alkylene, optionally substituted C$_{2-12}$ alkenylene, optionally substituted C$_{2-12}$ alkynylene, optionally substituted C$_{3-12}$ cycloalkylene or optionally substituted 3-12 membered heterocyclylene. In another aspect of this embodiment, L³ is optionally substituted C$_{3-12}$ cycloalkylene. In another aspect of this embodiment, L³ is optionally substituted C$_{4-6}$ cycloalkylene. In another aspect of this embodiment, L³ is optionally substituted cyclohexylene. In another aspect of this embodiment, L⁴ is —NH—. In another aspect of this embodiment, L⁴ is optionally substituted C$_{1-12}$ alkylene. In another aspect of this embodiment, X³ is —P(O)R$^x$R$^y$. In another aspect of this embodiment, X³ is —P(O)R$^x$R$^Y$ wherein each R$^x$ and R$^y$ is independently optionally substituted C$_{1-12}$ alkyl. In another aspect of this embodiment, X³ is —P(O)R$^x$R$^y$ wherein each R$^x$ and R$^y$ is independently ethyl or methyl. In another aspect of this embodiment, X³ is —P(O)OR$^x$R$^y$. In another aspect of this embodiment, X³ is —OP(O)R$^x$R$^y$ wherein each R$^x$ and R$^y$ is independently optionally substituted $C_{1-12}$ alkyl. In another aspect of this embodiment, $X^3$ is —P(O)(OR$^x$)(CH$_3$). In another aspect of this embodiment, $X^3$ is —P(O)(OR$^x$)(CH$_3$) wherein R$^x$ is H or $C_{1-6}$ alkyl. In another aspect of this embodiment, $X^3$ is —OP(O)R$^x$R$^y$. In another aspect of this embodiment, $X^3$ is —OP(O)R$^x$R$^y$ wherein each R$^x$ and R$^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)R$^x$R$^y$ wherein each R$^x$ and R$^y$ is independently methyl, ethyl, or optionally substituted phenyl. In another aspect of this embodiment, $X^3$ is —OP(O)R$^x$R$^y$ wherein each R$^x$ and R$^y$ is independently methyl or ethyl. In another aspect of this embodiment, $X^3$ is —P(O)(OR$^x$)(OR$^y$). In another aspect of this embodiment, $X^3$ is

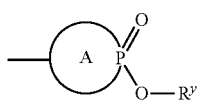

wherein each A is a 4 to 6 membered ring, including the depicted P atom. In another aspect of this embodiment, $X^3$ is

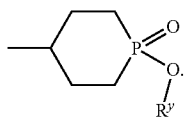

In another aspect of this embodiment, $X^3$ is

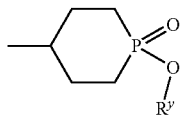

wherein R$^y$ is H or $C_{1-6}$ alkyl.

In one embodiment of Formula I, $R^3$ is -(L$^3$)$_p$-(L$^4$)$_q$-(X$^3$) wherein p is 1 and q is 2. In another aspect of this embodiment, L$^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, L$^3$ is optionally substituted $C_{3-12}$ cycloalkylene. In another aspect of this embodiment, L$^3$ is optionally substituted $C_{4-6}$ cycloalkylene. In another aspect of this embodiment, L$^3$ is optionally substituted cyclohexylene. In another aspect of this embodiment, L$^4$ is —NH—. In another aspect of this embodiment, L$^4$ is optionally substituted $C_{1-12}$ alkylene. In another aspect of this embodiment, one of L$^4$ is —NH— and the other L$^4$ is optionally substituted $C_{1-12}$ alkylene. In another aspect of this embodiment, $X^3$ is —P(O)R$^x$R$^y$. In another aspect of this embodiment, $X^3$ is —P(O)R$^x$R$^y$ wherein each R$^x$ and R$^y$ is independently optionally substituted $C_{1-12}$ alkyl. In another aspect of this embodiment, $X^3$ is —P(O)R$^x$R$^y$ wherein each R$^x$ and R$^y$ is independently ethyl or methyl. In another aspect of this embodiment, $X^3$ is —P(O)OR$^x$R$^y$. In another aspect of this embodiment, $X^3$ is —P(O)OR$^x$R$^y$ wherein each R$^x$ and R$^y$ is independently optionally substituted $C_{1-12}$ alkyl. In another aspect of this embodiment, $X^3$ is —P(O)(OR$^x$)(CH$_3$). In another aspect of this embodiment, $X^3$ is —P(O)(OR$^x$)(CH$_3$) wherein R$^x$ ia H or $C_{1-6}$ alkyl. In another aspect of this embodiment, $X^3$ is —OP(O)R$^x$R$^y$. In another aspect of this embodiment, $X^3$ is —OP(O)R$^x$R$^y$ wherein each R$^x$ and R$^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)R$^x$R$^y$ wherein each R$^x$ and R$^y$ is independently methyl, ethyl, or optionally substituted phenyl. In another aspect of this embodiment, $X^3$ is —OP(O)R$^x$R$^y$ wherein each R$^x$ and R$^y$ is independently methyl or ethyl. In another aspect of this embodiment, $X^3$ is —P(O)(OR$^x$)(OR$^y$). In another aspect of this embodiment, $X^3$ is —P(O)(OR$^x$)(OR$^y$) wherein each R$^x$ and R$^y$ is independently methyl or ethyl. In another aspect of this embodiment, $X^3$ is

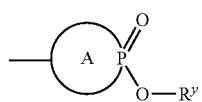

wherein each A is a 4 to 6 membered ring, including the depicted P atom. In another aspect of this embodiment, $X^3$ is

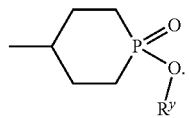

In another aspect of this embodiment, $X^3$ is

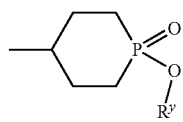

wherein R$^y$ is H or $C_{1-6}$ alkyl.

In another embodiment of Formula I, $R^1$ is -(L$^1$)$_m$(L$^2$)$_n$-X$^1$, L$^1$ is alkynylene, n is 0, and $R^3$ is -(L$^3$)$_p$-(L$^4$)$_q$-(X$^3$) wherein p and q are each 0. In another aspect of this embodiment, L is ethynylene. In another aspect of this embodiment, $X^1$ is optionally substituted $C_{1-12}$ alkyl, optionally substituted $O_{2-12}$ alkenyl, optionally substituted $C_{2-12}$ alkynyl or optionally substituted $C_{3-12}$ cycloalkyl. In another aspect of this embodiment, $X^1$ is optionally substituted $C_{1-12}$ alkyl. In another aspect of this embodiment, $X^1$ is optionally substituted $C_3$-$C_7$ secondary or tertiary alkyl. In another aspect of this embodiment, $X^1$ is optionally substituted $C_3$-$C_5$ cycloalkyl. In another aspect of this embodiment, $X^1$ is prop-2-yl (isopropyl) or 2-methylprop-2-yl(t-butyl).

In another aspect of this embodiment, $X^3$ is

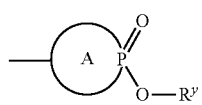

wherein each A is a 4 to 6 membered ring, including the depicted P atom. In another aspect of this embodiment, $X^3$ is

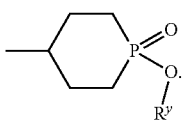

In another aspect of this embodiment, X³ is

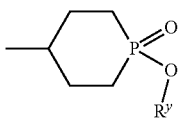

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

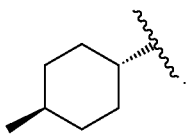

In another preferred aspect of this embodiment, $R^2$ is

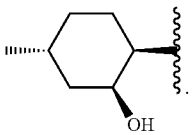 [SMILES: *[C@@H]1CC[C@@H](C)C[C@@H]1O]

In another preferred aspect of this embodiment, $R^2$ is

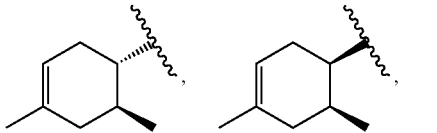

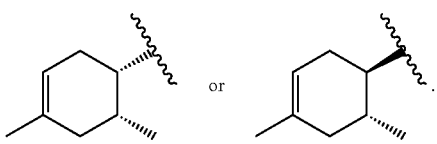

In another preferred aspect of this embodiment, $R^2$ is

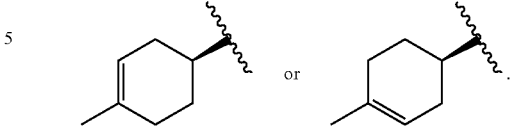

In another embodiment of Formula I, $R^1$ is $-(L^1)_m-(L^2)_n-X^1$, $L^1$ is alkynylene, n is 0 and $R^3$ is $-(L^3)_p-(L^4)_q-(X^3)$ wherein p is 1 and q is 0. In another aspect of this embodiment, $L^1$ is ethynylene. In another aspect of this embodiment, $X^1$ is optionally substituted $C_{1-12}$ alkyl, optionally substituted $C_{2-12}$ alkenyl, optionally substituted $C_{2-12}$ alkynyl or optionally substituted $C_{3-12}$ cycloalkyl. In another aspect of this embodiment, $X^1$ is optionally substituted $C_{1-12}$ alkyl. In another aspect of this embodiment, X' is optionally substituted $C_3-C_7$ secondary or tertiary alkyl. In another aspect of this embodiment, $X^1$ is optionally substituted $C_3-C_5$ cycloalkyl. In another aspect of this embodiment, $X^1$ is prop-2-yl(isopropyl) or 2-methylprop-2-yl (t-butyl). In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{1-12}$ alkylene. In another aspect of this embodiment, $L^3$ is optionally substituted ethylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^3$ is optionally substituted 3-12 membered heterocyclylene. In another aspect of this embodiment, $L^3$ is optionally substituted 5-6 membered N-containing heterocyclene. In another aspect of this embodiment, $L^3$ is piperidinylene. In another aspect of this embodiment, $X^3$ is $-P(O)R^xR^y$. In another aspect of this embodiment, $X^3$ is $-P(O)R^xR^y$ wherein each $R^x$ and $R^y$ is independently optionally substituted $C_{1-12}$ alkyl. In another aspect of this embodiment, $X^3$ is $-P(O)R^xR^y$ wherein each $R^x$ and $R^y$ is independently ethyl or methyl. In another aspect of this embodiment, $X^3$ is $-P(O)OR^xR^y$. In another aspect of this embodiment, $X^3$ is $-P(O)OR^xR^y$ wherein each $R^x$ and $R^y$ is independently optionally substituted $C_{1-12}$ alkyl. In another aspect of this embodiment, $X^3$ is $-P(O)(OR^x)(CH_3)$. In another aspect of this embodiment, $X^3$ is $-P(O)(OR^x)(CH_3)$ wherein $R^x$ is H or $C_{1-6}$ alkyl. In another aspect of this embodiment, $X^3$ is $-OP(O)R^xR^y$. In another aspect of this embodiment, $X^3$ is $-OP(O)R^xR^y$ wherein each $R^x$ and $R^y$ is independently optionally substituted $C_{1-12}$ alkyl. In another aspect of this embodiment, $X^3$ is $-OP(O)(CH_3)_2$. In another aspect of this embodiment, $X^3$ is $-OP(O)R^xR^y$ wherein each $R^x$ and $R^y$ is independently methyl, ethyl, or optionally substituted phenyl. In another aspect of this embodiment, $X^3$ is $-OP(O)R^xR^y$ wherein each $R^x$ and $R^y$ is independently methyl or ethyl. In another aspect of this embodiment, $X^3$ is $-P(O)(OR^x)(OR^y)$, In another aspect of this embodiment, $X^3$ is $-P(O)(OR^x)(OR^y)$ wherein each $R^x$ and $R^y$ is independently methyl or ethyl. In another aspect of this embodiment, $X^3$ is

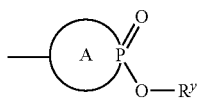

wherein each A is a 4 to 6 membered ring, including the depicted P atom. In another aspect of this embodiment, $X^3$ is

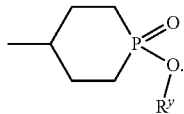

In another aspect of this embodiment, $X^3$ is

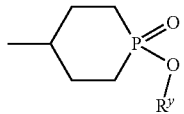

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

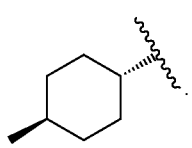 [SMILES: *[C@H]1CC[C@H](C)CC1]

In another preferred aspect of this embodiment, $R^2$ is

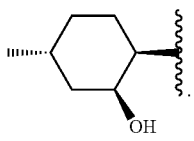 [SMILES: *[C@@H]1CC[C@@H](C)C[C@@H]1O]

In another preferred aspect of this embodiment, $R^2$ is

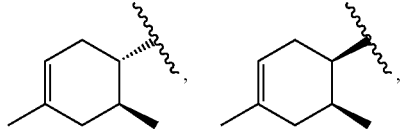

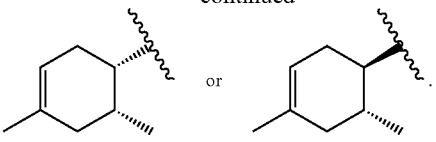

In another preferred aspect of this embodiment, $R^2$ is

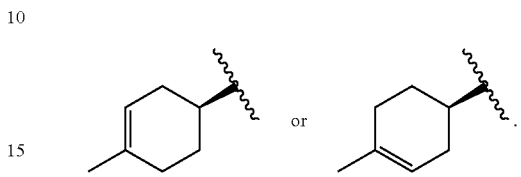

In another embodiment of Formula I, $R^1$ is $-(L^1)_m-(L^2)_n-X^1$, $L^1$ is alkynylene, n is 0, and $R^3$ is $-(L^3)_p-(L^4)_q-(X^3)$ wherein p is 1 and q is 1. In another aspect of this embodiment, $L^1$ is ethynylene. In another aspect of this embodiment, $X^1$ is optionally substituted $C_{1-12}$ alkyl, optionally substituted $C_{2-12}$ alkenyl, optionally substituted $C_{2-12}$ alkynyl or optionally substituted $O_{3-12}$ cycloalkyl. In another aspect of this embodiment, $X^1$ is optimally substituted $C_{1-12}$ alkyl. In another aspect of this embodiment, $X^1$ is optionally substituted $C_3-C_7$ secondary or tertiary alkyl. In another aspect of this embodiment, $X^1$ is optionally substituted $C_3-C_5$ cycloalkyl. In another aspect of this embodiment, $X^1$ is prop-2-yl (isopropyl) or 2-methylprop-2-yl (t-butyl). In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^4$ is —NH—. In another aspect of this embodiment, $L^4$ is optionally substituted $C_{1-12}$ alkylene. In another aspect of this embodiment, $X^3$ is —P(O)$R^xR^y$. In another aspect of this embodiment, $X^3$ is —P(O)$R^xR^y$ wherein each $R^x$ and $R^y$ is independently optionally substituted $C_{1-12}$ alkyl. In another aspect of this embodiment, $X^3$ is —P(O)$R^xR^y$ wherein each $R^x$ and $R^y$ is independently ethyl or methyl. In another aspect of this embodiment, $X^3$ is —P(O)OR$^x$R$^y$. In another aspect of this embodiment, $X^3$ is —P(O)OR$^x$R$^y$ wherein each $R^x$ and $R^y$ is independently optionally substituted $C_{1-12}$ alkyl. In another aspect of this embodiment, $X^3$ is —P(O)(OR$^x$)(CH$_3$). In another aspect of this embodiment, $X^3$ is —P(O)(OR$^x$)(CH$_3$) wherein $R^x$ is H or $C_{1-6}$ alkyl. In another aspect of this embodiment, $X^3$ is —OP(O)R$^x$R$^y$. In another aspect of this embodiment, $X^3$ is —OP(O)R$^x$R$^y$ wherein each $R^x$ and $R^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)R$^x$R$^y$ wherein each $R^x$ and $R^y$ is independently methyl, ethyl, or optionally substituted phenyl. In another aspect of this embodiment, $X^3$ is —OP(O)R$^x$R$^y$ wherein each Fr and $R^y$ is independently methyl or ethyl. In another aspect of this embodiment, $X^3$ is —P(O)(OR$^x$)(OR$^y$). In another aspect of this embodiment, $X^3$ is —P(O)(OR$^x$)(OR$^y$) wherein each $R^x$ and $R^y$ is independently methyl or ethyl. In another aspect of this embodiment, $X^3$ is

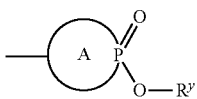

wherein each A is a 4 to 6 membered ring, including the depicted P atom. In another aspect of this embodiment, $X^3$ is

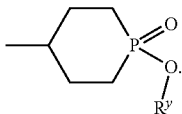

In another aspect of this embodiment, $X^3$ is

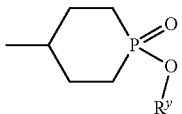

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

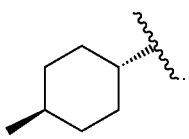

In another preferred aspect of this embodiment, $R^2$ is

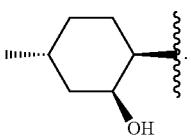

In another preferred aspect of this embodiment, $R^2$ is

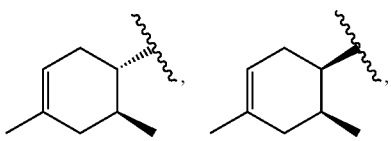

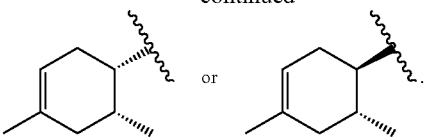

In another preferred aspect of this embodiment, $R^2$ is

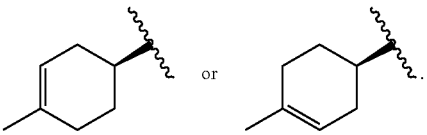

In another embodiment of Formula I, $R^1$ is $-(L^1)_m-(L^2)_n-X^1$, $L^1$ is alkynylene, n is 0, and $R^3$ is $-(L^3)_p-(L^4)_q-(X^3)$ wherein p is 1 and q is 2. In another aspect of this embodiment, $L^1$ is ethynylene. In another aspect of this embodiment, $X^1$ is optionally substituted $C_{1-12}$ alkyl, optionally substituted $C_{2-12}$ alkenyl, optionally substituted $C_{2-12}$ alkynyl or optionally substituted $C_{3-12}$ cycloalkyl. In another aspect of this embodiment, $X^1$ is optionally substituted $C_{1-12}$ alkyl. In another aspect of this embodiment, $X^1$ is optionally substituted $C_3-C_7$ secondary or tertiary alkyl. In another aspect of this embodiment, $X^1$ is optionally substituted $C_3-C_5$ cycloalkyl. In another aspect of this embodiment, $X^1$ is prop-2-yl (isopropyl) or 2-methylprop-2-yl (t-butyl). In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^4$ is —NH—. In another aspect of this embodiment, $L^4$ is optionally substituted $C_{1-12}$ alkylene. In another aspect of this embodiment, one of $L^4$ is —NH— and the other $L^4$ is $C_{1-12}$ alkylene. In another aspect of this embodiment, $-(L^4)_2-$ is —NH—$C_{1-6}$ alkylene. In another aspect of this embodiment, $X^3$ is —P(O)$R^xR^y$. In another aspect of this embodiment, $X^3$ is —P(O)$R^xR^y$ wherein each $R^x$ and $R^y$ is independently optionally substituted $C_{1-12}$ alkyl. In another aspect of this embodiment, $X^3$ is —P(O)$R^xR^y$ wherein each $R^x$ and $R^y$ is independently ethyl or methyl. In another aspect of this embodiment, $X^3$ is —P(O)O$R^xR^y$. In another aspect of this embodiment, $X^3$ is —P(O)O$R^xR^y$ wherein each $R^x$ and $R^y$ is independently optionally substituted $C_{1-12}$ alkyl. In another aspect of this embodiment, $X^3$ is —P(O)(O$R^x$)(CH$_3$). In another aspect of this embodiment, $X^3$ is —P(O)(O$R^x$)(CH$_3$) wherein $R^x$ is H or $C_{1-6}$ alkyl. In another aspect of this embodiment, $X^3$ is —OP(O)$R^xR^y$. In another aspect of this embodiment, $X^3$ is —OP(O)$R^xR^y$ wherein each $R^x$ and $R^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)$R^xR^y$ wherein each $R^x$ and $R^y$ is independently methyl, ethyl, or optionally substituted phenyl. In another aspect of this embodiment, $X^3$ is —OP(O)$R^xR^y$ wherein each $R^x$ and $R'$ is independently methyl or ethyl. In another aspect of this embodiment, $X^3$ is —P(O)(O$R^x$)(O$R^y$). In another aspect of this embodiment, $X^3$ is —P(O)(O$R^x$)(O$R^y$) wherein each $R^x$ and $R^y$ is independently methyl or ethyl. In another aspect of this embodiment, $X^3$ is

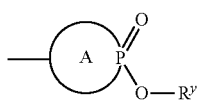

wherein each A is a 4 to 6 membered ring, including the depicted P atom. In another aspect of this embodiment, $X^3$ is

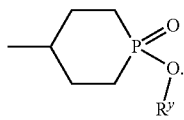

In another aspect of this embodiment, $X^3$ is

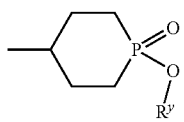

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

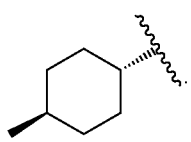

In another preferred aspect of this embodiment, $R^2$ is

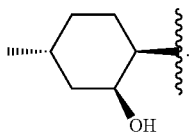

In another preferred aspect of this embodiment, $R^2$ is

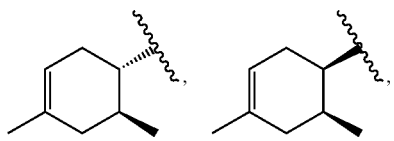

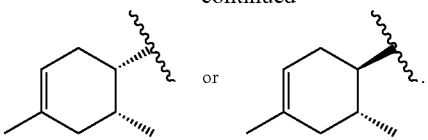

In another preferred aspect of this embodiment, $R^2$ is

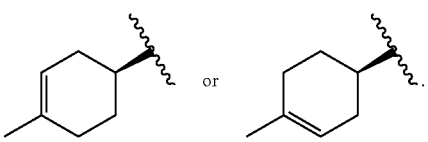

In one embodiment of Formula I, $R^1$ is -$(L^1)_m$-$(L^2)_n$-$X^1$, $L^1$ optionally substituted arylene, n is 0 and $R^3$ is -$(L^3)_p$-$(L^4)_q$-$(X^3)$ wherein p is 1 and q is 0. In another aspect of this embodiment, $L^1$ is phenylene. In another aspect of this embodiment, $X^1$ is optionally substituted 3-14 membered heteroaryl. In another aspect of this embodiment, $X^1$ is a 5-10 membered heteroaryl comprising one to three nitrogen atoms. In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{1-12}$ alkylene. In another aspect of this embodiment, $L^3$ is optionally substituted ethylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^3$ is optionally substituted 3-12 membered heterocyclylene. In another aspect of this embodiment, $L^3$ is optionally substituted 5-6 membered N-containing heterocyclene. In another aspect of this embodiment, $L^3$ is piperidinylene. In another aspect of this embodiment, $X^3$ is —P(O)$R^xR^y$. In another aspect of this embodiment, $X^3$ is —P(O)$R^xR^y$ wherein each $R^x$ and $R^y$ is independently optionally substituted $C_{1-12}$ alkyl. In another aspect of this embodiment, $X^3$ is —P(O)$R^xR^y$ wherein each $R^x$ and $R^y$ is independently ethyl or methyl. In another aspect of this embodiment, $X^3$ is —P(O)OR$^xR^y$. In another aspect of this embodiment, $X^3$ is —P(O)OR$^xR^y$ wherein each $R^x$ and $R^y$ is independently optionally substituted $C_{1-12}$ alkyl. In another aspect of this embodiment, $X^3$ is —P(O)(OR$^x$)(CH$_3$). In another aspect of this embodiment, $X^3$ is —P(O)(OR$^x$)(CH$_3$) wherein $R^x$ is H or $C_{1-6}$ alkyl. In another aspect of this embodiment, $X^3$ is —OP(O)$R^xR^y$. In another aspect of this embodiment, $X^3$ is —OP(O)$R^xR^y$ wherein each $R^x$ and $R^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)$R^xR^y$ wherein each $R^x$ and $R^y$ is independently methyl, ethyl, or optionally substituted phenyl. In another aspect of this embodiment, $X^3$ is —OP(O)$R^xR^y$ wherein each $R^x$ and $R^y$ is independently methyl or ethyl. In another aspect of this embodiment, $X^3$ is

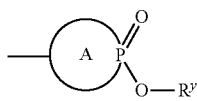

wherein each A is a 4 to 6 membered ring, including the depicted P atom. In another aspect of this embodiment, $X^3$ is

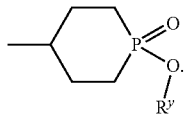

In another aspect of this embodiment, $X^3$ is

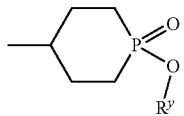

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

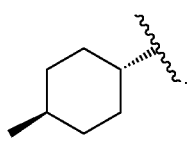

In another preferred aspect of this embodiment, $R^2$ is

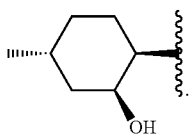 [SMILES: *[C@@H]1CC[C@@H](C)C[C@@H]1O]

In another preferred aspect of this embodiment, $R^2$ is

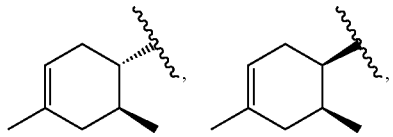

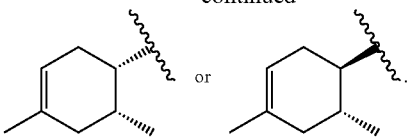

In another preferred aspect of this embodiment, $R^2$ is

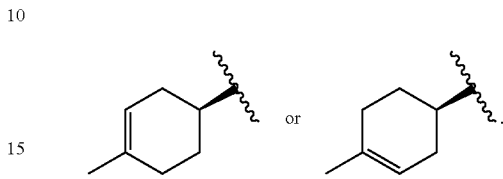

In one embodiment of Formula I, $R^1$ is $-(L^1)_m-(L^2)_n-X^1$, $L^1$ optionally substituted arylene n is 1 and $R^3$ is $-(L^3)_p-(L^4)_q-(X^3)$ wherein p is 1 and q is 0. In another aspect of this embodiment, $L^1$ is phenylene. In another aspect of this embodiment, $L^2$ is —NHC(O)—. In another aspect of this embodiment, $X^1$ is optionally substituted 3-14 membered heteroaryl. In another aspect of this embodiment, $X^1$ is thiazolyl. In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{1-12}$ alkylene. In another aspect of this embodiment, $L^3$ is optionally substituted ethylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^3$ is optionally substituted 3-12 membered heterocyclylene. In another aspect of this embodiment, $L^3$ is optionally substituted 5-6 membered N-containing heterocyclene. In another aspect of this embodiment, $L^3$ is piperidinylene. In another aspect of this embodiment, $X^3$ is —P(O)$R^xR^y$. In another aspect of this embodiment, $X^3$ is —P(O)$R^xR^y$ wherein each $R^x$ and $R^y$ is independently optionally substituted $C_{1-12}$ alkyl. In another aspect of this embodiment, $X^3$ is —P(O)$R^xR^y$ wherein each $R^x$ and $R^y$ is independently ethyl or methyl. In another aspect of this embodiment, $X^3$ is —P(O)O$R^xR^y$. In another aspect of this embodiment, $X^3$ is —P(O)O$R^xR^y$ wherein each $R^x$ and $R^y$ is independently optionally substituted $C_{1-12}$ alkyl. In another aspect of this embodiment, $X^3$ is —P(O)(O$R^x$)(CH$_3$). In another aspect of this embodiment, $X^3$ is —P(O)(O$R^x$)(CH$_3$) wherein $R^x$ is H or $C_{1-6}$ alkyl. In another aspect of this embodiment, $X^3$ is —OP(O)$R^xR^y$. In another aspect of this embodiment, $X^3$ is —OP(O)$R^xR^y$ wherein each $R^x$ and $R^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)$R^xR^y$ wherein each $R^x$ and $R^y$ is independently methyl, ethyl, or optionally substituted phenyl. In another aspect of this embodiment, $X^3$ is —OP(O)$R^xR^y$ wherein each $R^x$ and $R^y$ is independently methyl or ethyl. In another aspect of this embodiment, $X^3$ is

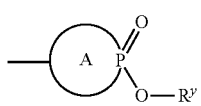

wherein each A is a 4 to 6 membered ring, including the depicted P atom. In another aspect of this embodiment, $X^3$ is

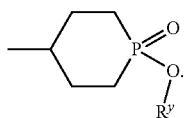

In another aspect of this embodiment, $X^3$ is

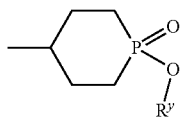

wherein $R^y$ is H or $C_{1-6}$ alkyl. In another aspect of this embodiment, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

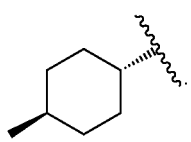

In another preferred aspect of this embodiment, $R^2$ is

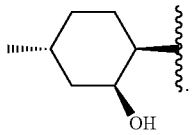 [SMILES: *[C@@H]1CC[C@@H](C)C[C@@H]1O]

In another preferred aspect of this embodiment, $R^2$ is

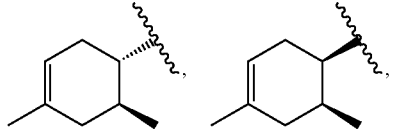

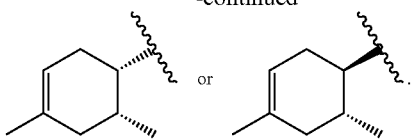

In another preferred aspect of this embodiment, $R^2$ is

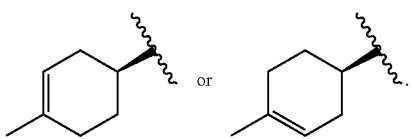

In another embodiment, compounds of Formula I are represented by compounds of Formula II:

Formula II

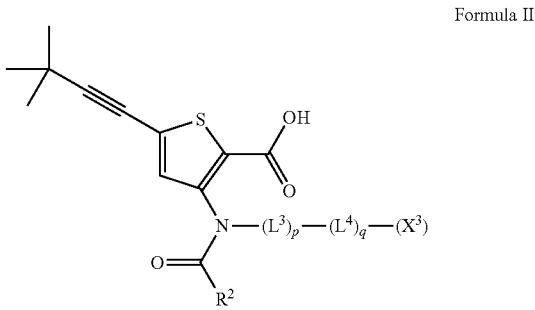

or pharmaceutically acceptable salts and esters thereof, wherein:

$R^2$ is optionally substituted 4-methylcyclohexyl or optionally substituted methylcyclohexenyl;

$X^3$ is selected from the group consisting of:
a) —P(O)$R^x R^y$,
b) —P(O)$R^x R^y$,
c) —OP(O)$R^x R^y$,
d) —P(O)(O$R^x$)(O$R^y$);
e)

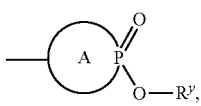

where each A is a 4 to 6 membered ring, including the depicted P atom; and
f)

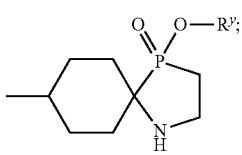

and
the remaining variables are defined as for Formula I.

in one embodiment of Formula II, R² is:

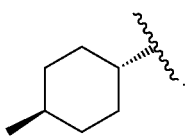 [SMILES: *[C@H]1CC[C@H](C)CC1]

In one embodiment of Formula II, R² is:

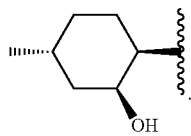

In another embodiment of Formula II, R² is

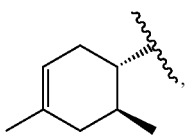 , 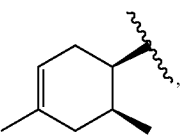 ,

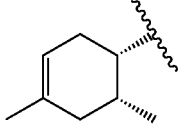 or 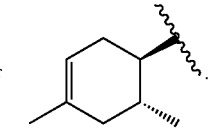 .

In another embodiment of Formula II, R² is

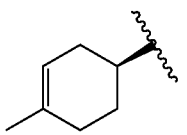 or 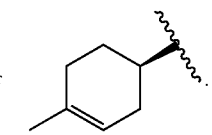 .

In another embodiment of Formula II, p and q are each 0. In another aspect of this embodiment, X³ is

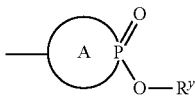

wherein each A is a 4 to 6 membered ring, including the depicted P atom. In another aspect of this embodiment, X³

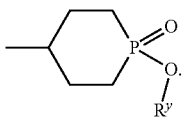

In another aspect of this embodiment, X³ is

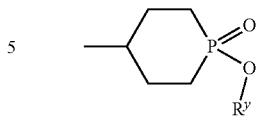

wherein $R^y$ is H or $C_{1-6}$ alkyl. In a preferred aspect of this embodiment, R² is

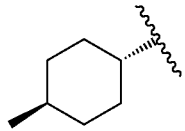

In another preferred aspect of this embodiment, R² is

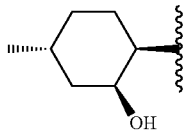

In another preferred aspect of this embodiment, R² is

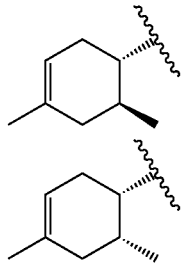

In another preferred aspect of this embodiment, R² is

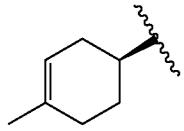

In another embodiment of Formula II, p is 1 and q is 0. In another aspect of this embodiment, L³ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, L³ is optionally substituted $C_{1-12}$ alkylene. In another aspect of this embodiment, L³ is optionally substituted ethylene. In another aspect of this embodiment, L³ is optionally substituted $C_{3-12}$ cycloalkylene. In another aspect of this embodiment, L³ is optionally substituted $C_{4-6}$ cycloalkylene. In another aspect of this embodiment, L³ is optionally substituted cyclohexylene. In another aspect of this embodiment, L³ is optionally substituted 3-12 membered heterocyclylene.

In another aspect of this embodiment, L³ is optionally substituted 5-6 membered N-containing heterocyclene. In another aspect of this embodiment, L³ is piperidinylene. In another aspect of this embodiment, X³ is —P(O)R$^x$R$^y$. In another aspect of this embodiment, X³ is —P(O)R$^x$R$^y$ wherein each R$^x$ and R$^y$ is independently optionally substituted C$_{1-12}$ alkyl. In another aspect of this embodiment, X³ is —P(O)R$^x$R$^y$ wherein each R$^x$ and R$^y$ is independently ethyl or methyl. In another aspect of this embodiment, X³ is —P(O)OR$^x$R$^y$. In another aspect of this embodiment, X³ is —P(O)OR$^x$R$^y$ wherein each R$^x$ and R$^y$ is independently optionally substituted C$_{1-12}$ alkyl. In another aspect of this embodiment, X³ is —P(O)(OR$^x$)(CH$_3$). In another aspect of this embodiment, X³ is —P(O)(OR$^x$)(CH$_3$) wherein R$^x$ is H or C$_{1-6}$ alkyl. In another aspect of this embodiment, X³ is —OP(O)R$^x$R$^y$. In another aspect of this embodiment, X³ is —OP(O)R$^x$R$^y$ wherein each R$^x$ and R$^y$ is independently optionally substituted C$_{1-12}$ alkyl. In another aspect of this embodiment, X³ is —OP(O)(CH$_3$)$_2$. In another aspect of this embodiment, X³ is —OP(O)R$^x$R$^y$ wherein each R$^x$ and R$^Y$ is independently methyl, ethyl, or optionally substituted phenyl. In another aspect of this embodiment, X³ is —OP(O)R$^x$R$^y$ wherein each R$^x$ and R$^y$ is independently methyl or ethyl. In another aspect of this embodiment, X³ is —P(O)(OR$^x$)(OR$^y$). In another aspect of this embodiment, X³ is —P(O)(OR$^x$)(OR$^y$) wherein each R$^x$ and R$^y$ is independently methyl or ethyl. In another aspect of this embodiment, X³ is

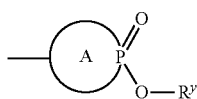

wherein each A is a 4 to 6 membered ring, including the depicted P atom. In another aspect of this embodiment, X³ is

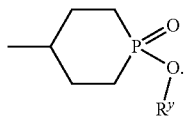

In another aspect of this embodiment, X³ is

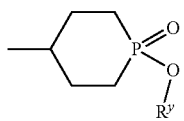

wherein R$^y$ is H or C$_{1-6}$ alkyl. In a preferred aspect of this embodiment, R² is

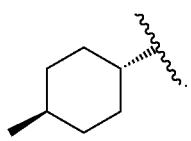

In another preferred aspect of this embodiment, R² is

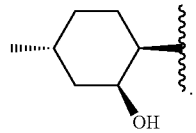 [SMILES: *[C@@H]1CC[C@@H](C)C[C@@H]1O]

In another preferred aspect of this embodiment, R² is

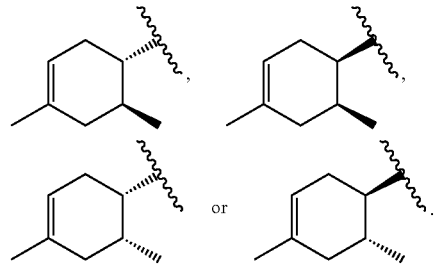

In another preferred aspect of this embodiment, R² is

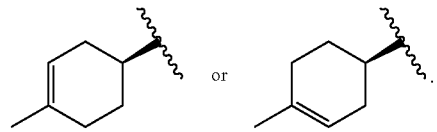

In another embodiment of Formula II, p is 1 and q is 1. In another aspect of this embodiment, L³ is optionally substituted C$_{1-12}$ alkylene, optionally substituted C$_{2-12}$ alkenylene, optionally substituted C$_{2-12}$ alkynylene, optionally substituted C$_{3-12}$ cycloalkylene or optionally substituted 3-12 membered heterocyclylene. In another aspect of this embodiment, L³ is optionally substituted C$_{3-12}$ cycloalkylene. In another aspect of this embodiment, L³ is optionally substituted C$_{4-6}$ cycloalkylene. In another aspect of this embodiment, L³ is optionally substituted cyclohexylene. In another aspect of this embodiment, L⁴ is —NH—. In another aspect of this embodiment, L⁴ is optionally substituted C$_{1-12}$ alkylene. In another aspect of this embodiment, X³ is —P(O)R$^x$R$^y$. In another aspect of this embodiment, X³ is —P(O)R$^x$R$^y$ wherein each R$^x$ and R$^y$ is independently optionally substituted C$_{1-12}$ alkyl. In another aspect of this embodiment, X³ is —P(O)R$^x$R$^y$ wherein each R$^x$ and R$^y$ is independently ethyl or methyl. In another aspect of this embodiment, X³ is —P(O)OR$^x$R$^y$. In another aspect of this embodiment, X³ is —P(O)OR$^x$R$^y$ wherein each R$^x$ and R$^y$ is independently optionally substituted C$_{1-12}$ alkyl. In another aspect of this embodiment, X³ is —P(O)(OR$^x$)(CH$_3$). In another aspect of this embodiment, X³ is —P(O)(OR$^x$)(CH$_3$) wherein R$^x$ is H or C$_{1-6}$ alkyl. In another aspect of this embodiment, X³ is —OP(O)R$^x$R$^y$. In another aspect of this embodiment, X³ is —OP(O)R$^x$R$^y$ wherein each R$^x$ and R$^y$ is independently optionally substituted C$_{1-12}$ alkyl. In another aspect of this embodiment, X³ is —OP(O)(CH$_3$)$_2$. In another aspect of this embodiment, X³ is —OP(O)R$^x$R$^y$ wherein each R$^x$ and R$^y$ is independently methyl, ethyl, or optionally substituted phenyl. In another aspect of this embodiment, X³ is —OP(O)R$^x$R$^y$ wherein each R$^x$ and R$^y$ is independently methyl or ethyl. In another aspect of this embodiment, X³ is —P(O)(OR$^x$)(OR$^y$). In another aspect of this embodiment, $X^3$ is —P(O)(OR$^x$)(OR$^y$) wherein each R$^x$ and R' is independently methyl or ethyl. In another aspect of this embodiment, $X^3$ is

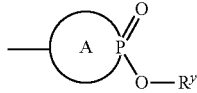

wherein each A is a 4 to 6 membered ring, including the depicted P atom. In another aspect of this embodiment, $X^3$ is

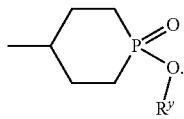

In another aspect of this embodiment, $X^3$ is

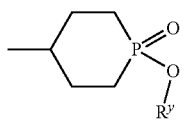

wherein R$^y$ is H or $C_{1-6}$ alkyl. In a preferred aspect of this embodiment, $R^2$ is

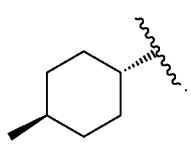 [SMILES: *[C@H]1CC[C@H](C)CC1]

In another preferred aspect of this embodiment, $R^2$ is

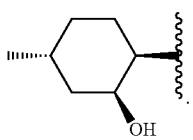 [SMILES: *[C@@H]1CC[C@@H](C)C[C@@H]1O]

In another preferred aspect of this embodiment, $R^2$ is

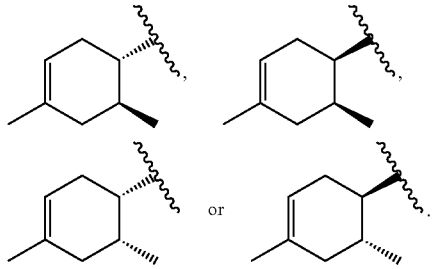

In another preferred aspect of this embodiment, $R^2$ is

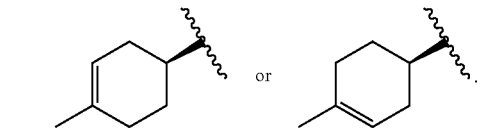

In another embodiment of Formula II, p is 1 and q is 2. In another aspect of this embodiment, $L^3$ is optionally substituted $C_{1-12}$ alkylene, optionally substituted $C_{2-12}$ alkenylene, optionally substituted $C_{2-12}$ alkynylene, optionally substituted $C_{3-12}$ cycloalkylene or optionally substituted 3-12 membered heterocyclylene. In another aspect of this embodiment, $L^3$ is optionally substituted $C_{3-12}$ cycloalkylene. In another aspect of this embodiment, $L^3$ is optionally substituted $C_{4-6}$ cycloalkylene. In another aspect of this embodiment, $L^3$ is optionally substituted cyclohexylene. In another aspect of this embodiment, $L^4$ is —NH—. In another aspect of this embodiment, $L^4$ is optionally substituted $C_{1-12}$ alkylene. In another aspect of this embodiment, one of $L^4$ is —NH— and the other $L^4$ is $C_{1-12}$ alkylene. In another aspect of this embodiment, -(L$^4$)$_2$- is —NH—$C_{1-6}$ alkylene. In another aspect of this embodiment, $X^3$ is —P(O)R$^x$R$^y$. In another aspect of this embodiment, $X^3$ is —P(O)R$^x$R$^y$ wherein each R$^x$ and R$^y$ is independently optionally substituted $C_{1-12}$ alkyl. In another aspect of this embodiment, $X^3$ is —P(O)R$^x$R$^y$ wherein each R$^x$ and R$^y$ is independently ethyl or methyl. In another aspect of this embodiment, $X^3$ is —P(O)OR$^x$R$^y$. In another aspect of this embodiment, $X^3$ is —P(O)OR$^x$R$^y$ wherein each R$^x$ and R$^y$ is independently optionally substituted $C_{1-12}$ alkyl. In another aspect of this embodiment, $X^3$ is —P(O)(OR$^x$)(CH$_3$). In another aspect of this embodiment, $X^3$ is —P(O)(OR$^x$)(CH$_3$) wherein R$^x$ is H or $C_{1-6}$ alkyl. In another aspect of this embodiment, $X^3$ is —OP(O)R$^x$R$^y$. In another aspect of this embodiment, $X^3$ is —OP(O)R$^x$R$^y$ wherein each R$^x$ and R$^y$ is independently optionally substituted $C_{1-12}$ alkyl. In another aspect of this embodiment, $X^3$ is —OP(O)(CH$_3$)$_2$. In another aspect of this embodiment, $X^3$ is —OP(O)R$^x$R$^y$ wherein each R$^x$ and R$^y$ is independently methyl, ethyl, or optionally substituted phenyl. In another aspect of this embodiment, $X^3$ is —OP(O)R$^x$R$^y$ wherein each R$^x$ and R$^y$ is independently methyl or ethyl. In another aspect of this embodiment, $X^3$ is —P(O)(OR$^x$)(OR$^y$). In another aspect of this embodiment, $X^3$ is —P(O)(OR$^x$)(OR$^y$) wherein each R$^x$ and R$^y$ is independently methyl or ethyl. In another aspect of this embodiment, $X^3$ is

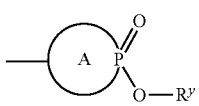

wherein each A is a 4 to 6 membered ring, including the depicted P atom. In another aspect of this embodiment, $X^3$ is

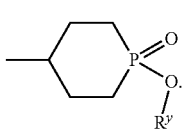

In another aspect of this embodiment, $X^3$ is

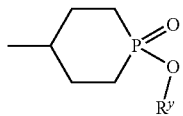

wherein $R^y$ is H or $C_{1-6}$ alkyl. In a preferred aspect of this embodiment, $R^2$ is

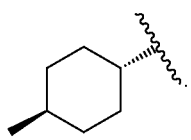

In another preferred aspect of this embodiment, $R^2$ is

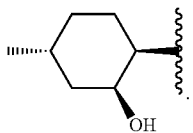 [SMILES: *[C@@H]1CC[C@@H](C)C[C@@H]1O]

In another preferred aspect of this embodiment, $R^2$ is

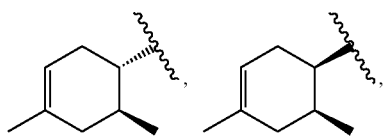

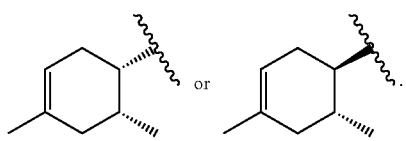

In another preferred aspect of this embodiment, $R^2$ is

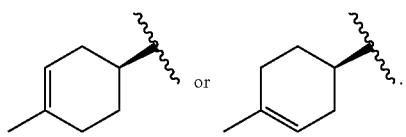

In another embodiment, the compound of Formula I is selected from the group consisting of

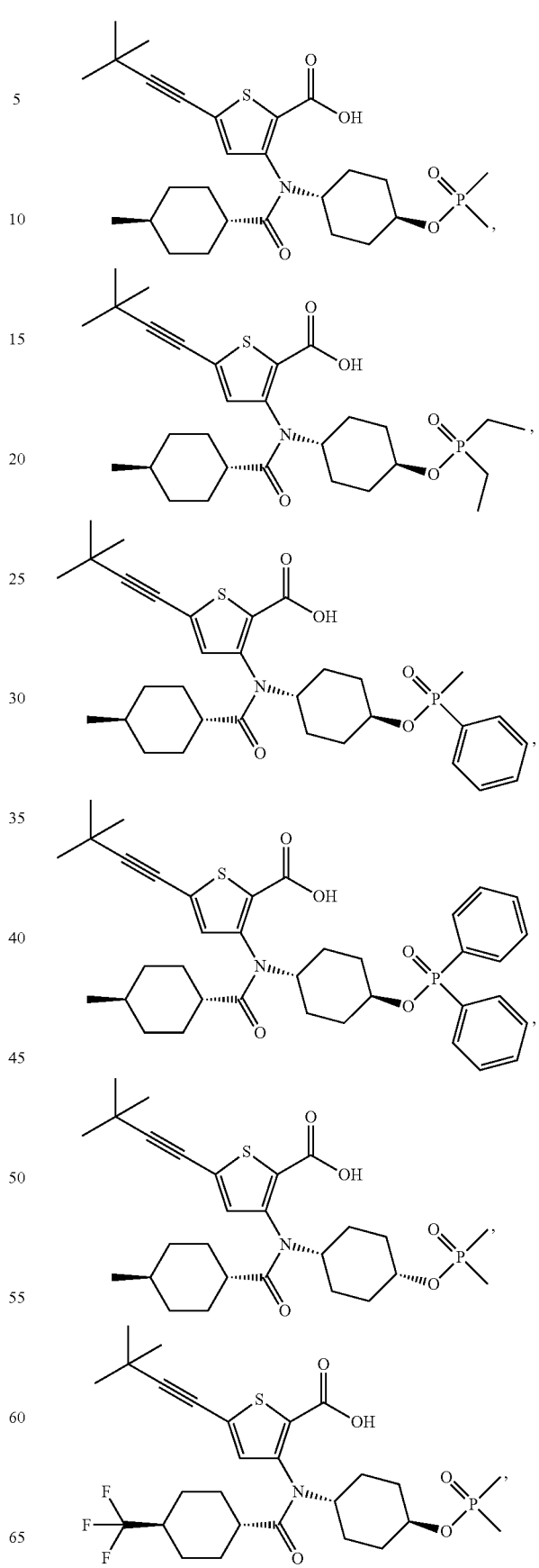

35
-continued
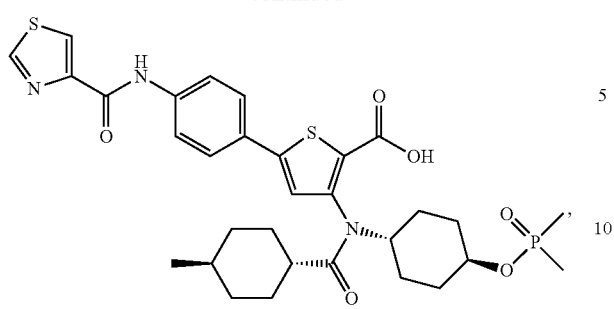
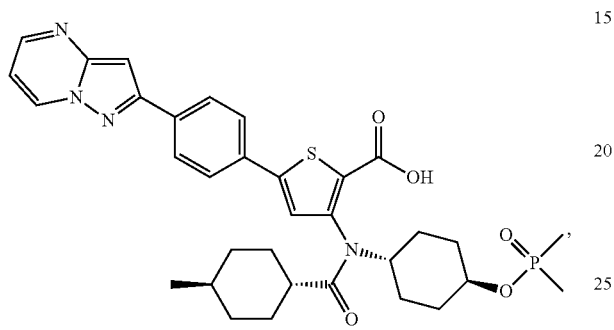
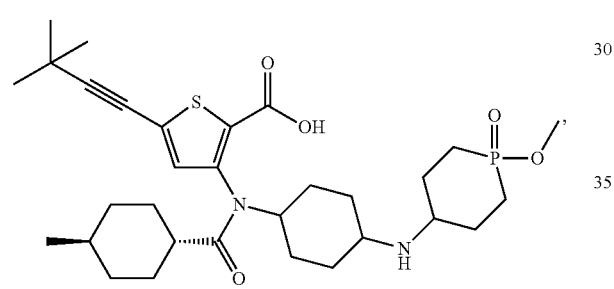
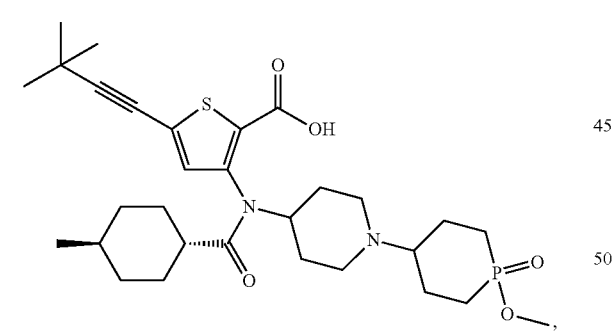
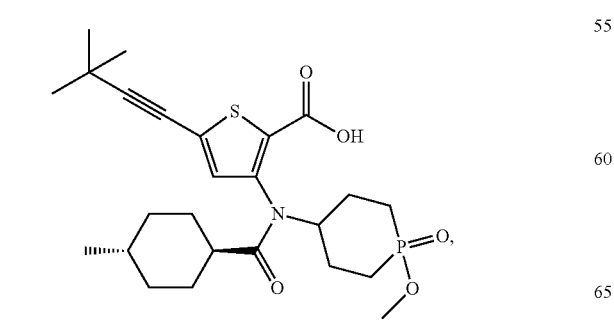
36
-continued
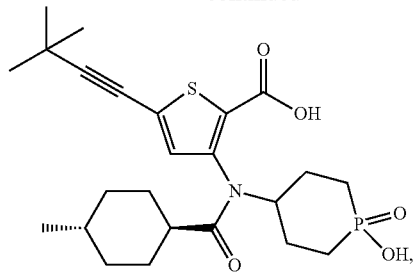
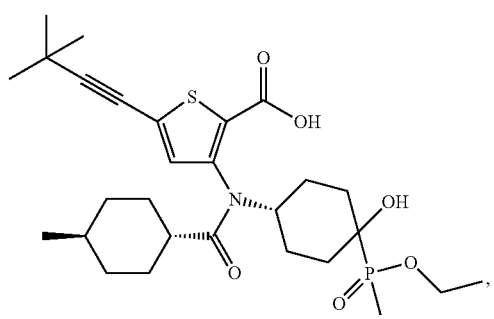
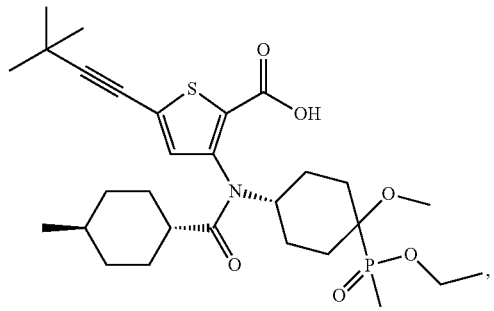
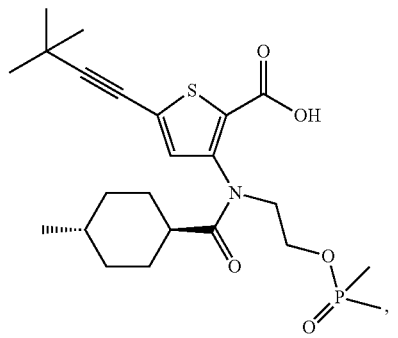
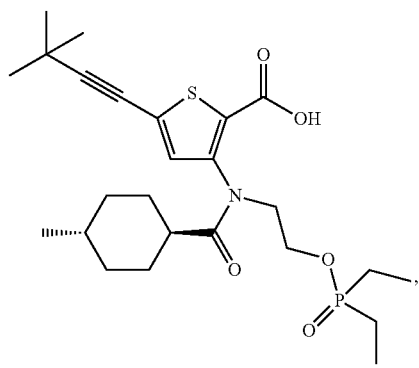

37
-continued
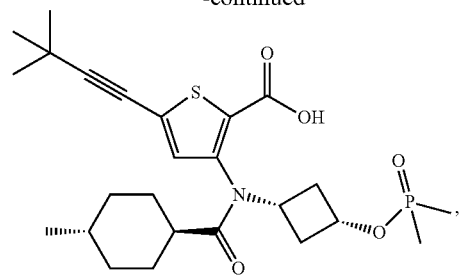
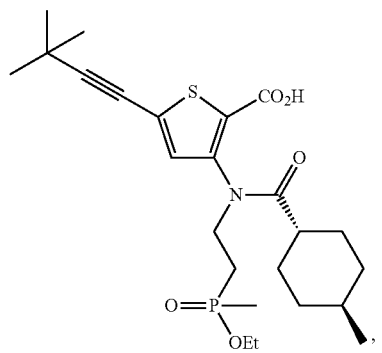
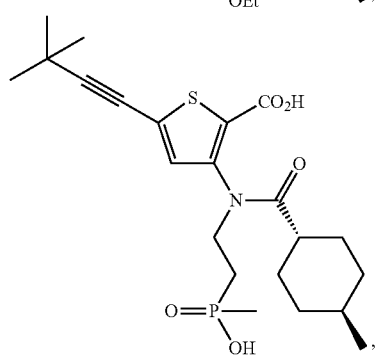
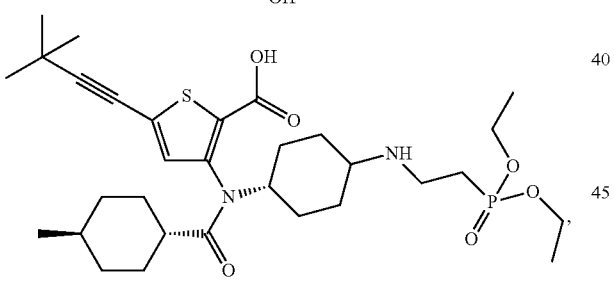
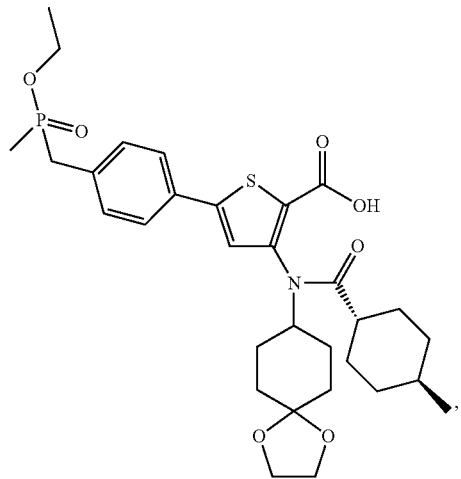
38
-continued
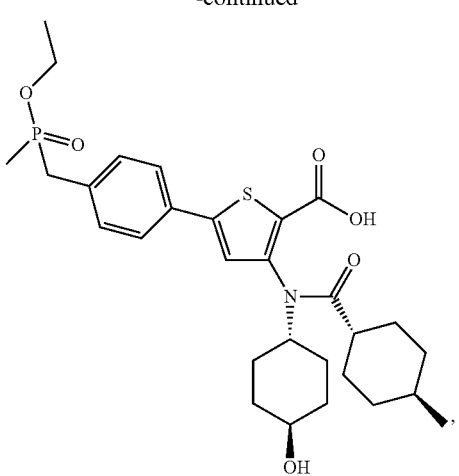
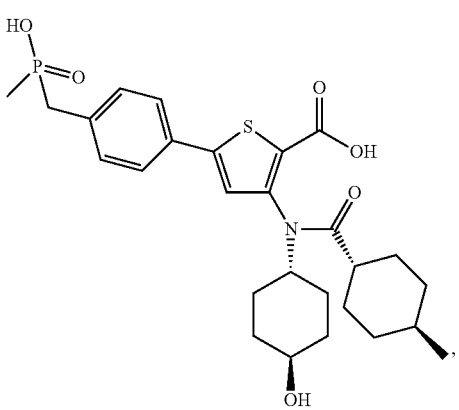
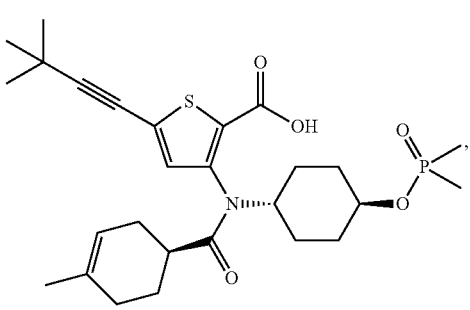
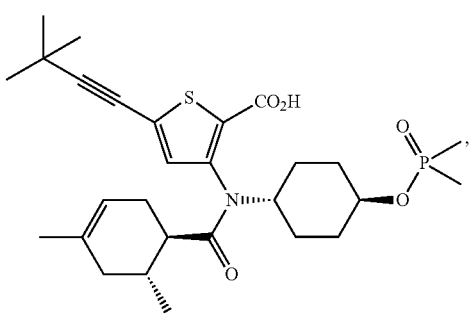

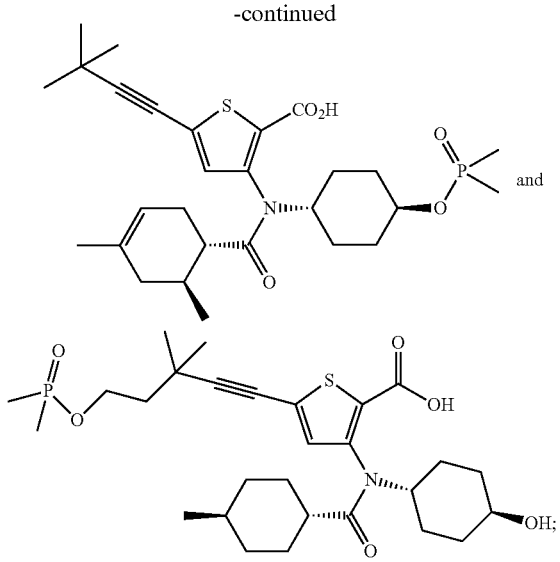

or a pharmaceutically acceptable salt or ester thereof.

All documents referenced herein are each incorporated by reference in their entirety for all purposes.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain radical or or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethylene (—$CH(CH_3)$—), 1,2-ethylene (—$CH_2CH_2$—), 1,1-propylene (—$CH(CH_2CH_3)$—), 1,2-propylene (—$CH_2CH(CH_3)$—), 1,3-propylene (—$CH_2CH_2CH_2$—), 1,4-butylene (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene propargyl (—C≡C—), propargyl (—$CH_2$C≡C—), and 4-pentynyl (—$CH_2CH_2CH_2$C≡C—).

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, phenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 6 ring atoms, still more typically 5 or 6 ring atoms. Bicyclic cycloalkyl groups have 7 to 12 ring atoms, e.g., arranged as a bicycle (4,5), (5,5), (5,6) or (6,6) system, or 9 or 10 ring atoms arranged as a bicycle (5,6) or (6,6) system. Cycloalkyl groups include hydrocarbon mono-, bi-, and poly-cyclic rings, whether fused, bridged, or Spiro. Non-limiting examples of monocyclic cycloalkyls include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl. Non-limiting examples of bicyclo cycloalkyls includes naphthyl, tetrahydronapthalene, decaline and bicyclo[3.1.0]hex-6-yl and the like.

"Cycloalkylene" refers to a cycloalkyl as defined above having two monovalent radical centers derived by the removal of two hydrogen atoms from the same or two different carbon atoms of a parent cycloalkyl. Typical cycloalkylene radicals include, but are not limited to, cyclopropylene, cyclobutylene, cyclopentylene and cyclohexylene.

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

"Heterocycle" or "heterocyclyl" refers to a saturated or partially saturated cyclic group having from 1 to 14 carbon atoms and from 1 to 6 heteroatoms selected from N, S, P, or O, and includes single ring and multiple ring systems including, fused, bridged, and Spiro ring systems. "Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs"* (John Wiley & Sons, New York, 1950 to present), in particular Volumes 13, 14, 16, 19, and 28; and J. Am. Chem. Soc. (1960) 82:5566. In one embodiment, the carbon, nitrogen, phosphorus, or sulfur atom(s) of the heterocyclic group may be oxidized to provide for C(=O), N-oxide, phosphinane oxide, sulfinyl, or sulfonyl moieties.

As one example, substituted heterocyclyls include, for example, heterocyclic rings substituted with any of the substituents disclosed herein including oxo groups. A non-limiting example of a carbonyl substituted heterocyclyl is:

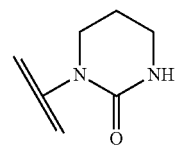

Examples of heterocycles include by way of example and not limitation dihydroypyridyl, tetrahydropyridyl (piperidyl), tetrahydrothiophenyl, sulfur oxidized tetrahydrothiophenyl, piperidinyl, 4-piperidonyl, pyrrolidinyl, azetidinyl, 2-pyrrolidonyl, tetrahydrofuranyl, decahydroquinolinyl, octahydroisoquinolinyl, pyranyl, morpholinyl, and bis-tetrahydrofuranyl:

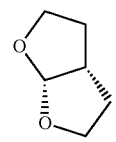

"Heterocyclene" or "heterocyclylene" refers to a "heterocycle" or "heterocyclyl" as defined above having two monovalent radical centers derived by the removal of two hydrogen atoms from the same or two different carbon atoms of a parent heterocycle, the removal of two hydrogen atoms from two nitrogen atoms of a parent heterocycle, or the removal of a hydrogen atom from a nitrogen and the removal of a hydrogen atom from a carbon atome of a parent heterocycle. Non-limiting examples of heterocyclene or heterocyclylenes are:

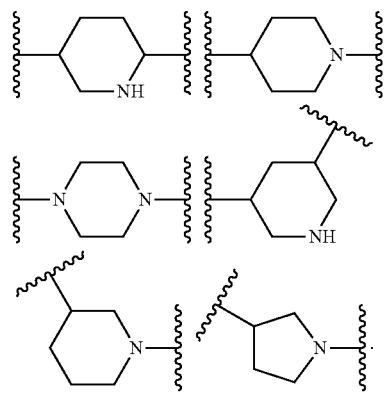

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorus. For multiple ring systems, by way of example, the term "heteroaryl" includes fused, bridged, and spiro ring systems having aromatic and non-aromatic rings. In one embodiment, the carbon, nitrogen, or sulfur ring atom(s) of the heteroaryl group may be oxidized to provide for C(=O), N-oxide, sulfinyl, or sulfonyl moieties.

Examples of heteroaryls include by way of example and not limitation pyridyl, thiazolyl, pyrimidinyl, furanyl, thienyl, pyrrolyl, pyrazolyl, imidazolyl, tetrazolyl, benzofuranyl, thianaphthalenyl, indolyl, quinolinyl, isoquinolinyl, benzimidazolyl, tetrahydroquinolinyl, tetrahydroisoquinolinyl, 6H-1,2,5-thiadiazinyl, 2H,6H-1,5,2-dithiazinyl, thienyl, thianthrenyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. "Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclylalkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms and 1-6 heteroatoms, e.g., the alkyl portion of the heterocyclylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, phosphorus, and/or nitrogen containing heterocycles such as pyrrolidiylmethyl, 2-tetrahydrofuranylylethan-1-yl, and the like, 6-membered sulfur, oxygen, and/or nitrogen containing heterocycles such as piperidinylmethyl, morpholinylmethyl, piperidinylethyl, teterahydropyranylethyl, and the like.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$—oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, and the like.

The term "heterocyclyloxy" represents a heterocyclyl group attached to the adjacent atom by an oxygen.

When there is a sulfur atom present, the sulfur atom can be at different oxidation levels, namely, S, SO, $SO_2$, or $SO_3$. All such oxidation levels are within the scope of the present invention.

When there is a phosphorus atom present, the phosphorus atom can be at different oxidation levels, namely, $POR^aR^bR^c$, $PO_2R^aR^b$, or $PO_3R^aR^b$, where Fr, $R^b$, and $R^c$ each independently is chosen from H, $C_{1-12}$ alkyl, $C_{2-12}$ alkenyl, $C_{2-12}$ alkynyl, $C_{6-14}$ aryl, 3-12 membered heterocycle, 3-18 membered heteroarylalkyl, $C_{6-18}$ arylalkyl; or two taken together (with or without oxygens) form a 5 to 10 membered heterocycle. All such oxidation levels are within the scope of the present invention The term "optionally substituted" in reference to a particular moiety of the compound of Formula I-II (e.g., an optionally substituted aryl group) refers to a moiety wherein all substiutents are hydrogen or wherein one or more of the hydrogens of the moiety may be replaced by substituents such as those listed under the definition of "substituted" or as otherwise specified.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Divalent groups may also be similarly substituted. Unless otherwise indicated, typical substituents include, but are not limited to, —X, —$R^b$, —O, =O, —$OR^b$, —$SR^b$, —$S^-$, —$NR^b{}_2$, —$N^+R^b{}_3$, =$NR^b$, —$CX_3$, —CN, —OCN, —SCN, —N=C=O, —NCS, —NO, —$NO_2$, =$N_2$, —$N_3$, —NHC(=O)$R^b$, —OC(=O)$R^b$, —NHC(=O)$NR^b{}_2$, —S(=O)$_2$—, —S(=O)$_2$OH, —S(=O)$_2R^b$, —OS(=O)$_2OR^b$, —S(=O)$_2NR^b{}_2$, —S(=O)$R^b$, —OP(=O)(O$R^b$)$_2$, —P(=O)(O$R^b$)$_2$, —P(=O)(O$^-$)$_2$, —P(=O)(OH)$_2$, —P(O)(O$R^b$)(O$^-$), —C(=O)$R^b$, —C(=O)X, —C(S)$R^b$, —C(O)O$R^b$, —C(O)O$^-$, —C(S)O$R^b$, —C(O)S$R^b$, —C(S)S$R^b$, —C(O)N$R^b{}_2$, —C(S)N$R^b{}_2$, —C(=N$R^b$)N$R^b{}_2$, where each X is independently a halogen: F, Cl, Br, or I; and each $R^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc.

are understood to be interchangeable with "alkylene", "arylene", "heterocyclylene", etc.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. In addition, the scope of the present invention includes prodrug forms of the compound herein described.

A compound of Formula I-II and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of Formula I-II and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-II and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to stereoisomers of a compound which are non-superimposable mirror images of one another.

"Atropisomers" refer to stereoisomers of a compound resulting from hindered rotation about single bonds where the steric strain barrier to rotation is high enough to allow for the isolation of the individual conformer. Atropisomers display axial chirality. Atropisomers may be equilibrated thermally and the interconversion barrier may be measured kinetically. Atropisomerism may occur apart from the presence of other forms of chiral isomerism. Thus, as illustrated, the depicted nitrogen atom is planar and compound of Formula I is capable of existing as atropisomers:

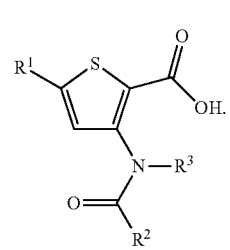

(I)

In one embodiment of the present invention, the compounds exist in a conformeric form of Formula Ia:

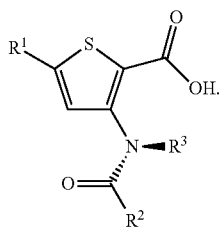

(Ia)

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The modifier "about" used in connection with a quantity is inclusive of the stated value and has the meaning dictated by the context (e.g., includes the degree of error associated with measurement of the particular quantity).

Whenever a compound described herein is substituted with more than one of the same designated group, e.g., "R" or "$R^1$", then it will be understood that the groups may be the same or different, i.e., each group is independently selected. Wavy lines,

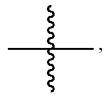

indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I-II may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The compounds of Formula I-II also include molecules that incorporate isotopes of the atoms specified in the particular molecules. Non-limiting examples of these isotopes include D, T, $^{14}C$, $^{13}C$ and $^{15}N$.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

In yet another-embodiment, the present application discloses pharmaceutical compositions comprising a compound of Formula I or a pharmaceutically acceptable salt thereof, and a pharmaceutically acceptable carrier or exipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034 SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

As will be appreciated by those skilled in the art, when treating a viral infection such as HCV, such treatment may be characterized in a variety of ways and measured by a variety of endpoints. The scope of the present invention is intended to encompass all such characterizations.

SYNTHETIC EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac₂O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH⁺ | mass plus 1 |
| MH⁻ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |

TABLE 1-continued

List of abbreviations and acronyms.

| Abbreviation | Meaning |
|---|---|
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

General Schemes I

The compounds of this invention may be synthesized by routes with key bond-forming steps as indicated in Scheme A, below, in which the carboxylate substituent "R" indicates either a protecting group such as an alkyl ester (where applicable), or the free acid itself. Alkyl ester protecting groups are conveniently removed by saponification with an alkali metal hydroxide in a protic solvent such as water or an alcohol, and may be facilitated by use of ethereal solvent mixtures and/or heating. Alternatively they may be removed by dealkylation through heating with an alkali metal halide in an aprotic solvent. Similar manipulations may be performed on phosphinate-contaning intermediates. As a non-limiting example, phosphinoyl esters are conveniently dealkylated by heating with a Lewis acid such as iodotrimethylsilane, optionally in the presence of a base such as 2,6-dimethyl lutidine and an inert aprotic solvent such as acetonitrile.

When $X^3$ indicates a group that is attached to $L^3$ or $L^4$ via a phosphorus atom, $R^3$ may conveniently be introduced via reductive amination using a phosphorus-containing carbonyl reagent together with an appropriate 3-aminothiophene, and mediated by a reducing agent such as phenylsilane in the presence of a Lewis acid such as dibutyl tin dichloride in an inert ethereal solvent. Alternatively the intermediate secondary amine may be generated by coupling of a phosphorus-containing primary amine with a 3-halothiophene in a reaction that may be catalyzed by Pd (*J. Org. Chem.*, 2000, 65, 1158-1174, herein incorporated by reference with regard to such synthesis). The amine is then converted to the amide by acylation with a carboxylic acid derivative such as an acyl chloride or anhydride in the presence of a base such as pyridine or a tertiary amine in an inert solvent such as dichloromethane.

Scheme A

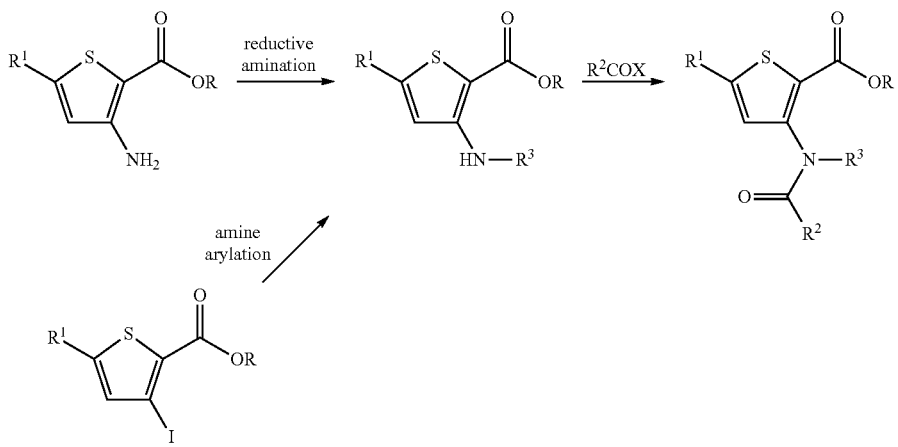

In other cases it is convenient to perform synthetic manipulations on the side chain R³ with the rest of the molecule fully assembled. Thus, for example, if L³ is to contain a secondary amine, reductive amination with a phosphorus-containing aldehyde or ketone in the presence of a reducing agent, such as sodium triacetoxyborohydride or sodium cyanoborohydride, in a dipolar aprotic solvent generates the desired target molecule directly. Alternatively, if the phosphorus atom is connected to L³ or L⁴ via an oxygen atom (as when X³ is group c)), the requisite alcohol may be treated with a phosphinoyl chloride reagent in the presence of a tertiary amine base. On the other hand, if the phosphorus atom is connected via a carbon atom bearing a hydroxyl group, the high nucleophilicity of phosphinates may be exploited to generate the desired C—P bond through addition to a carbonyl group.

Experimentals

Example 1

Compound 1: 5-(3,3-Dimethyl-but-1-ynyl)-3-[[trans-4-(dimethyl-phosphinoyloxy)-cyclohexyl]-(trans-4-methyl-cyclohexanecarbonyl)-amino]-thiophene-2-carboxylic acid

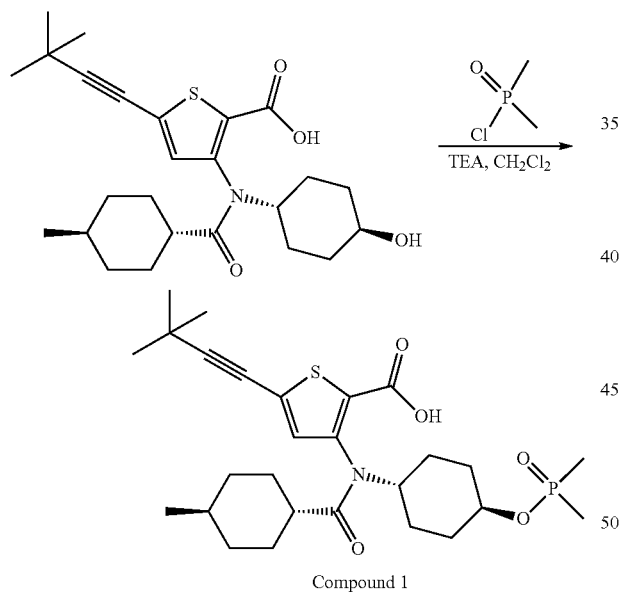

Compound 1

A mixture of 5-(3,3-dimethyl-but-1-ynyl)-3-[(trans-4-hydroxy-cyclohexyl)-(trans-4-methyl-cyclohexanecarbonyl)-amino]-thiophene-2-carboxylic acid (100 mg, 0.224 mmol) and triethylamine (278 μL, 2.02 mmol) in DCM (1 mL) at 0° C. was treated with dimethylphosphinic chloride (150 mg, 1.34 mmol) in two portions. The mixture was warm to room temperature and stirred for several hours.

Ethyl acetate and water was added and the aqueous layer was carefully quenched with citric acid (10% aqueous solution, 2-3 mL). The mixture was extracted with ethyl acetate (2×30 mL). The combined organic layers were dried over sodium sulfate, filtered and concentrated. The residue was purified by RP HPLC using a C18 column with a gradient of 0.1% TFA-H₂O, 0.1% TFA-acetonitrile, to provide 70 mg (60%) of desired product. MS (m/z) 522.2 [M+H]⁺; HPLC retention time: 4.32 min (2-98% acetonitrile:water with 0.05% trifluoroacetic acid).

Example 2

Compound 2: 3-[[trans-4-(Diethyl-phosphinoyloxy)-cyclohexyl]-(trans-4-methyl-cyclohexanecarbonyl)-amino]-5-(3,3-dimethyl-but-1-ynyl)-thiophene-2-carboxylic acid

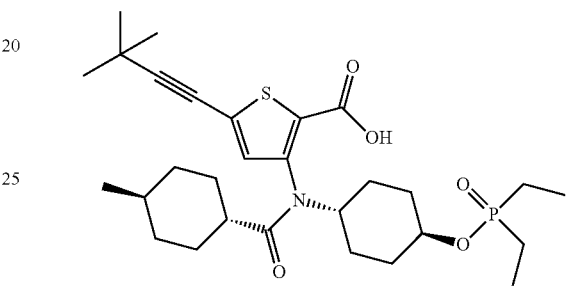

Compound 2

The title compound was synthesized in a manner analogous to Example 1, using diethylphosphinic chloride in place of dimethylphosphinic chloride. MS (m/z): 550.3 [M+H]⁻; HPLC retention time: 4.77 min (2-98% acetonitrile:water with 0.05% trifluoroacetic acid).

Example 3

Compound 3: 5-(3,3-Dimethyl-but-1-ynyl)-3-{(trans-4-methyl-cyclohexanecarbonyl)-[trans-4-(methyl-phenyl-phosphinoyloxy)-cyclohexyl]-amino}thiophene-2-carboxylic acid

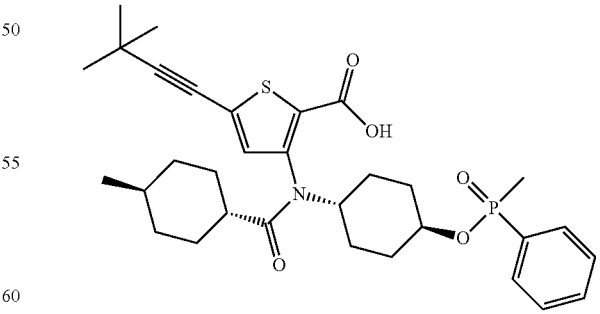

Compound 3

The title compound was synthesized in a manner analogous to Example 1, using methylphenylphosphinic chloride in place of dimethylphosphinic chloride: MS (m/z): 584.3 [M+H]⁻; HPLC retention time: 4.99 min (2-98% acetonitrile:water with 0.05% trifluoroacetic acid).

Example 4

Compound 4: 5-(3,3-Dimethyl-but-1-ynyl)-3-[[(trans-4-(diphenyl-phosphinoyloxy)-cyclohexyl]-(trans-4-methyl-cyclohexanecarbonyl)-amino]-thiophene-2-carboxylic acid Compound 4

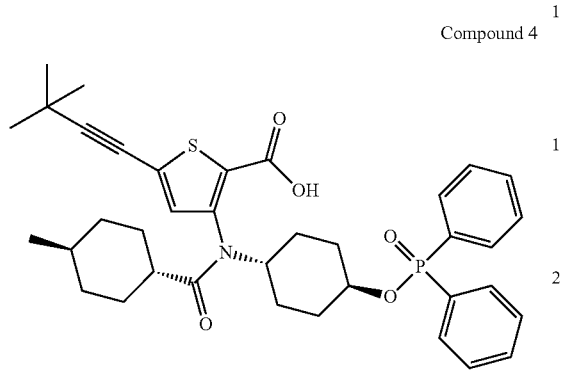

The title compound was synthesized in a manner analogous to Example 1, using diphenylphosphinic chloride in place of dimethylphosphinic chloride: MS (m/z): 646.3 [M+H]⁻; HPLC retention time: 5.47 min (2-98% acetonitrile:water with 0.05% trifluoroacetic acid).

Example 5

Compound 5: 5-(3,3-Dimethyl-but-1-ynyl)-3-[[cis-4-(dimethyl-phosphinoyloxy)-cyclohexyl]-(trans-4-methyl-cyclohexanecarbonyl)-amino]-thiophene-2-carboxylic acid Compound 5

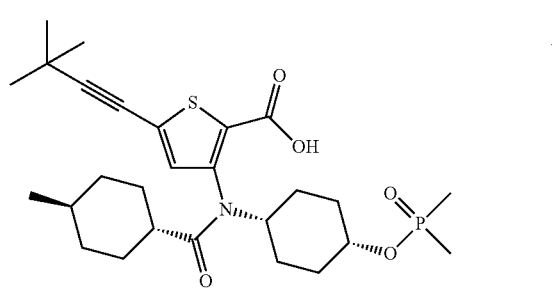

The title compound was synthesized in a manner analogous to Example 1, using 5-(3,3-Dimethyl-but-1-ynyl)-3-[(cis-4-hydroxy-cyclohexyl)-(trans-4-methyl-cyclohexanecarbonyl)-amino]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid. MS (m/z): 522.2 [M+H]⁻; HPLC retention time: 4.31 min (2-98% acetonitrile:water with 0.05% trifluoroacetic acid).

Example 6

Compound 6: 5-(3,3-Dimethyl-but-1-ynyl)-3-[[trans-4-(dimethyl-phosphinoyloxy)-cyclohexyl]-(trans-4-trifluoromethyl-cyclohexanecarbonyl)-amino]-thiophene-2-carboxylic acid Compound 6

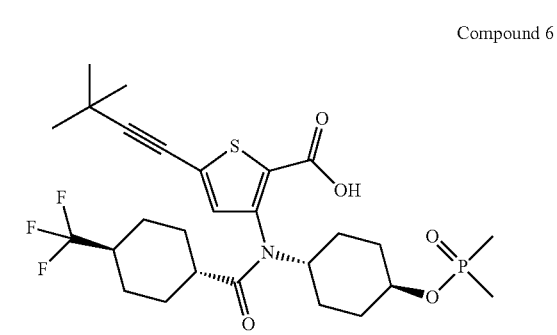 [SMILES: CC(C)(C)C#Cc1cc(N(C(=O)[C@H]2CC[C@H](C(F)(F)F)CC2)[C@H]2CC[C@H](OP(C)(C)=O)CC2)c(C(=O)O)s1]

The title compound was synthesized in a manner analogous to Example 1, using 5-(3,3-Dimethyl-but-1-ynyl)-3-[(trans-4-hydroxy-cyclohexyl)-(trans-4-trifluoromethyl-cyclohexanecarbonyl)-amino]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid. MS (m/z): 576.2 [M+H]⁻; HPLC retention time: 4.15 min (2-98% acetonitrile:water with 0.05% trifluoroacetic acid).

Example 7

Compound 7: 3-[[trans-4-(Dimethyl-phosphinoyloxy)-cyclohexyl]-(trans-4-methyl-cyclohexanecarbonyl)-amino]-5-{4[(thiazole-4-carbonyl)-amino]-phenyl}-thiophene-2-carboxylic acid Compound 7

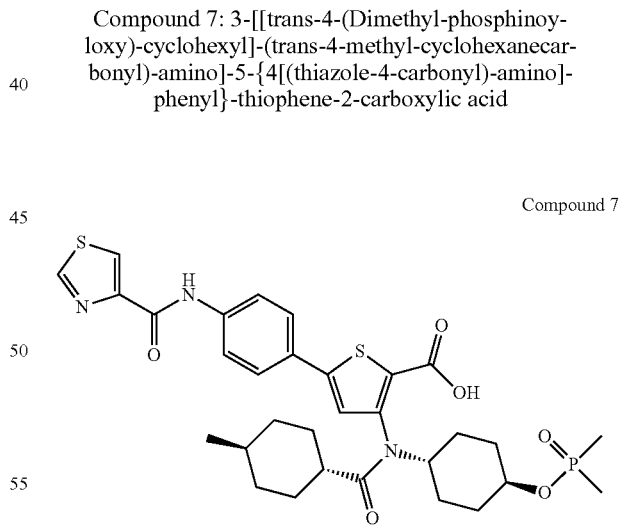

The title compound was synthesized in a manner analogous to Example 1, using 3-[(trans-4-Hydroxy-cyclohexyl)-(trans-4-methyl-cyclohexanecarbonyl)-amino]-5-{4-[(thiazole-4-carbonyl)-amino}-phenyl]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid: MS (m/z): 644.2 [M+H]⁻; HPLC retention time: 3.62 min (2-98% acetonitrile:water with 0.05% trifluoroacetic acid).

Example 8

Compound 8: 3-[[trans-4-(Dimethyl-phosphinoyloxy)-cyclohexyl]-(trans-4-methyl-cyclohexanecarbonyl)-amino]-5-(4-pyrazolo[1,5-a]pyrimidin-2-yl-phenyl)-thiophene-2-carboxylic acid Compound 8

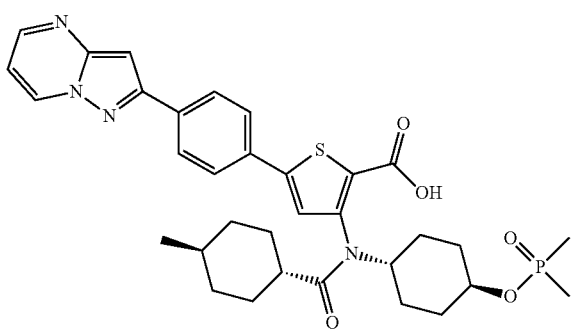

The title compound was synthesized in a manner analogous to Example 1, using 3-[(trans-4-Hydroxy-cyclohexyl)-(trans-4-methyl-cyclohexanecarbonyl)-amino]-5-(4-pyrazolo[1,5-a]pyrimidin-2-yl-phenyl)-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]thiophene-2-carboxylic acid: MS (m/z): 635.3 [M+H]⁻; HPLC retention time: 3.76 min (2-98% acetonitrile:water with 0.05% trifluoroacetic acid).

Example 9

Compound 9: 5-(3,3-Dimethyl-but-1-ynyl)-3-[[4-(1-methoxy-1-oxo-1λ⁵-phosphinan-4-ylamino)-cyclohexyl]-(trans-4-methyl-cyclohexanecarbonyl)-amino]-thiophene-2-carboxylic acid Scheme 2

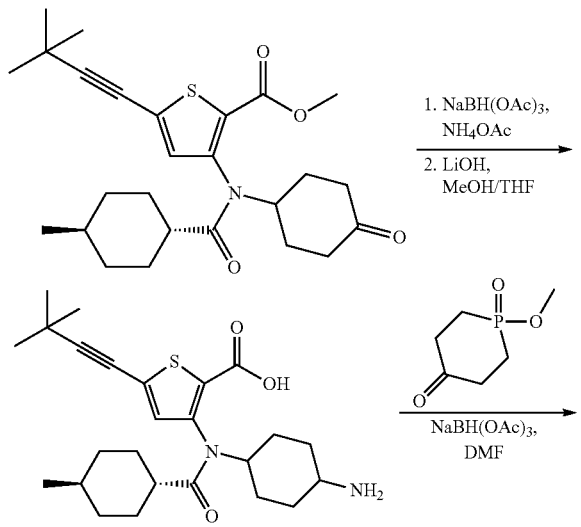

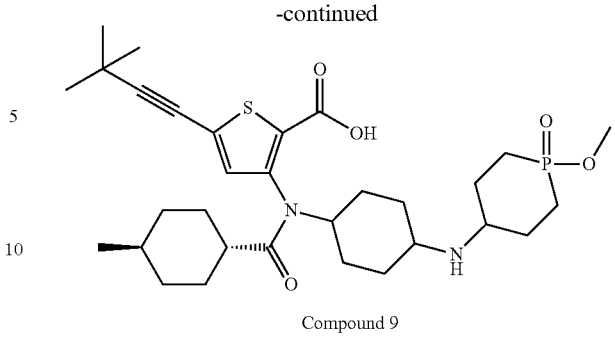

Compound 9

Synthesis of 3-(N-(4-aminocyclohexyl)-(trans-4-ethylcyclohexane carboxamido)-5-(3,3-dimethylbut-1-ynyl)thiophene-2-carboxylic acid hydrochloride To the mixture of methyl 5-(3,3-dimethylbut-1-ynyl)-3-(4-methyl-N-(4-oxocyclohexyl)cyclohexanecarboxamido)thiophene-2-carboxylate (440 mg, 1 mmol), ammonium acetate (745 mg, 10 mmol) and sodium sulfate (250 mg) in methanol was added sodium triacetoxyborohydride (424 mg, 2 mmol). The reaction mixture was stirred at room temperature for 2 h. Sodium sulfate was removed by filtration and the filtrate was diluted with ethyl acetate, washed with saturated sodium bicarbonate and brine. The organic layer was dried over magnesium sulfate, filtered and concentrated. The residue was purified by HPLC (Gemini column; 5% acetonitrile:water, 5 min; 5-100% acetonitrile:water, 18 min; 100% acetonitrile, 6 min; both solvents containing 0.1% trifluoroacetic acid). The combined fractions were concentrated, basified and extracted with EtOAc. The organic layer was dried over magnesium sulfate, filtered and concentrated to give title compound (230 mg): MS (m/z): 459.3 [M+H]

Methyl 3-(N-(4-aminocyclohexyl)-(trans-4-methylcyclohexane carboxamide)-5-(3,3-dimethylbut-1-ynyl)thiophene-2-carboxylate (138 mg, 0.3 mmol) was dissolved in 4 mL of methanol and 2 mL of THF, and to the solution was added 2 mL of 1N LiOH. The reaction mixture was stirred at room temperature for 2 h. Volatiles were removed under vacuum and the residue was acidified to pH3 using 0.5 N HCl and then partitioned between ethyl acetate and water. The organic layer was dried over magnesium sulfate, filtered and concentrated to give title compound (126 mg): MS (m/z): 445.2 [M+H]

Synthesis of 5-(3,3-Dimethyl-but-1-ynyl)-3-[[4-(1-methoxy-1-oxo-1λ⁵-phosphinan-4-ylamino)-cyclohexyl]-(trans-4-methyl-cyclohexanecarbonyl)-amino]-thiophene-2-carboxylic acid 3-(N-(4-aminocyclohexyl)-4-methylcyclohexanecarboxamido)-5-(3,3-dimethylbut-1-ynyl)thiophene-2-carboxylic acid hydrochloride (40 mg, 0.083 mmol) and 1-methoxy-1-oxo-1λ⁵-phosphinan-4-one (27 mg, 0.166 mmol) were dissolved in 2 mL of DMF. Sodium triacetoxyborohydride (35 mg, 0.166 mmol) was added. The reaction mixture was allowed to stir at room temperature over 18 hours, and then diluted with EtOAc, washed with saturated sodium bicarbonate and brine. The organic layer was dried over magnesium sulfate, filtered and concentrated. The residue was purified by HPLC (Gemini column; 5% acetonitrile:water, 5 min; 5-100% acetonitrile:water, 18 min; 100% acetonitrile, 6 min; both solvents containing 0.1% trifluoroacetic acid) to give title compound (38.6 mg): MS (m/z): 591.3 [M+H]⁻; HPLC retention time: 3.28 min (2-98% acetonitrile:water with 0.05% trifluoroacetic acid).

Example 10

Compound 10: 5-(3,3-Dimethyl-but-1-ynyl)-3-[[1-(1-methoxy-1-oxo-1λ⁵-phosphinan-4-yl)-piperidin-4-yl]-(trans-4-methyl-cyclohexanecarbonyl)-amino]-thiophene-2-carboxylic acid Compound 10

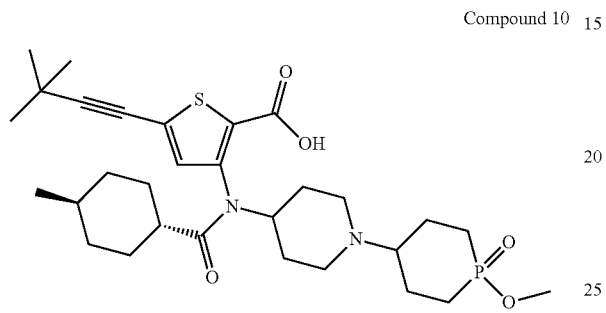

The title compound was synthesized in a manner analogous to Example 9, using 5-(3,3-dimethyl-but-1-ynyl)-3-[(trans-4-methyl-cyclohexanecarbonyl)-piperidin-4-yl-amino]-thiophene-2-carboxylic acid in place of 3-[(4-Amino-cyclohexyl)-(trans-4-methyl-cyclohexanecarbonyl)-amino]-5-(3,3-dimethyl-but-1-ynyl)-thiophene-2-carboxylic acid: MS (m/z): 577.1 [M+H]⁻; HPLC retention time: 3.46 min (2-98% acetonitrile:water with 0.05% trifluoroacetic acid).

Example 11

Compound 11: 5-(3,3-Dimethyl-but-1-ynyl)-3-[(1-methoxy-1-oxo-1λ⁵phosphinan-4-yl)-(trans-4-methyl-cyclohexanecarbonyl)-amino]-thiophene-2-carboxylic acid Scheme 3

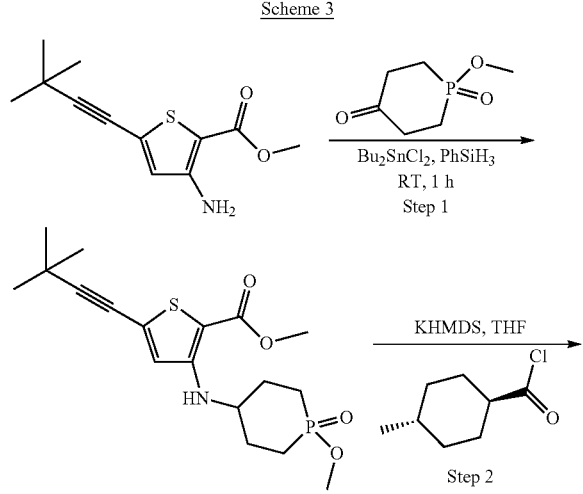

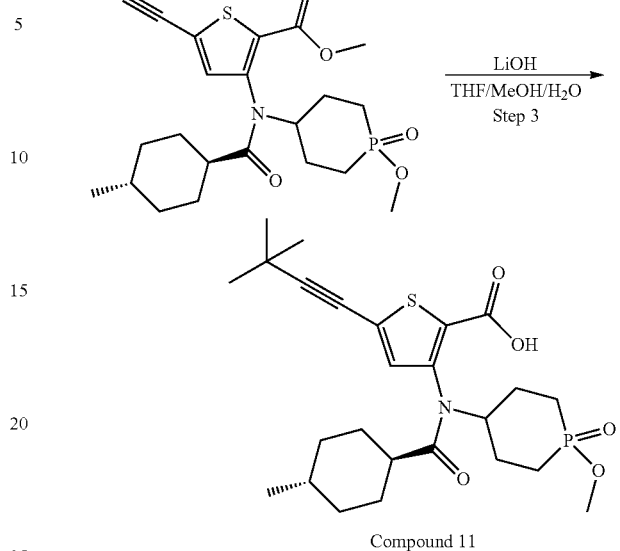

Compound 11

Step 1: Synthesis of Methyl 5-(3,3-Dimethyl-but-1-ynyl)-3-(1-methoxy-1-oxo-1λ⁵phosphinan-4-ylamino)-thiophene-2-carboxylate A solution of methyl 3-amino-5-(3,3-dimethylbut-1-ynyl) thiophene-2-carboxylate (474 mg, 2 mmol) and 1-Methoxy-1-oxo-1λ⁵ phosphinan-4-one (390 mg, 2.4 mmol) in THF (1 mL) and DMF (1 mL) was treated with dibutyltin dichloride (60 mg, 0.2 mmol). After 5 min, phenylsilane (272 µL, 2.2 mmol) was added, and the mixture was stirred for one hour at room temperature and then partitioned between water and ethyl acetate. The aqueous phase was extracted with ethyl acetate. The combined organic layers were washed with 5% LiCl and brine, dried over magnesium sulfate, filtered and concentrated. The residue was purified by silica gel column chromatography using EtOAc:Hexanes as eluent to provide 650 mg (85%) of title compound: MS (m/z) 384.0 [M+H]⁻; HPLC retention time: 4.463 min (2-98% acetonitrile:water with 0.05% trifluoroacetic acid).

Step 2: Synthesis of methyl 5-(3,3-Dimethyl-but-1-ynyl)-3-[(1-methoxy-1-oxo-1λ⁵-phosphinan-4-yl)-(trans-4-methyl-cyclohexanecarbonyl)-amino]-thiophene-2-carboxylate Methyl 5-(3,3-Dimethyl-but-1-ynyl)-3-[(1-methoxy-1-oxo-1λ⁵phosphinan-4-yl)-(4-methyl-cyclohexanecarbonyl)-amino]-thiophene-2-carboxylate (420 mg, 1.1 mmol) was dissolved in 2 mL of THF and cooled to −78° C. with a dry ice-acetone bath. A solution of KHMDS (2.6 mL, 0.5 M in toluene) was added slowly, and the mixture was stirred for 5 min. Trans-4-methylcyclohexanecarbonyl chloride (210 mg, 1.3 mmol) was added dropwise and stirring was continued at −78° C. for a further 5 min. The mixture was then allowed to warm to room temperature. The reaction mixture was cooled to 0° C. and quenched with saturated aqueous NH₄Cl, and then partitioned between water and ethyl acetate. The aqueous phase was extracted with ethyl acetate. The combined organic layers were washed with brine, dried over magnesium sulfate, filtered and concentrated. The residue was purified by silica gel column chromatography using 10% MeOH in EtOAc: Hexanes as eluent and then further purified by HPLC (Gemini column; 5% acetonitrile:water, 5 min; 5-100% acetonitrile:water, 18 min; 100% acetonitrile, 6 min; both solvents containing 0.1% trifluoroacetic acid), resulting in the title compound (37 mg) and recovered starting material (210 mg). MS (m/z): 508.2 [M+H]+; HPLC retention time: 4.949 min (2-98% acetonitrile:water with 0.05% trifluoroacetic acid).

Step 3: Synthesis of 5-(3,3-Dimethyl-but-1-ynyl)-3-[(1-methoxy-1-oxo-1λ$^5$-phosphinan-4-yl)-(trans-4-methyl-cyclohexanecarbonyl)-amino]-thiophene-2-carboxylic acid 5-(3,3-Dimethyl-but-1-ynyl)-3-[(1-methoxy-1-oxo-1λ$^5$-phosphinan-4-yl)-(trans-4-methyl-cyclohexanecarbonyl)-amino]-thiophene-2-carboxylate (36 mg, 0.07 mmol) was dissolved in 1 mL of methanol and 1 mL of THF, and to the solution was added 0.2 mL of 1N LiOH. The reaction mixture was stirred at room temperature for 5 hours, and then cooled to 0° C. and neutralized with 0.4 mL of 0.5 N HCl. After removal of solvent, the residue was purified by HPLC (Gemini column; 5% acetonitrile:water, 5 min; 5-100% acetonitrile:water, 18 min; 100% acetonitrile, 6 min; both solvents containing 0.1% trifluoroacetic acid), resulting in 20 mg (57%) of the title compound. MS (m/z): 494.2 [M+H]−; HPLC retention time: 4.144 min (2-98% acetonitrile:water with 0.05% trifluoroacetic acid).

Example 12

Compound 12: 5-(3,3-Dimethyl-but-1-ynyl)-3[(1-hydroxy-1-oxo-1λ$^5$phosphinan-4-yl)-(trans-4-methyl-cyclohexanecarbonyl)-amino]-thiophene-2-carboxylic acid

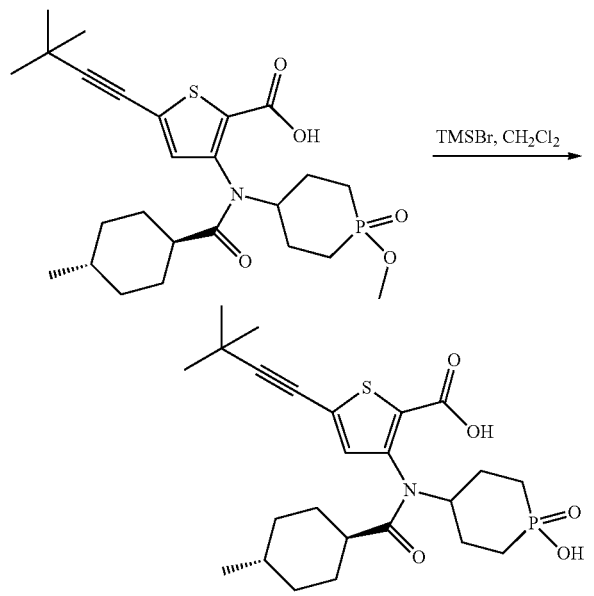

Compound 12

5-(3,3-Dimethyl-but-1-ynyl)-3-[(1-methoxy-1-oxo-1λ$^5$-phosphinan-4-yl)-(trans-4-methyl-cyclohexanecarbonyl)-amino]-thiophene-2-carboxylic acid (10 mg, 0.02 mmol) was dissolved in 1 mL of CH$_2$Cl$_2$, and to the solution was added TMSBr (26 µL, 0.2 mmol). The reaction mixture was stirred at room temperature for 40 minutes. Another portion of TMSBr (26 µL, 0.2 mmol) was added and the mixture was stirred at room temperature for 5 hours before cooling to 0° C. and quenching through the addition of methanol (0.5 ml). The solvent was removed under vacuum and the residue was purified by HPLC (Gemini column; 5% acetonitrile:water, 5 min; 5-100% acetonitrile:water, 18 min; 100% acetonitrile, 6 min; both solvents containing 0.1% trifluoroacetic acid). This resulted in 6 mg (62%) of the title compound. MS (m/z): 480.2 [M+H]+; HPLC retention time: 3.831 min (2-98% acetonitrile:water with 0.05% trifluoroacetic acid).

Example 13

Compound 13: 5-(3,3-dimethylbut-1-ynyl)-3-((1r,4r)-N-(4-ethoxy(methyl)phosphoryl)-4-hydroxycyclohexyl)-(trans-4-methylcyclohexanecarboxamido) thiophene-2-carboxylic acid

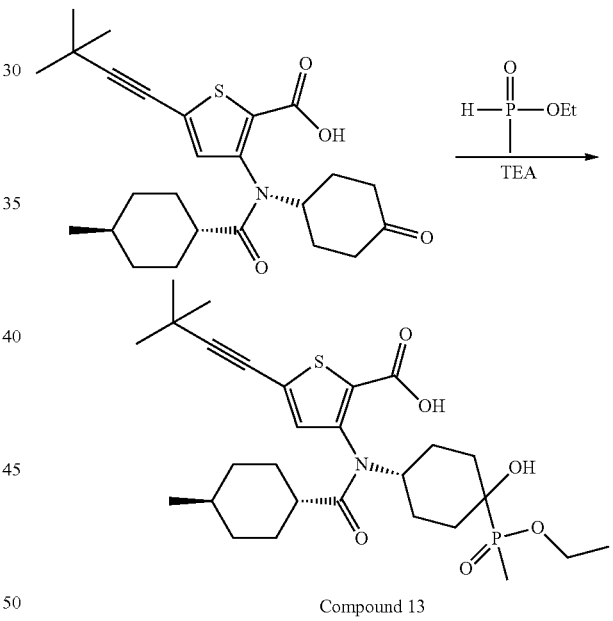

Compound 13

5-(3,3-Dimethyl-but-1-ynyl)-3-[(trans-4-methyl-cyclohexanecarbonyl)-(4-oxo-cyclohexyl)-amino]-thiophene-2-carboxylic acid (100 mg, 0.23 mmol), ethyl methylphosphinate (49 mg, 0.46 mmol) and triethylamine (96 µL, 0.69 mmol) were heated with stirring at 100° C. for 2 hours and then cooled to room temperature. The solvent was removed under vacuum and the residue purified by HPLC (Gemini column; 5% acetonitrile:water, 5 min; 5-100% acetonitrile: water, 18 min; 100% acetonitrile, 6 min; both solvents containing 0.1% trifluoroacetic acid). This resulted in 35 mg of the title compound (as a mixture of cis- and trans-isomers): MS (m/z): 552.2 [M−H]+; HPLC retention time: 4.111 min and 4.211 min (2-98% acetonitrile:water with 0.05% trifluoroacetic acid)

Example 14

Compound 14: 5-(3,3-dimethylbut-1-ynyl)-3-((1r,4r)-N-(4-(ethoxy(methyl)phosphoryl)-4-hydroxycyclohexyl)-(trans-4-methylcyclohexanecarboxamido)thiophene-2-carboxylic acid

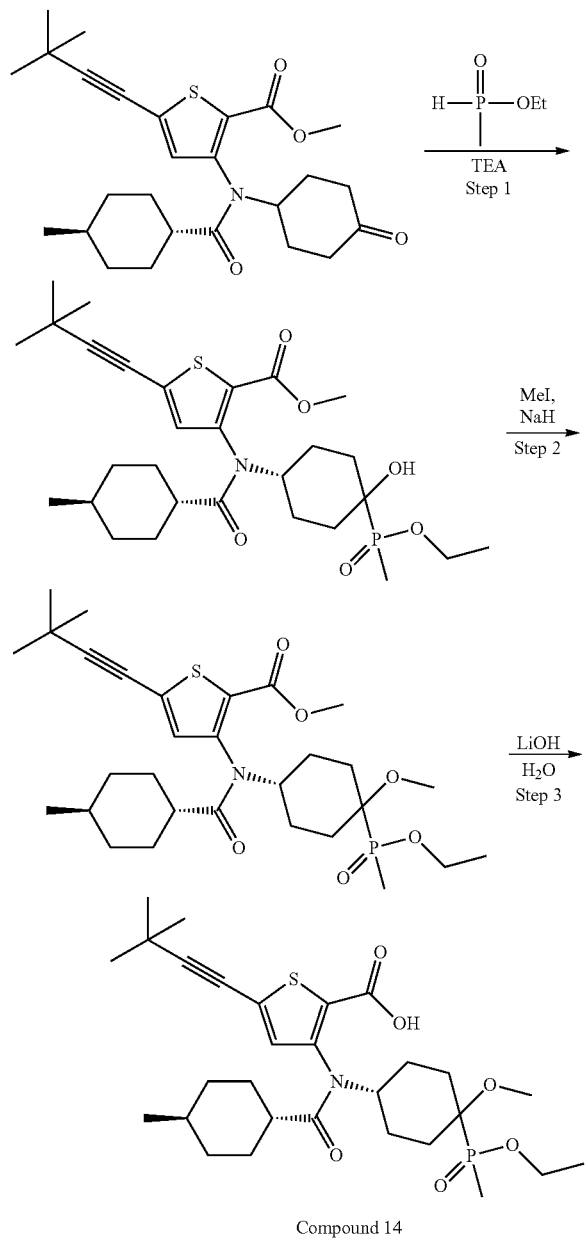

Compound 14

Step 1: Synthesis of methyl 5-(3,3-dimethylbut-1-ynyl)-3-(N-(4-(ethoxy(methyl)phosphoryl)-4-hydroxycyclohexyl)-(trans-4-methylcyclohexanecarboxamido)thiophene-2-carboxylate 5-(3,3-Dimethyl-but-1-ynyl)-3-[(trans-4-methyl-cyclohexanecarbonyl)-(4-oxo-cyclohexyl)-amino]-thiophene-2-carboxylic acid methyl ester (500 mg, 1.1 mmol), ethyl methylphosphinate (238 mg, 2.2 mmol) and triethylamine (306 μL, 2.2 mmol) were heated at 100° C. for 2 hours with stirring and then cooled down to room temperature. Further portions of ethyl methylphosphinate (119 mg, 1.1 mmol) and triethylamine (153 μL, 1.1 mmol) were added and heating at 100° C. was continued for 5 hours. The reaction mixture was cooled to room temperature and the solvent was removed under vacuum. The residue was purified by HPLC (Gemini column; 5% acetonitrile:water, 5 min; 5-100% acetonitrile:water, 18 min; 100% acetonitrile, 6 min; both solvents containing 0.1% trifluoroacetic acid). This resulted in 380 mg of the title compound (mixture of cis- and trans-isomers): MS (m/z): 566.2 [M+H]$^+$; HPLC retention time: 4.860 min and 4.955 min (2-98% acetonitrile:water with 0.05% trifluoroacetic acid).

Step 2: Synthesis of methyl 5-(3,3-dimethylbut-1-ynyl)-3-(N-(4-(ethoxy(methyl)phosphoryl)-4-methoxycyclohexyl)-(trans-4-methylcyclohexanecarboxamido)thiophene-2-carboxylate Methyl 5-(3,3-dimethylbut-1-ynyl)-3-(N-(4-(ethoxy(methyl)phosphoryl)-4-hydroxycyclohexyl)-(trans-4-methylcyclohexanecarboxamido)thiophene-2-carboxylate (85 mg, 0.15 mmol, mixture of cis- and trans-isomers) and iodomethane (47 μL, 0.75 mmol) were dissolved in 0.5 mL of DMF and cooled to 0° C. A suspension of NaH (12 mg, 0.30 mmol, 60% dispersion in mineral oil) in 0.5 mL of DMF was added slowly and then the reaction mixture was allowed to stir at room temperature for 20 min. The reaction was neutralized at 0° C. by the addition of saturated aqueous NH$_4$Cl and then partitioned between water and ethyl acetate. The aqueous phase was extracted with ethyl acetate. The combined organic layers were washed with 5% LiCl and brine, dried over magnesium sulfate, filtered and concentrated. The residue was purified by HPLC (Gemini column; 5% acetonitrile:water, 5 min; 5-100% acetonitrile:water, 18 min; 100% acetonitrile, 6 min; both solvents containing 0.1% trifluoroacetic acid). This resulted in 60 mg of the title compound. MS (m/z): 580.3 [M+H]$^+$; HPLC retention time: 5.434 min and 5.700 min (2-98% acetonitrile:water with 0.05% trifluoroacetic acid).

Step 3: Synthesis of 5-(3,3-dimethylbut-1-ynyl)-3-(N-(4-(ethoxy(methyl)phosphoryl)-4-methoxycyclohexyl)-(trans-4-methylcyclohexanecarboxamido)thiophene-2-carboxylic acid Methyl 5-(3,3-dimethylbut-1-ynyl)-3-(N-(4-(ethoxy(methyl)phosphoryl)-4-methoxycyclohexyl)-(trans-4-methylcyclohexanecarboxamido)thiophene-2-carboxylate (60 mg, 0.1 mmol) was dissolved in 0.5 mL of methanol and 0.5 mL of THF, and to the solution was added 0.3 mL of 1N LiOH. The reaction mixture was allowed to stir at room temperature for 3 hours, cooled to 0° C. and neutralized with 0.5 N HCl. The solvent was removed under vacuum. The residue was purified by HPLC (Gemini column; 5% acetonitrile:water, 5 min; 5-100% acetonitrile:water, 18 min; 100% acetonitrile, 6 min; both solvents containing 0.1% trifluoroacetic acid). This resulted in 9 mg of one isomer of the title compound (MS (m/z): 566.3 [M+H]$^+$; HPLC retention time: 4.544 min (2-98% acetonitrile:water with 0.05% trifluoroacetic acid)) and 9 mg of the other isomer (MS (m/z): 566.3 [M+H]$^+$; HPLC retention time: 4.751 min (2-98% acetonitrile:water with 0.05% trifluoroacetic acid)).

Example 15

Compound 15: 5-(3,3-Dimethyl-but-1-ynyl)-3-[[2-(dimethyl-phosphinoyloxy)-ethyl]-(trans-4-methyl-cyclohexanecarbonyl)-amino]-thiophene-2-carboxylic acid

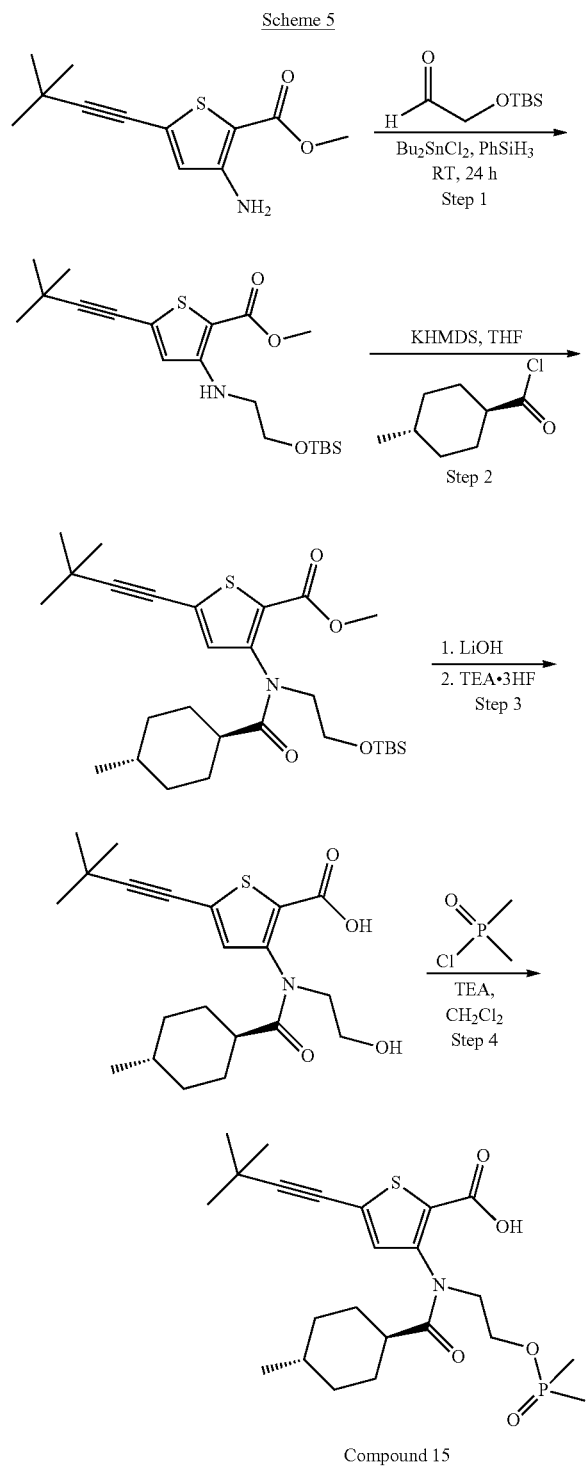

Scheme 5

Compound 15

Step 1: Synthesis of 3-[2-(tert-Butyl-dimethyl-silanyloxy)-ethylamino]-5-(3,3-dimethyl-but-1-ynyl)-thiophene-2-carboxylic acid methyl ester The title compound was synthesized in a manner analogous to Example 11 step 1, using (tent-Butyl-dimethyl-silanyloxy)-acetaldehyde in place of 1-Methoxy-1-oxo-1λ⁵phosphinan-4-one; reaction time was 24 hours.

Step 2: Synthesis of 3-[[2-(tert-Butyl-dimethyl-silanyloxy)-ethyl]-(trans-4-methyl-cyclohexanecarbonyl)-amino]-5-(3,3-dimethyl-but-1-ynyl)-thiophene-2-carboxylic acid methyl ester The title compound was synthesized in a manner analogous to Example 11 step 2, using 3-[2-(tert-Butyl-dimethyl-silanyloxy)-ethylamino]-5-(3,3-dimethyl-but-1-ynyl)-thiophene-2-carboxylic acid methyl ester in place of methyl 5-(3,3-Dimethyl-but-1-ynyl)-3-(1-methoxy-1-oxo-1λ⁵phosphinan-4-ylamino)-thiophene-2-carboxylate: MS (m/z): 520.3 [M+H].

Step 3: Synthesis of 5-(3,3-Dimethyl-but-1-ynyl)-3-[(2-hydroxy-ethyl)-(trans-4-methyl-cyclohexanecarbonyl)-amino]-thiophene-2-carboxylic acid 3-[[2-(tert-Butyl-dimethyl-silanyloxy)-ethyl]-(trans-4-methyl-cyclohexanecarbonyl)-amino]-5-(3,3-dimethyl-but-1-ynyl)-thiophene-2-carboxylic acid methyl ester (450 mg, 0.86 mmol) in a 1:1:1 mixture of THF:MeOH:0.5N lithium hydroxide (18 mL) was stirred at room temperature for 24 hours. The reaction mixture was acidified with 10% HCl$_{(aq)}$ then partitioned between ethyl acetate and water. The organic phase was dried over sodium sulfate then concentrated to dryness. The residue was purified by silica gel chromatography (10-50% ethyl acetate:hexanes), resulting in 273 mg of 3-[[2-(tert-Butyl-dimethyl-silanyloxy)-ethyl]-(trans-4-methyl-cyclohexanecarbonyl)-amino]-5-(3,3-dimethyl-but-1-ynyl)-thiophene-2-carboxylic acid.

3-[[2-(tert-Butyl-dimethyl-silanyloxy)-ethyl]-(trans-4-methyl-cyclohexanecarbonyl)-amino]-5-(3,3-dimethyl-but-1-ynyl)-thiophene-2-carboxylic acid (273 mg) in THF (4 mL) was treated with triethylaminetrihydrofluoride (0.5 mL). After 1 hour, volatiles were removed under vacuum and the residue was purified by silica gel chromatography (0-10% Methanol:DCM) to provide 83 mg of 5-(3,3-Dimethyl-but-1-ynyl)-3-[(2-hydroxy-ethyl)-(trans-4-methyl-cyclohexanecarbonyl)-amino]-thiophene-2-carboxylic acid.

Step 4: Synthesis of 3-[[2-(Dimethyl-phosphinoyloxy)-ethyl]-(trans-4-methyl-cyclohexanecarbonyl)-amino]-5-(3,3-dimethyl-but-1-ynyl)-thiophene-2-carboxylic acid The title compound was synthesized in a manner analogous to Example 1, using 5-(3,3-Dimethyl-but-1-ynyl)-3-[(2-hydroxy-ethyl)-(trans-4-methyl-cyclohexanecarbonyl)-amino]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid: MS (m/z): 468.2 [M+H]⁻; HPLC retention time: 4.144 min (2-98% acetonitrile:water with 0.05% trifluoroacetic acid).

Example 16

Compound 16: 3-[[2-(Diethyl-phosphinoyloxy)-ethyl]-(trans-4-methyl-cyclohexariecarbonyl)-amino]-5-(3,3-dimethyl-but-1-ynyl)-thiophene-2-carboxylic acid Compound 16

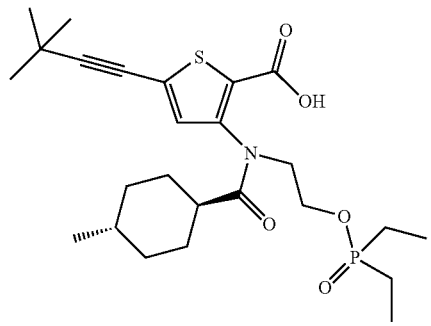

The title compound was synthesized in a manner analogous to Example 15, using diethylphosphinic chloride in place of dimethylphosphinic chloride: MS (m/z): 496.2 [M+]$^-$; HPLC retention time: 2.70 min (2-98% acetonitrile: water with 0.05% trifluoroacetic acid).

Example 17

Compound 17: 5-(3,3-Dimethyl-but-1-ynyl)-3-[[trans-4-(dimethyl-phosphinoyloxy)-cyclobutyl]-(cis-4-methyl-cyclohexanecarbonyl)-amino]-thiophene-2-carboxylic acid Scheme 6

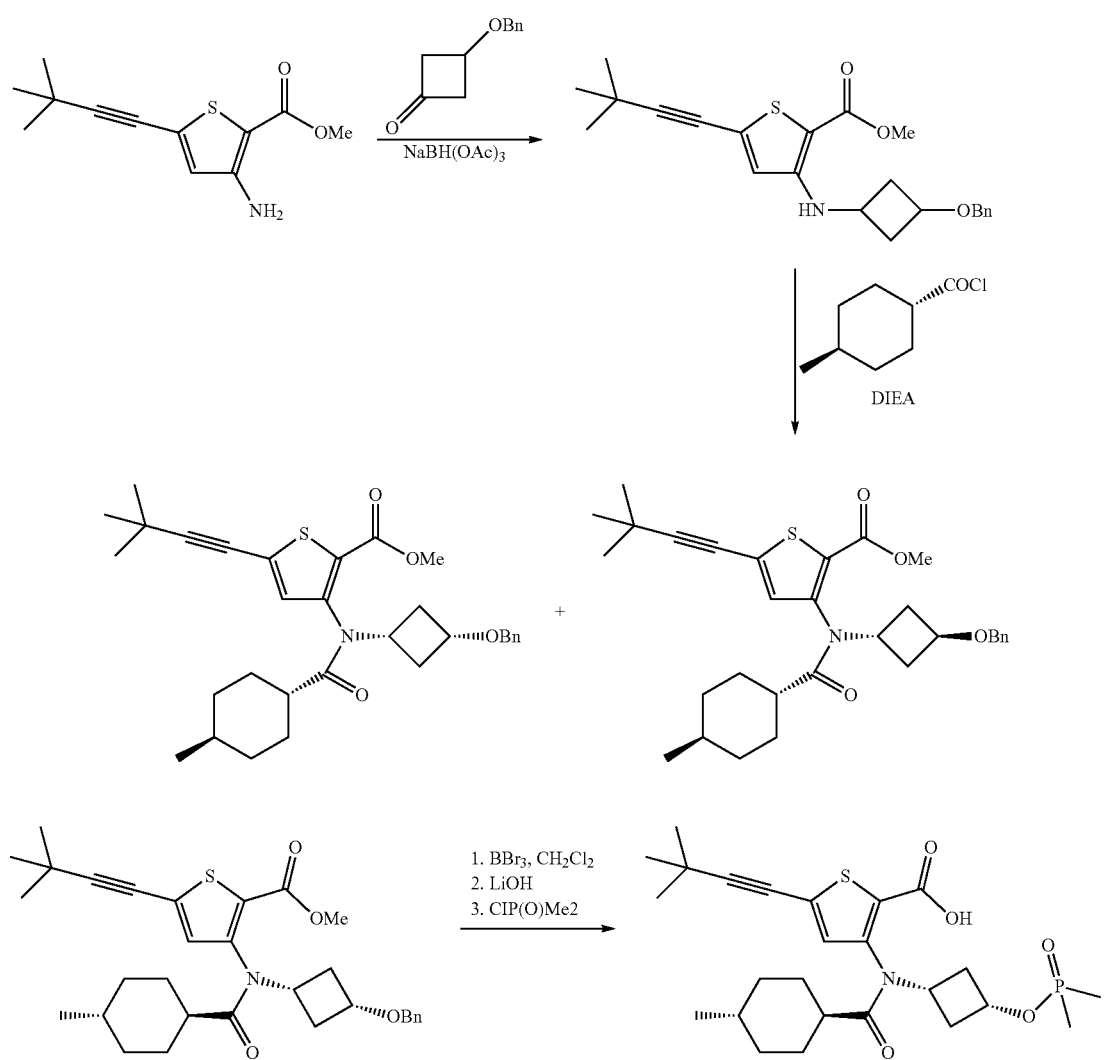

Compound 17

A mixture of 3-amino-5-(3,3-dimethyl-but-1-ynyl)-thiophene-2-carboxylic acid methyl ester, hydrochloride salt (750 mg, 2.74 mmol) and 3-benzyloxy-cyclobutanone (2.5 g, 14.3 mmol) in DCM (40 mL) was treated with sodium triacetoxyborohydride (3.34 g, 15.8 mmol) portionwise. The mixture was stirred at room temperature for 3 hours. The solution was diluted with ethyl acetate, washed sequentially with saturated aqueous sodium bicarbonate, water, and brine. The organic phase was dried over magnesium sulfate, filtered and concentrated. The residue was purified by silica gel chromatography (0-10% ethyl acetate:hexanes). This resulted in 1.26 g (quant. yield) of 3-(3-benzyloxy-cyclobutylamino)-5-(3,3-dimethyl-but-1-ynyl)-thiophene-2-carboxylic acid methyl ester as a mixture of cis- and trans-isomers.

A mixture of 3-(3-Benzyloxy-cyclobutylamino)-5-(3,3-dimethyl-but-1-ynyl)-thiophene-2-carboxylic acid methyl ester (1.26 g, 3.17 mmol) and N,N-diisopropylethylamine (2.4 mL, 13.8 mmol) in DCE (8 mL) was treated with trans-4-methyl-cyclohexanecarbonyl chloride and heated to 100° C. for 5 hours. The reaction mixture was cooled to room temperature, adsorbed onto silica, and purified by silica gel chromatography (0-30% ethyl acetate:hexanes). This resulted in 590 mg (36% yield) of cis-cyclobutyl isomer (cis-3-[(3-benzyloxy-cyclobutyl)-(4-methyl-cyclohexanecarbonyl)-amino]-5-(3,3-dimethyl-but-1-ynyl)-thiophene-2-carboxylic acid methyl ester) and 230 mg (14% yield) of the trans-cyclobutyl isomer (trans-3-[(3-benzyloxy-cyclobutyl)-(4-methyl-cyclohexanecarbonyl)-amino]-5-(3,3-dimethyl-but-1-ynyl)-thiophene-2-carboxylic acid methyl ester).

3-[(cis-3-benzyloxy-cyclobutyl)-(trans-4-methyl-cyclohexanecarbonyl)-amino]-5-(3,3-dimethyl-but-1-ynyl)-thiophene-2-carboxylic acid methyl ester (290 mg, 0.55 mmol) in DCM (2 mL) at 0° C. was treated with boron tribromide (0.85 mL, 1.0 M solution in DCM). The mixture was stirred at 0° C. for 15 minutes and quenched with the addition of silica gel. Volatiles were evaporated under reduced pressure and the reaction mixture was purified by silica gel chromatography (0-100% ethyl acetate:hexanes). This resulted in 210 mg (88% yield) of 5-(3,3-Dimethyl-but-1-ynyl)-3-[(cis-3-hydroxy-cyclobutyl)-(trans-4-methyl-cyclohexanecarbonyl)-amino]-thiophene-2-carboxylic acid methyl ester.

5-(3,3-Dimethyl-but-1-ynyl)-3-[(cis-3-hydroxy-cyclobutyl)-(trans-4-methyl-cyclohexancarbonyl)-amino]-thiophene-2-carboxylic acid methyl ester (400 mg, 0.93 mmol) in a 3:2:1 mixture of THF:MeOH:water (20 mL) was treated with lithium hydroxide (4.5 mL, 1.0 M aqueous solution) and heated to 60° C. for 2 hours. The organic volatiles were evaporated under reduced pressure and remaining solution was acidified with 10% HCl$_{(aq)}$. A white precipitate was collected by vacuum filtration, washed with water, and dried to afford 290 mg (74% yield) of 5-(3,3-Dimethyl-but-1-ynyl)-3-[(cis-3-hydroxy-cyclobutyl)-(4-methyl-cyclohexanecarbonyl)-amino]-thiophene-2-carboxylic acid as a white powder. MS (m/z): 415.8 [M−H]$^−$; HPLC retention time: 4.10 min (2-98% acetonitrile:water with 0.05% trifluoroacetic acid).

The title compound was synthesized in a manner analogous to Example 1, using 5-(3,3-dimethyl-but-1-ynyl)-3-[(cis-3-hydroxy-cyclobutyl)-(4-methyl-cyclohexanecarbonyl)-amino]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid. MS (m/z): 495.1 [M−H]$^−$; HPLC retention time: 4.57 min (2-98% acetonitrile:water with 0.05% trifluoroacetic acid).

Example 18

Compound 18: 5-(3,3-Dimethyl-but-1-ynyl)-3-[[2-(methoxy-methyl-phosphinoyl)-ethyl]-(4-methyl-cyclohexanecarbonyl)-amino]-thiophene-2-carboxylic acid

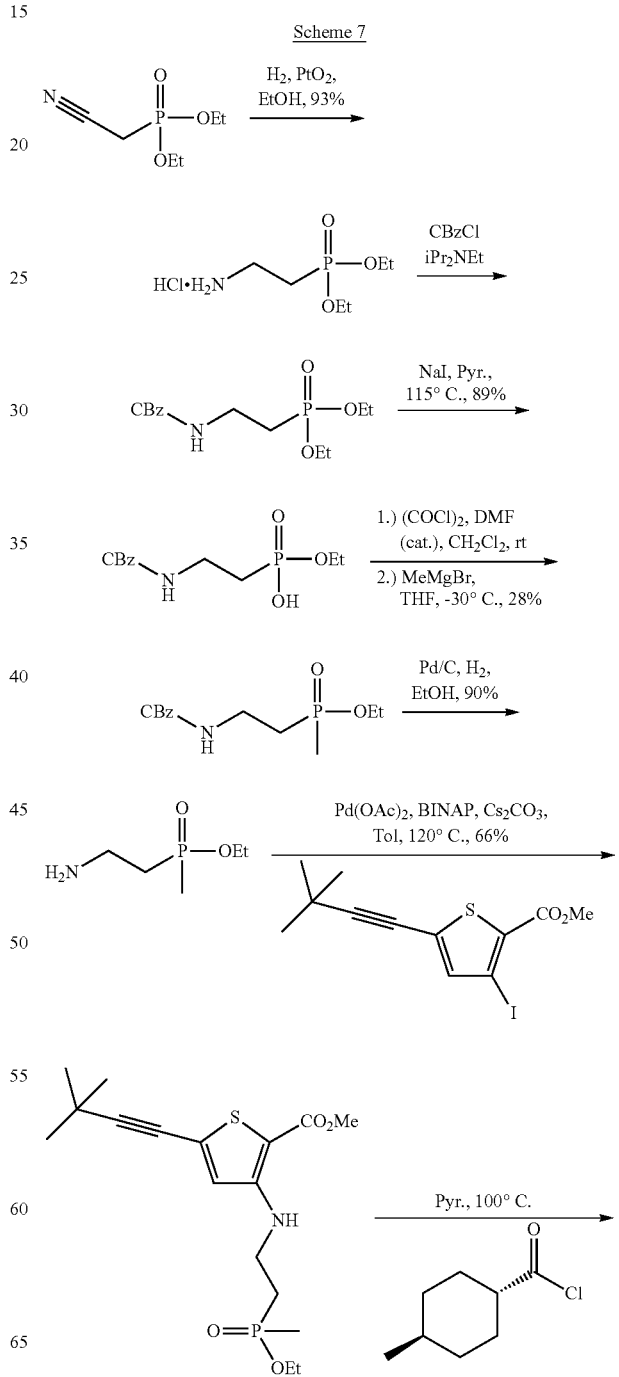

Scheme 7

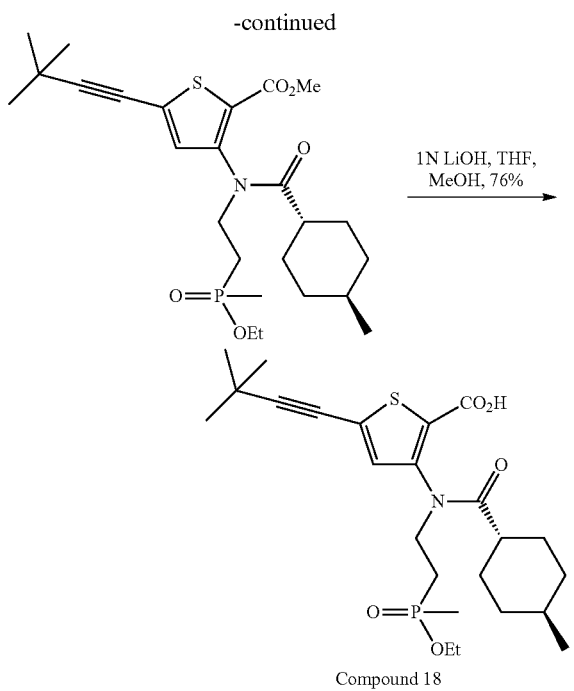

Compound 18

PtO$_2$ (400 mg) was slurried with EtOH (20 mL). To the slurry was added a solution of cyanomethyl-phosphoric acid diethyl ester (4 g, 22.58 mmol) in EtOH (40 mL), followed by 12N HCl (2 mL). The reaction vessel's atmosphere was exchanged with H$_2$ and the reaction was stirred at room temperature until complete, as determined by TLC (eluent: 100% EtOAc). The reaction was then filtered through Supercell NF. The filtrate was concentrated to yield the HCl salt of (2-amino-ethyl)-phosphoric acid diethyl ester as a white solid (4.55, 93%).

The HCl salt of (2-amino-ethyl)-phosphonic acid diethyl ester (4.5 g, 20.7 mmol) was dissolved in CH$_2$Cl$_2$ (100 mL). To this solution was added CBzCl (3.2 mL, 22.7 mmol), followed by iPr$_2$NEt (14.4 mL, 82.8 mmol). The reaction was stirred at room temperature until complete, as determined by TLC (eluent: 100% EtOAc). The reaction was quenched by the addition of saturated NaHCO$_3$. The mixture was then partitioned between CH$_2$Cl$_2$ and H$_2$O. The layers were separated and the organic layer was washed with brine and then dried over Na$_2$SO$_4$. The drying agent was removed by vacuum filtration and (2-benzyloxycarbonylamino-ethyl)-phosphoric acid diethyl ester was isolated from the concentrated filtrate by silica gel column chromatography (EtOAc/hexanes) (5.98 g, 92%).

(2-Benzyloxycarbonylamino-ethyl)-phosphonic acid diethyl ester (5.77 g, 18.3 mmol) was dissolved in pyridine (61 mL). To this solution was added NaI (13.7 g, 92 mmol). The mixture was heated at 115° C. overnight. The next day the reaction was determined, by LC/MS, to be largely complete. The reaction was cooled to room temperature and concentrated in vacuo. The residue was dissolved in H$_2$O and extracted with Et$_2$O. The water was then cooled in an ice bath and the adjusted to pH 2 with 2N HCl. The water was then extracted with CH$_2$Cl$_2$ and the combined organic layers were washed with brine and dried over Na$_2$SO4. The drying agent was removed by vacuum filtration and the filtrate was concentrated to yield (2-benzyloxycarbonylamino-ethyl)-phosphonic acid monoethyl ester (4.68 g, 89%) as an oil that turned to a waxy solid under high vacuum.

Oxaloyl chloride (2.88 mL, 33 mmol) was dissolved in CH$_2$Cl$_2$ (42 mL). DMF (284 □L) was added to this solution in a drop-wise manner. After 15 minutes a solution of (2-benzyloxycarbonylamino-ethyl)-phosphoric acid monoethyl ester (4.75 g, 16.5 mmol) in solution with CH$_2$Cl$_2$ (42 mL) was added drop-wise over 20 minutes at room temperature. The reaction was stirred at room temperature for 40 minutes. The reaction was determined to be complete by the absence of starting material in a $^{31}$P NMR spectrum of the crude reaction mixture. The reaction was concentrated in vacuo to yield an orange-brown oil that was placed under high vacuum overnight. The oil was then dissolved in THF (80 mL) and cooled to −30° C., as determined by an internal thermometer. A 1M solution of MeMgBr in a mixture of toluene and THF was then slowly added to the reaction while keeping the internal temperature at about −30° C. The mixture was stirred at −30° C. for 45 minutes and then another 1 equivalent of MeMgBr was added. After stirring at −30° C. for another 45 minutes the reaction was quenched by the addition of saturated NH$_4$Cl. The reaction was warmed to room temperature and then partitioned between EtOAc and H$_2$O. The layers were separated and the organic layer was washed with brine and dried over Na$_2$SO$_4$. (2-Benzyloxycarbonylamino-ethyl)-methyl-phosphinic acid ethyl ester was isolated from the concentrated filtrate (1.33 g, 28%) by silica gel column chromatography (EtOAc/hexanes then MeOH/CH$_2$Cl$_2$) as a yellow crystalline solid.

(2-Benzyloxycarbonylamino-ethyl)-methyl-phosphinic acid ethyl ester (1.3 g, 4.56 mmol) and 10% Pd/C (485 mg) were combined in a flask and EtOH (46 mL) was added. The reaction flask atmosphere was exchanged for H$_2$ and the reaction was run at room temperature until complete, as determined by TLC (eluent: 100% EtOAc). The reaction was then filtered through Supercell NF and the filtrate was concentrated to yield (2-amino-ethyl)-methyl-phosphinic acid ethyl ester (615 mg, 90%) as a yellow oil in which white crystals began to form under high vacuum.

5-(3,3-Dimethyl-but-1-ynyl)-3-iodo-thiophene-2-carboxylic acid methyl ester (669 mg, 1.92 mmol), Pd(OAc)$_2$ (64 mg, 0.288 mmol), BINAP (179 mg, 0.288 mmol), and Cs$_2$CO$_3$ (1.56 g, 4.8 mmol) were combined in a sealed tube. A solution of (2-amino-ethyl)-methyl-phosphinic acid ethyl ester (578 mg, 3.85 mmol) in toluene (14 mL), which had been degassed by bubbling argon through it for 30 minutes, was added. The sealed tube was purged with argon and then sealed. The tube was placed in a 120° C. oil bath. The reaction was stirred overnight, then cooled to room temperature and filtered through filter paper. The residue was stirred vigorously with EtOAc and then the EtOAc was passed through filter paper. The combined filtrates were concentrated and 5-(3,3-Dimethyl-but-1-ynyl)-3-[2-(ethoxy-methyl-phosphinoyl)-ethylamino]-thiophene-2-carboxylic acid methyl ester (466 mg, 66%) was isolated by silica gel column chromatography (MeOH/EtOAc) as a green crystalline solid.

5-(3,3-Dimethyl-but-1-ynyl)-3-[2-(ethoxy-methyl-phosphinoyl)-ethylamino]-thiophene-2-carboxylic acid methyl ester (233 mg, 0.629 mmol) was dissolved in pyridine (4 mL) and then 4-methyl-cyclohexanecarbonyl chloride (506 mg, 3.15 mmol) was added. The reaction was stirred for 7 hours at 100° C., the heat to the oil bath was shut off and the reaction was allowed to stir for a further 9 hours. The reaction was diluted with EtOAc and extracted with H$_2$O. The organic phase was then extracted with brine and dried over Na$_2$SO$_4$. The drying agent was removed by vacuum filtration and the filtrate was concentrated. 5-(3,3-Dimethyl-but-1-ynyl)-3-[[2-(ethoxy-methyl-phosphinoyl)-ethyl]-(4-methyl-cyclohexanecarbonyl)-amino]-thiophene-2-carboxylic acid methyl ester (251 mg, 78%) was isolated from the residue by silica gel column chromatography.

5-(3,3-Dimethyl-but-1-ynyl)-3-[[2-(ethoxy-methyl-phosphinoyl)-ethyl]-(4-methyl-cyclohexanecarbonyl)-amino]-thiophene-2-carboxylic acid methyl ester (251 mg, 0.51 mmol) was dissolved in THF (7.3 mL) and MeOH (7.3 mL). A 1N solution of LiOH in H$_2$O (1.52 mL, 1.52 mmol) was added to the reaction drop-wise at room temperature. The reaction was run at room temperature until complete, as determined by LC/MS. The reaction was cooled in an ice bath and then acidified to pH 3 with 1N HCl. The entire mixture was then evaporated in vacuo and stored under high vacuum overnight. 5-(3,3-Dimethyl-but-1-ynyl)-3-[[2-(ethoxy-methyl-phosphinoyl)-ethyl]-(4-methyl-cyclohexanecarbonyl)-amino]-thiophene-2-carboxylic acid (168 mg, 69%) was isolated from the residue by reverse phase HPLC. MS (m/z): 481.93 [M+H]+; $^{31}$P NMR (161.9 MHz, CDCl$_3$): d 56.771, 55.816.

The synthesis of 5-(3,3-Dimethyl-but-1-ynyl)-3-iodo-thiophene-2-carboxylic acid methyl ester, required in the above route, is illustrated below:

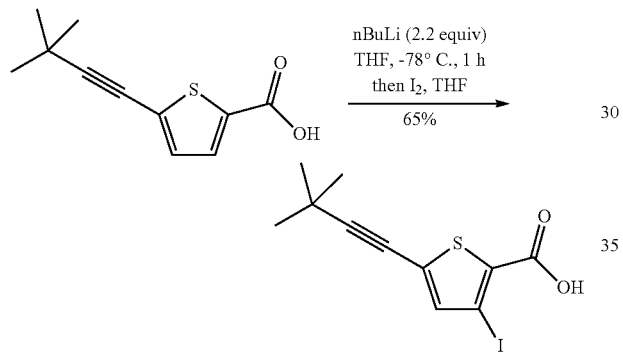

To a solution of 5-(3,3-Dimethyl-but-1-ynyl)-thiophene-2-carboxylic acid (6.2 g, 30 mmol; see patent application U.S. Pat. No. 5,861,421) in THF (100 mL) was added a solution of nBuLi (2.0 M in pentane, 33 mL, 66 mmol) via an addition funnel at −78° C. After addition, the reaction was stirred at −78° C. for 1 h. A solution of I$_2$ (7.7 g, 30 mmol) in THF (100 mL) was added slowly (ca. 15 min) to the flask. After a further 10 mins, the reaction was quenched with 1 N HCl (50 mL) and warmed to room temperature. The volatiles were removed in vacuo and the residue was dissolved in ether (500 mL). The organic solution was washed with 1 M Na$_2$S$_2$O$_3$ (100 mL×2), brine (100 mL) and dried over Na$_2$SO$_4$. After concentrated in vacuo, the residue was purified by silica gel chromatography (EtOAc/hexanes) to give 5-(3,3-Dimethyl-but-1-ynyl)-3-iodo-thiophene-2-carboxylic acid (5.9 g, 65%) as a white solid.

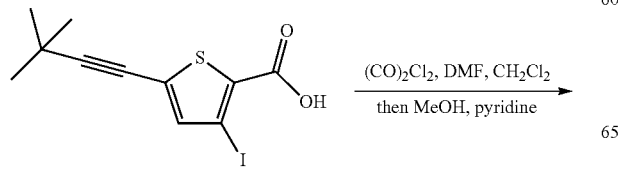

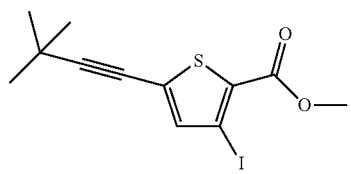

To a solution of 5-(3,3-Dimethyl-but-1-ynyl)-3-iodo-thiophene-2-carboxylic acid (1.0 g, 3.0 mmol) and DMF (20 µL) in dry dichloromethane (10 mL) was added oxalyl chloride (508 µL, 6.0 mmol) at room temperature. After stirring at room temperature for 90 min, the reaction was concentrated in vacuo to remove volatiles. The residue was dissolved in pyridine (5 mL) and methanol (5 mL) and stirred for 2 h. The volatiles were removed in vacuo and the residue was participated between ether (150 mL) and saturated NH$_4$Cl solution (50 mL). The organic layer was washed with saturated NH$_4$Cl solution (50 mL) and dried over Na$_2$SO$_4$. After concentration in vacuo, the residue was purified by silica gel chromatography (EtOAc/hexanes) to give the desired product (835 mg, 80%).

Example 19

Compound 19: 5-(3,3-dimethyl-but-1-ynyl)-3-[[2-(hydroxy-methyl-phosphinoyl)-ethyl]-(4-methyl-cyclohexanecarbonyl)-amino]-thiophene-2-carboxylic acid

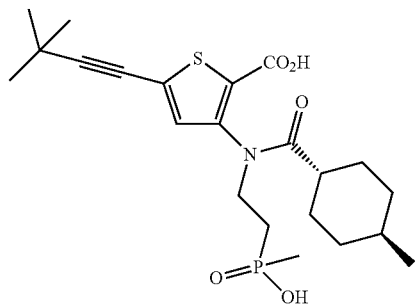

Compound 19

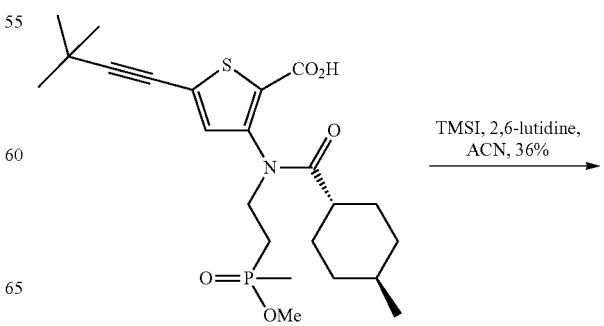

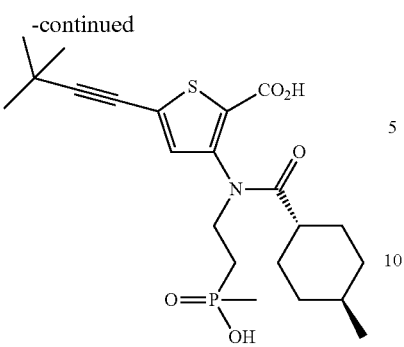

5-(3,3-Dimethyl-but-1-ynyl)-3-[[2-(ethoxy-methyl-phosohinoyl)-ethyl]-(4-methyl-cyclohexanecarbonyl)-amino]-thiophene-2-carboxylic acid (108 mg, 0.225 mmol) was dissolved in acetonitrile (3 mL). This solution was cooled in an ice bath and TMSI (160 µL, 1.12 mmol) was added dropwise. The reaction turned yellow and some precipitate was formed. After approximately 1 minute 2,6-lutidine (156 µL, 1.35 mmol) was added, resulting in a clear solution. The ice bath was removed and the reaction was stirred at room temperature for 2 hours. Additional TMSI (50 µL) and 2,6-lutidine (50 µL) were added. After 45 minutes the reaction was determined by LC/MS to be complete. The reaction was cooled in an ice bath and additional 2,6-lutidine (100 µL) was added, followed by MeOH (2 mL). The reaction was warmed to room temperature and concentrated under vacuum. 5-(3,3-Dimethyl-but-1-ynyl)-3-[[2-(hydroxy-methyl-phosphinoyl)-ethyl]-(4-methyl-cyclohexanecarbonyl)-amino]-thiophene-2-carboxylic acid (37 mg, 36%) was isolated from the residue by reverse phase HPLC. MS (m/z): 453.93 [M+H]+; $^{31}$P NMR (161.9 MHz, CD$_3$OD): δ 49.909.

Example 24

Compound 24: 3-(1,4-N-(4-(2-(diethoxyphosphoryl)ethylamino)cyclohexyl)-4-methylcyclohexanecarboxamido)-5-(3,3-dimethylbut-1-ynyl)thiophene-2-carboxylic acid

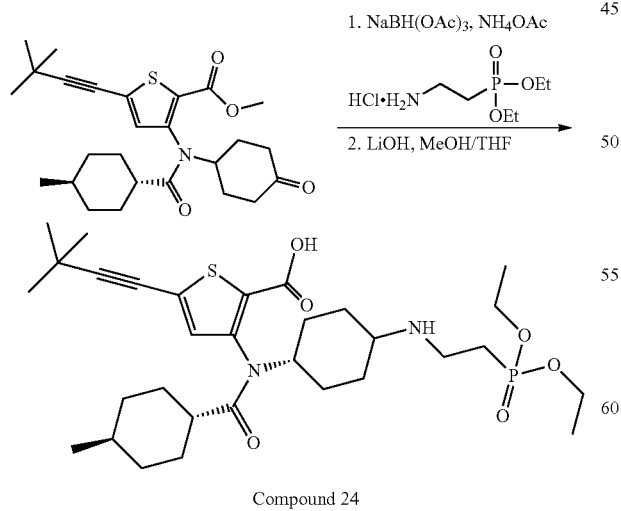

Compound 24

Compound 24 was prepared by reductive amination using the same method as described for Example 9, Step 1.

MS=609.24
Retention time: 2.18 min
LC: Thermo Finnigan PDA Detector
MS: Thermo Scientific LCQ Fleet
Column: Phenomenex Gemini-nx 3u C18 110A 30×3 mm
Solvents: Acetonitrile with 0.1% trifluoroacetic acid, Water with 0.1% trifluoroacetic acid
Gradient: 0 min-3.1 min 2%-100% ACN, 3.1 min-3.75 min 100% ACN Synthesis of
(1S,6S)-4,6-dimethyl-cyclohex-3-enecarboxylic acid Scheme 2

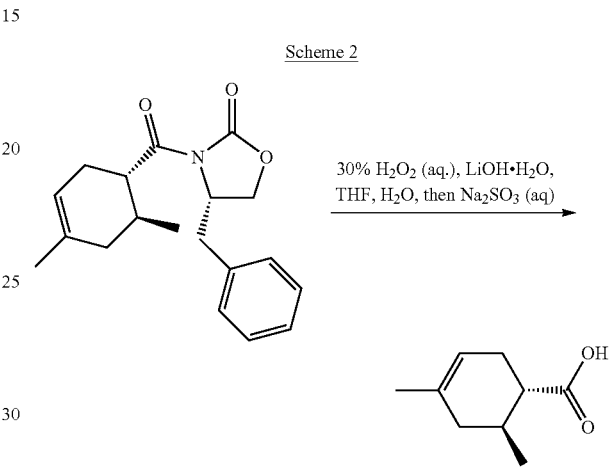

4S-benzyl-3-(4,6S-dimethyl-cyclohex-3-ene-1S-carbonyl)-oxazolidin-2-one, prepared in a method similar to that described in *J. Am. Chem. Soc.* 110(4), 1988, 1238-1256, was dissolved in THF (1000 mL) and H$_2$O (350 mL). The solution was cooled in an ice bath and 30% H$_2$O$_2$ (36 mL, 354 mmol) was slowly added followed by LiOH*H$_2$O (9.90 g, 263 mmol) in one portion. The reaction was allowed to slowly warm to rt and was stirred for 16 h. The reaction was then cooled in an ice bath. Na$_2$SO$_3$ (60 g, 472 mmol) was dissolved H$_2$O (400 mL) and very slowly added to the cooled reaction mixture. The solution was stirred for 1 h, and the layers were separated. The organic layer was concentrated under reduced pressure. The aqueous layer was added back to the organic concentrate and was washed with CH$_2$Cl$_2$ (2×500 mL). The pH of the aqueous layer was adjusted to 2 through a slow addition of conc. HCl. The aqueous layer was extracted with EtOAc (4×300 mL) and dried over Na$_2$SO$_4$. The ethyl acetate extracts were combined and concentrated under reduced pressure co-evaporating with hexanes to afford (1S,6S)-4,6-dimethyl-cyclohex-3-enecarboxylic acid (14.14 g, 78%) as a white solid.

Synthesis of
(1R,6R)-4,6-dimethyl-cyclohex-3-enecarboxylic acid

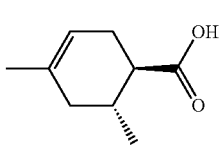

4,6R-Dimethyl-cyclohex-3-ene-1R-carboxylic acid was prepared in a similar manner to 4,6S-dimethyl-cyclohex-3-ene-1S-carboxylic acid, using the chiral auxiliary 4R-benzyl-oxazolidin-2-one.

Synthesis of 5-(3,3-Dimethyl-but-1-ynyl)-3-[(1S,6S)-(4,6-dimethyl-cyclohex-3-enecarbonyl)-(4-hydroxy-cyclohexyl)-amino]-thiophene-2-carboxylic acid

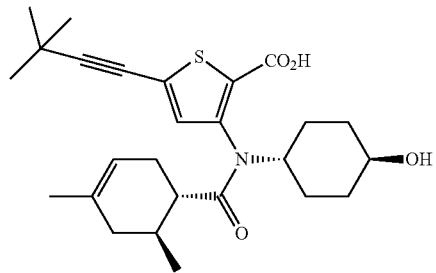 [SMILES: CC1=CC[C@H](C(=O)N(c2cc(C#CC(C)(C)C)sc2C(=O)O)[C@H]2CC[C@H](O)CC2)[C@@H](C)C1]

Scheme 1

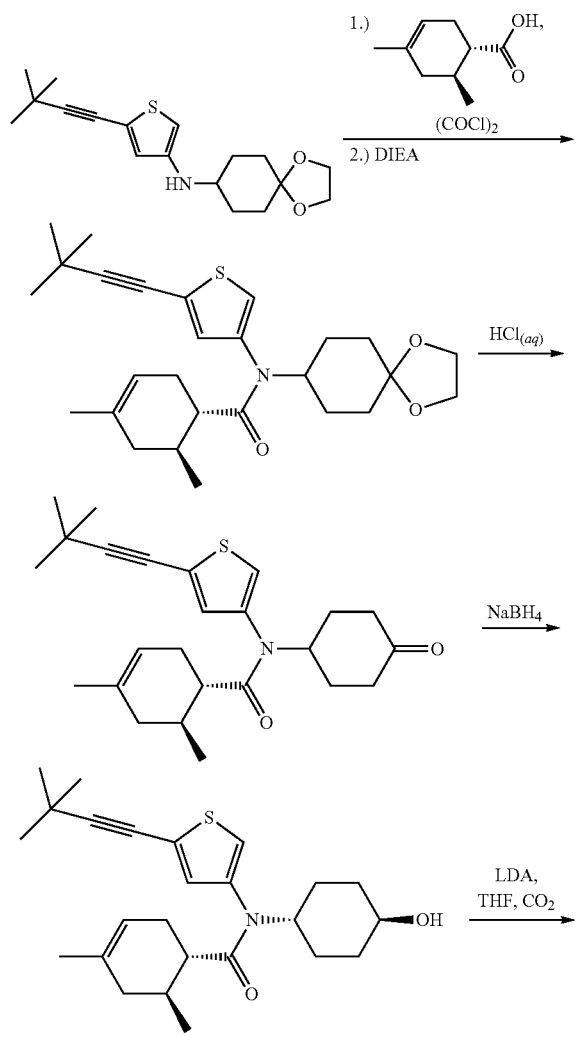

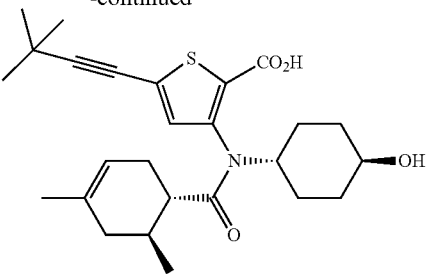

(1S,6S)-4,6-dimethyl-cyclohex-3-ene-carboxylic acid (3.04 g, 19.7 mmol) was dissolved in $CH_2Cl_2$ (30 mL) and DMF (20 μL) was added. The solution was cooled to 0° C. and $(COCl)_2$ (3.7 mL, 39 mmol) was added slowly. The reaction was stirred in an ice bath for 2 hours and then concentrated. The residue was taken up in hexanes and concentrated; this hexanes coevaporation was repeated once more. To the residue was added [5-(3,3-Dimethyl-but-1-ynyl)-thiophen-3-yl]-(1,4-dioxa-spiro[4.5]dec-8-yl)-amine (4.16 g, 13 mmol), diisopropylethylamine (4.5 mL, 26 mmol), and 1,2-dichloroethane (40 mL) at 0° C. The solution was warmed to room temperature and stirred overnight. The reaction was diluted with $CH_2Cl_2$, twice washed with saturated $NH_4Cl_{(aq)}$, dried over $MgSO_4$, filtered, concentrated, and purified by silica gel column chromatography, eluting with a mixture of 0-75% EtOAc/hexanes, to give (1S,6S)-4,6-dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) as a single isomer.

(1S,6S)-4,6-Dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) was dissolved in THF (70 mL) and treated with 4M HCl (35 mL). The reaction mixture was heated to 45° C. and stirred for 2.5 h. THF was removed in vacuo, and the aqueous layer was thrice extracted into ethyl acetate. The combined organic layers were washed with saturated $NaHCO_{3(aq)}$, water, and brine, dried over $MgSO_4$, filtered, and concentrated to give (1S,6S)-4,6-dimethyl-cyclohex-3-ene-carboxylic acid [5-(3,3-dimethyl-but-1-ynyl)-thiophen-3-yl]-(4-oxo-cyclohexyl)-amide (5.05 g, 12 mmol).

(1S,6S)-4,6-Dimethyl-cyclohex-3-ene-carboxylic acid [5-(3,3-dimethyl-but-1-ynyl)-thiophen-3-yl]-(4-oxo-cyclohexyl)-amide (2.0 g, 4.9 mmol) in MeOH (100 mL) was treated with sodium borohydride (230 mg, 6.0 mmol) at 0° C. After stirring for 30 min, 4M HCl (6 mL) was added and the reaction mixture was twice extracted with ethyl acetate. The combined organic layers washed with saturated $NaHCO_{3(aq)}$, brine, dried over $MgSO_4$, filtered, and concentrated. Silica gel chromatography (20-60% ethyl acetate/hexanes) gave the desired (1S,6S)-4,6-dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol).

(1S,6S)-4,6-Dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol) in THF (50 mL) was cooled to −78° C. and treated with lithium diisopropylamine (8.4 mL, 2.0M in heptane/THF/PhEt, 16.8 mmol) and allowed to warm to 0° C. over the course of 2 hours. $CO_2$ was vigorously bubbled through the reaction solution for 10 minutes. The reaction was then quenched with the addition of iPrOH, diluted with ethyl acetate, washed with saturated $NH_4Cl_{(aq)}$, dried over $MgSO_4$, filtered, and concentrated. Silica gel chromatography (0-100% ethyl acetate/dichloromethane) afforded 530 mg (1.2 mmol) of the title compound: MS (m/z): 458.1 [M+H]+; HPLC retention time 4.35 min (2-98% acetonitrile: water with 0.05% trifluoroacetic acid).

Example 25

Compound 25: 5-(3,3-Dimethylbut-1-ynyl)-3-((1S, 6S)-N-((1r,4S)-4-(dimethylphosphoryloxy)cyclohexyl)-4,6-dimethylcyclohex-3-enecarboxamido) thiophene-2-carboxylic acid

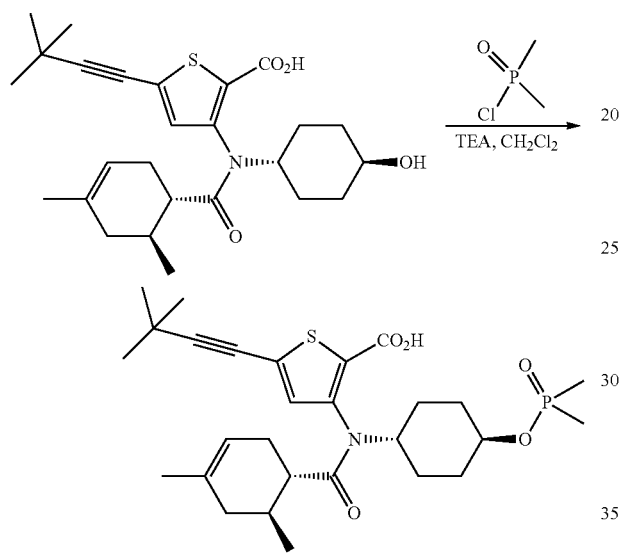

Compound 25 may be prepared in the same manner as Compound 1 by starting with 5-(3,3-dimethyl-but-1-ynyl)-3-[(1S,6S)-(4,6-dimethyl-cyclohex-3-enecarbonyl)-(4-hydroxy-cyclohexyl)-amino]-thiophene-2-carboxylic acid.

Synthesis of 5-(3,3-Dimethyl-but-1-ynyl)-3-[(1R, 6R)-(4,6-dimethyl-cyclohex-3-enecarbonyl)-(4-hydroxy-cyclohexyl)-amino]-thiophene-2-carboxylic acid

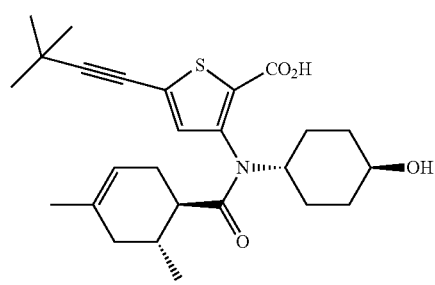 [SMILES: CC1=CC[C@@H](C(=O)N(c2cc(C#CC(C)(C)C)sc2C(=O)O)[C@H]2CC[C@H](O)CC2)[C@H](C)C1]

By substituting (1R,6R)-4,6-dimethyl-cyclohex-3-enecarboxylic acid for (1S,6S)-4,6-dimethyl-cyclohex-3-enecarboxylic acid in Scheme 1, the above titled compound may be prepared.

Example 26

Compound 26: 5(3,3-Dimethylbut-1-ynyl)-3-((1R, 6)-N-((1r,4S)-4-(dimethylphoschoryloxy)cyclohexyl)-4,6-dimethylcyclohex-3-enecarboxamido) thiophene-2-carboxylic acid

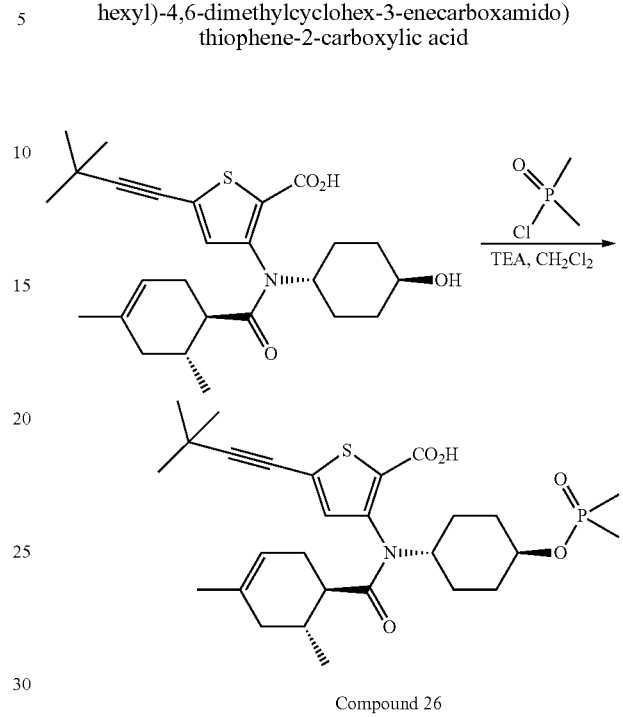

Compound 26

Compound 26 may be prepared in the same manner as Compound 25 starting with 5-(3,3-dimethyl-but-1-ynyl)-3-[(1R,6R)-(4,6-dimethyl-cyclohex-3-enecarbonyl)-(4-hydroxy-cyclohexyl)-amino]-thiophene-2-carboxylic acid rather than 5-(3,3-dimethyl-but-1-ynyl)-3-[(1S,6S)-(4,6-dimethyl-cyclohex-3-enecarbonyl)-(4-hydroxy-cyclohexyl)-amino]-thiophene-2-carboxylic acid.

Synthesis of (1S)-4-methyl-cyclohex-3-enecarboxylic acid

Scheme 15

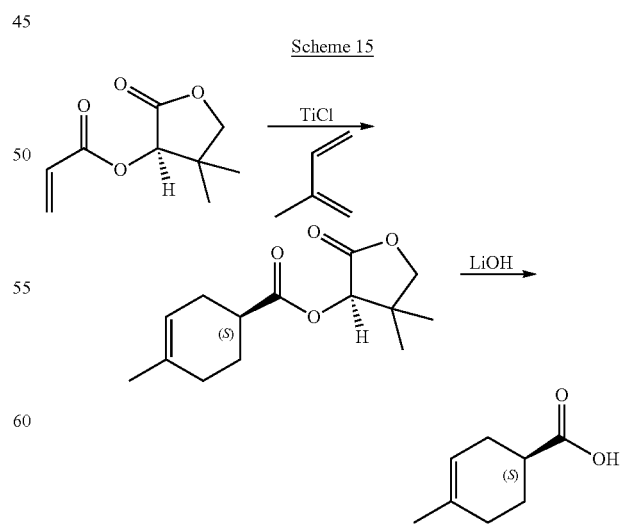

Acrylic acid 4,4-dimethyl-2-oxo-tetrahydro-furan-3-yl ester (R) (2.92 g, 15.9 mmol) in dichloromethane (20 mL) and hexanes (3 mL) was cooled to −10° C. and treated with titanium tetrachloride (2.4 mL, 2.4 M in dichloromethane, 2.4 mmol). The red solution was stirred for 15 min and treated with isoprene (2.4 mL, 23.8 mmol) dropwise over 5 min. After stirring for 1.5 h, an additional portion of isoprene (2.4 mL, 23.8 mmol) was added and the reaction mixture was stirred at −10 to 0° C. for 2.5 h. After cooling to −10° C., the reaction mixture was quenched with ammonium chloride (sat. aq.). Water and ethyl acetate:hexanes (1:1) were added. The organic layer was separated and the aqueous layer was extracted again with ethyl acetate:hexanes (1:1). The combined organic layers were dried over sodium sulfate, filtered and concentrated. The residue was purified by flash chromatography (10-40% EtOAc:Hex, 80 g column) to afford 3.35 g (84% yield) of 4-methyl-cyclohex-3-(S)-enecarboxylic acid 4,4-dimethyl-2-oxo-tetrahydro-furan-3-yl ester as a clear oil.

4-Methyl-cyclohex-3-(S)-enecarboxylic acid 4,4-dimethyl-2-oxo-tetrahydro-furan-3-yl ester (3.34 g, 13.2 mmol) in THF (25 mL), water (2.5 mL) and methanol (2.5 mL) was treated with lithium hydroxide monohydrate (2.8 g, 66.2 mmol) and warmed to 50° C. with stirring. After 1 h, the reaction mixture treated with 1M HCl (about 25 mL). The mixture was extracted with hexanes:ethyl acetate (200 mL: 15 mL), dried over sodium sulfate, filtered and concentrated to 2.4 g of a white semi-solid. The residue was redissolved in hexanes:dichloromethane (100 mL, 95:5), washed with water, dried over sodium sulfate, filtered and concentrated to 1.68 g (91% yield) of (1S)-4-methyl-cyclohex-3-enecarboxylic acid as a white powder.

Synthesis of methyl 5-(3,3-dimethylbut-1-ynyl)-3-((S)—N-((1r,4S)-4-hydroxycyclohexyl)-4-methylcyclohex-3-enecarboxamido)thiophene-2-carboxylate Scheme 19

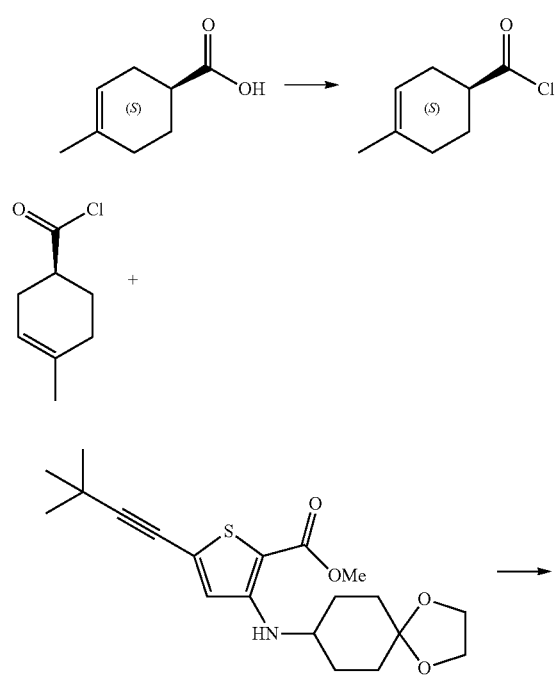

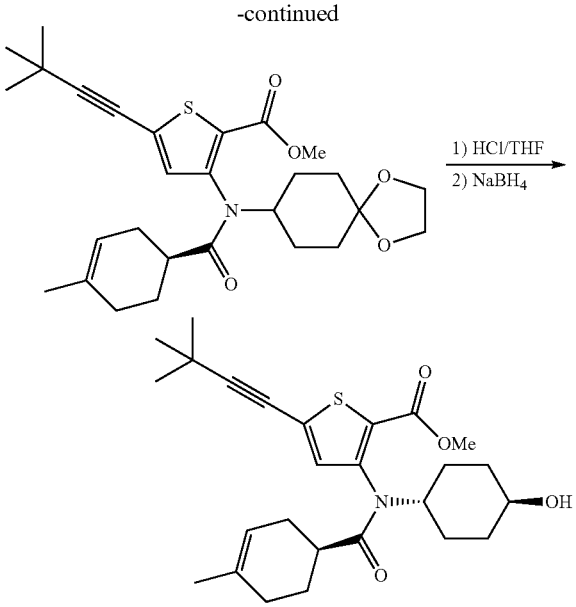

(1S)-4-Methyl-cyclohex-3-ene-1-carboxylic acid (250 mg, 1.78 mmol), azeotropically dried by evaporation from toluene was dissolved in dichloromethane (4 mL) and treated with dimethylformamide (1 drop). The reaction mixture was cooled to 0° C. and treated dropwise with oxalyl chloride (0.42 mL, 4.5 mmol). The reaction mixture was allowed to warm to ambient temperature while stirring for 4 h. The solution was concentrated, treated with hexanes and concentrated again to afford (1S)-4-methyl-cyclohex-3-ene-1-carboxylic acid chloride as a light yellow oil which was used immediately in the next step.

(1S)-4-Methyl-cyclohex-3-ene-1-carboxylic acid chloride (1.8 mmol), dimethyl-but-1-ynyl)-3-(1,4-dioxa-spiro[4.5] dec-8-ylamino)-thiophene-2-carboxylic acid methyl ester (336 mg, 0.89 mmol) and DMAP (217 mg, 1.8 mmol) were dissolved in dichloroethane (2.2 mL), sealed with a cap and heated to 80° C. After 2 h, the temperature was increased to 90° C., and the solution was stirred 16 h. The reaction mixture was further heated to 100° C., stirred 24 h and partitioned between water and ethyl acetate:hexanes (1:1). The layers were separated and the aqueous layer was extracted again with ethyl acetate:hexanes (1:1). The combined organic layers were dried over sodium sulfate, filtered and concentrated. Flash chromatography (5% EtOAc:hexanes 5 min then 5-40% EtOAc:hexanes, 20 min, 24 g column) afforded 250 mg (56% yield of the desired 5-(3,3-dimethyl-but-1-ynyl)-3-[(1,4-dioxa-spiro[4.5]dec-8-yl)-(4-methyl-cyclohex-3-enecarbonyl)-amino]-thiophene-2-carboxylic acid methyl ester as a white foam.

5-(3,3-Dimethyl-but-1-ynyl)-3-[(1,4-dioxa-spiro[4.5]dec-8-yl)-(4-methyl-cyclohex-3-enecarbonyl)-amino]-thiophene-2-carboxylic acid methyl ester (240 mg, 0.48 mmol) was dissolved in THF (3.2 mL) and treated with 4M HCl (1.6 mL, 0.8 mmol). The reaction mixture was heated to 45° C. and stirred at ambient temperature. After 2 h, methanol was added (15-20 drops) and the solution was stirred for 3 h. An additional portion of 4M HCl (1.6 mL, 0.8 mmol) and methanol (1 mL) were added and the solution was stirred 16 h at ambient temperature followed by 40° C. for 4 h. The solution was partitioned between water and ethyl acetate. The organic layer was washed with sodium bicarbonate (sat. aq.) and brine, dried over sodium sulfate and concentrated to 233 mg (quantitative yield) of the desired 5-(3,3-dmethyl-but-1-ynyl)-3-[(4-methyl-cyclohex-3-enecarbonyl)-(4-oxo-cyclohexyl)-amino]-thiophene-2-carboxylic acid methyl ester as a white foam.

5-(3,3-Dimethyl-but-1-ynyl)-3-[(4-methyl-cyclohex-3-enecarbonyl)-(4-oxo-cyclohexyl)-amino]-thiophene-2-carboxylic acid methyl ester (233 mg, 0.51 mmol) in THF (3 mL) and water (0.3 mL) was treated with sodium borohydride (19 mg, 0.48 mmol). After stirring for 20 min, water was added and the reaction mixture was extract twice with ethyl acetate. The combined organic layers were dried over sodium sulfate, filtered and concentrated. Flash chromatography (10% EtOAc:hexanes, 4 min, 10-70% EtOAc:hexanes, 12 min, 12 g column) afforded 130 mg (59% yield) of the desired methyl 5-(3,3-dimethylbut-1-ynyl)-3-((S)—N-((1r,4S)-4-hydroxycyclohexyl)-4-methylcyclohex-3-enecarboxamido)thiophene-2-carboxylate.

Example 27

Compound 27: 5-(3,3-dimethylbut-1-ynyl)-3-((S)-N-((1r,4S)-4-(dimethylphosphoryloxy)cyclohexyl)-4-methylcyclohex-3-enecarboxamido)thiophene-2-carboxylic acid

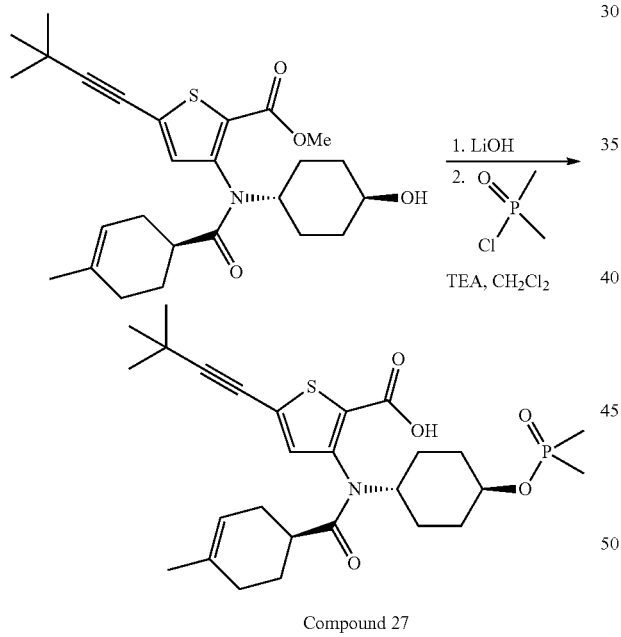

Compound 27

Compound 27 may be prepared by hydrolysis of methyl 5-(3,3-dimethylbut-1-ynyl)-3-((S)—N-((1r,4S)-4-hydroxycyclohexyl)-4-methylcyclohex-3-enecarboxamido)thiophene-2-carboxylate to the corresponding acid and conversion of that acid to Compound 27 in the same manner as for Compound 1.

ADDITIONAL PROPHETIC EXAMPLES

The following additional examples, including enantiomers thereof, may be made using analogous methods:

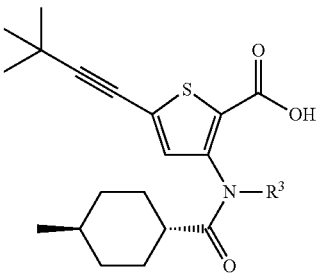

wherein $R^3$ is selected from a group in the table below.

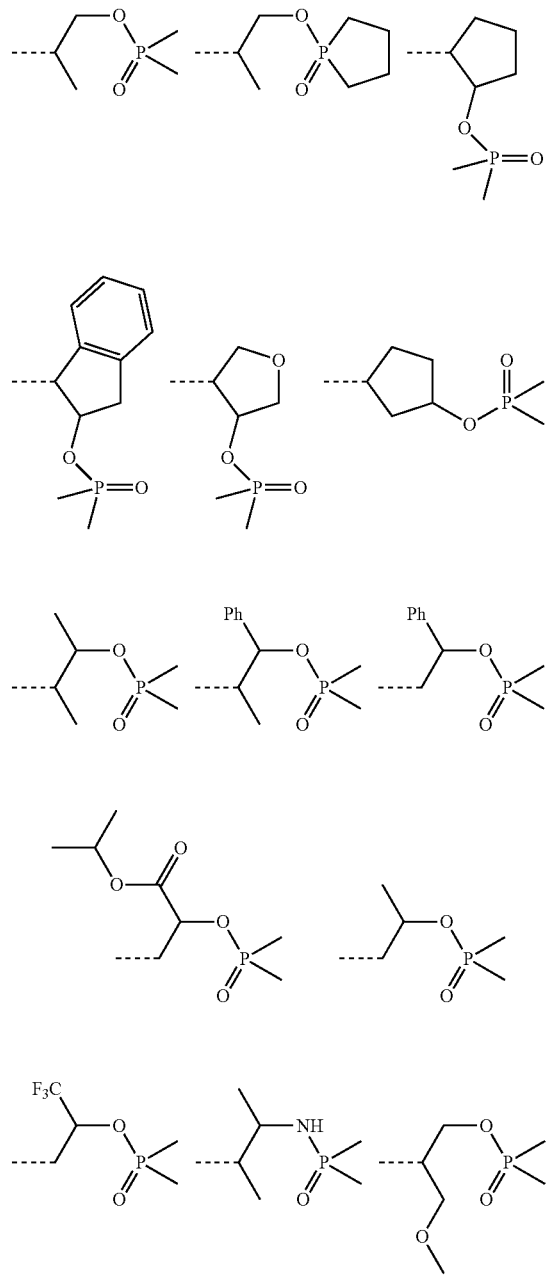

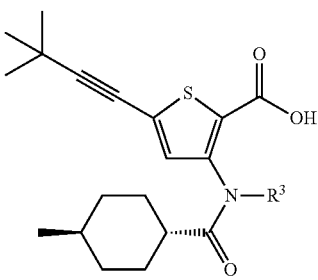

wherein R³ is selected from a group in the table below.

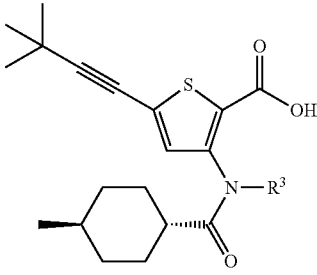

wherein R³ is selected from a group in the table below.

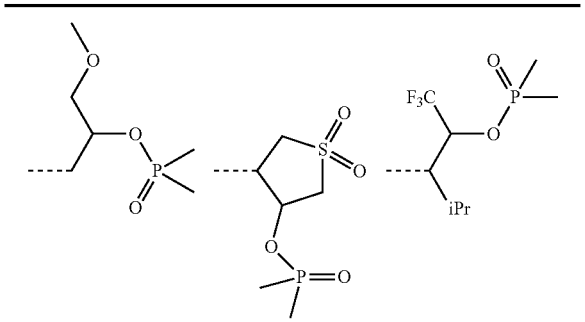

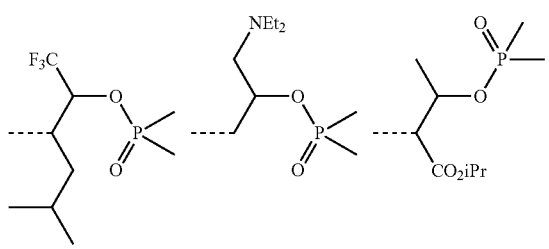

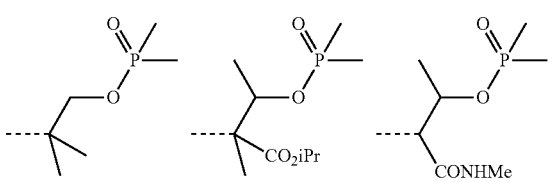

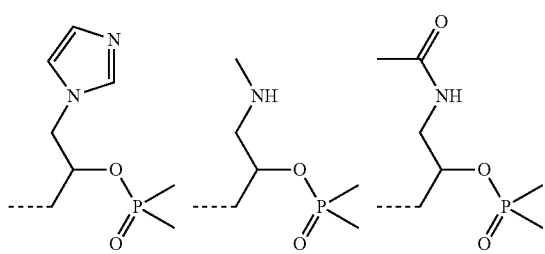

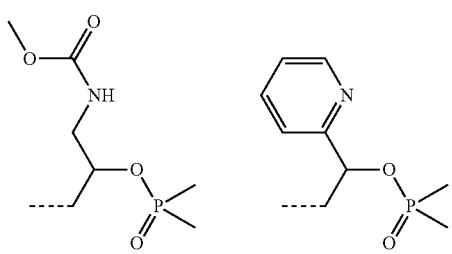

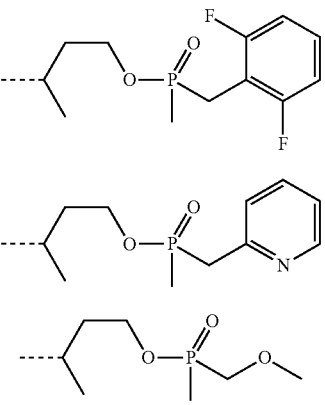

Similarly, analogous methods may be used to synthesize compounds having the following substitution pattern:

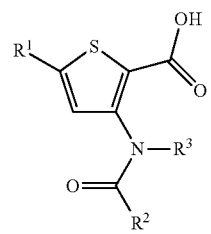

where R³ is selected from
—CH₂—P(O)R^I R^II,
—C(CH₃)₂—P(O)R^I R^II,
—CH(C₃₋₆ cycloalkyl)-P(O)R^I R^II,
—CH₂—CH₂—P(O)R^I R^II,
—C(CH₃)₂—CH₂—P(O)R^I R^II,
—CH(C₃₋₆cycloalkyl)-CH₂—P(O)R^I R^II, and
—CH(CH₂R⁺)—CH₂—P(O)R^I R^II, including both the (+) and (−) configurations about the chiral atom;

where each R^I is independently a variety of substituents, as herein described, including but not limited to $C_{1-12}$ alkyl, $C_{1-12}$ alkoxy, or —OH;

where each R^II is independently a variety of substituents, as herein described, including but not limited to $C_{1-12}$ alkyl, $C_{6-14}$ aryl, such as phenyl, or $C_{8-16}$ arylalkyl, such as benzyl; and where each R is independently a variety of substituents, as herein described, including but not limited to $C_{1-12}$ alkyl, or $C_{1-12}$ alkoxy.

General Schemes (for P in R¹)

As in the above general illustrations, the phosphorus-containing moiety may be introduced into R¹ with the rest of the molecule already assembled. Alternatively, the bond between the thiophene and R¹ may conveniently be formed by a variety of aryl-aryl or aryl-acetylene coupling methods such as those pioneered by Suzuki or Sonagashira (see Smith, M. B. and March, J. Advanced Organic Chemistry, 6$^{th}$ edition, Wiley-Interscience, pp 899 and 903 respectively, herein incorporated by reference with regard to such synthetic teaching), using a 5-halothiophene as illustrated in Scheme B.

Scheme B

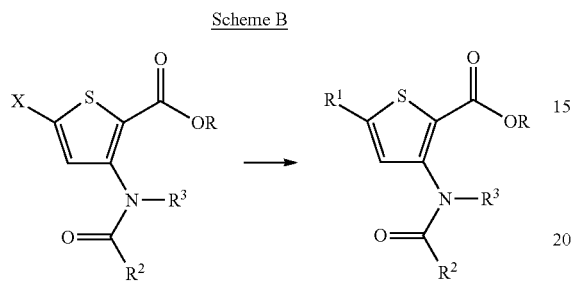

Experimentals

Example 20

Compound 20: 3-[(1,4-Dioxa-spiro[4.5]dec-8-yl)-(4-methyl-cyclohexanecarbonyl)-amino]-5-[4-(ethoxymethyl-phosphinoylmethyl)-phenyl]-thiophene-2-carboxylic acid Scheme 11

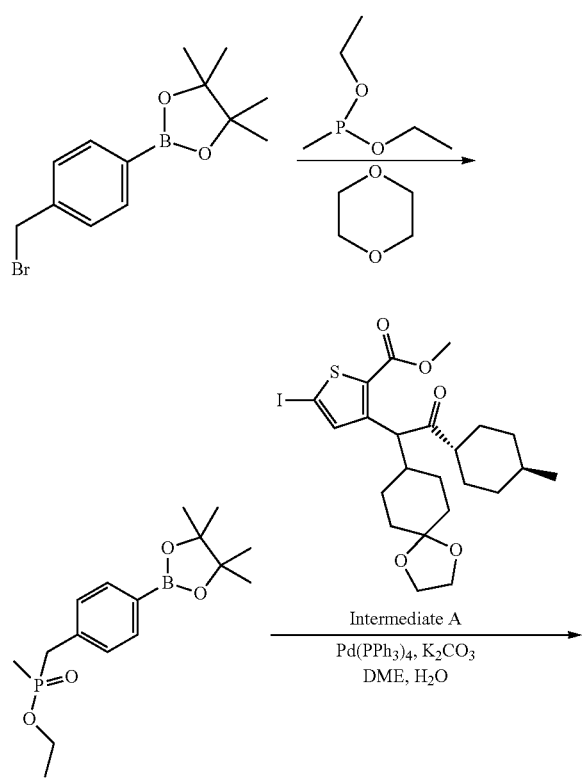

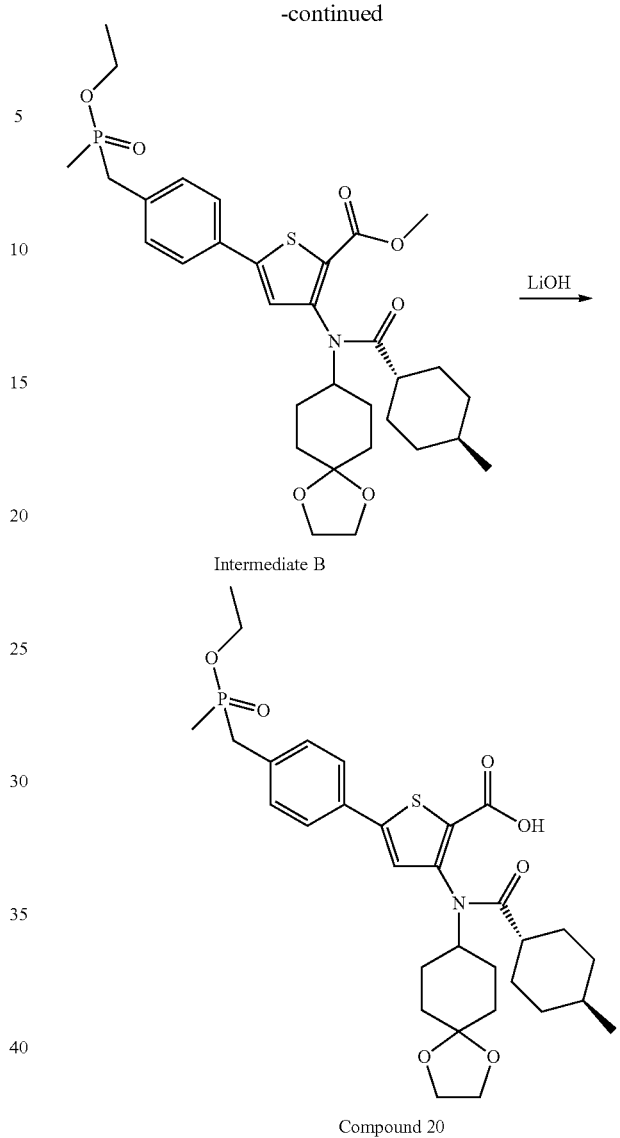

4-(Bromomethyl)benzeneboronic acid pinacol ester (609 mg, 2.05 mmol, 1 eq.) was weighed into a round-bottomed flask and purged with N$_2$. 1,4-Dioxane (6 mL) and diethoxymethylphosphine (0.96 mL, 6.15 mmol, 3 eq.) were then added, and the solution was stirred at 100° C. for 1 hour. The reaction was then concentrated to an oil from which the product (methyl-[4-(4,4,5,5-tetramethyl-[1,3,3]dioxaborolan-2-yl)-benzyl]-phosphinic acid ethyl ester) was isolated by column chromatography (SiO$_2$, 10% MeOH in dichloromethane) as a clear oil (657 mg, 2.028 mmol, 98%). This clear oil was then dissolved in dimethoxyethane (7 mL) and the resulting solution was added to a 20 mL microwave vial containing intermediate A (3-[(1,4-Dioxa-spiro[4.5]dec-8-yl)-(4-methyl-cyclohexanecarbonyl)-amino]-5-iodo-thiophene-2-carboxylic acid methyl ester; see WO 2008/58393 A1; 925 mg, 1.69 mmol, 1 eq.), Pd(PPh$_3$)$_4$ (98 mg, 0.0845 mmol, 0.05 eq.), and potassium carbonate (467 mg, 3.38 mmol, 2 eq.), and 3.5 mL water. The vial was sealed and heated by microwave to 120° C. for 10 minutes. The reaction was partitioned between ethyl acetate and water. The aqueous layer was washed twice with 50 mL ethyl acetate, and the ethyl acetate layers were combined, washed with brine, dried over magnesium sulfate, filtered, and concentrated to an oil from which intermediate B (3-[(1,4-Dioxa-spiro[4.5]dec-8-yl)-(4-methyl-cyclohexanecarbonyl)-amino]-5-[4-(ethoxy-methyl-phosphinoylmethyl)-phenyl]-thiophene-2-carboxylic acid methyl ester) was isolated by column chromatography (SiO$_2$, 9% methanol in ethyl acetate) as a tan solid (1.01 g, 1.65 mmole, 98%).

This material (55 mg, 0.089 mmol, 1 eq.) was dissolved in tetrahydrofuran (2 mL) at room temperature. A solution of lithium hydroxide monohydrate (8 mg, 0.2 mmole, 2.2 eq.) in 1 mL water and 5 drops of methanol was then added, and the solution was stirred at room temperature for 4 hours. The reaction was neutralized with 0.11 mL 2N HCl and concentrated. The crude material was redissolved in methanol and purified by reverse phase preparative HPLC to afford 3-[(1,4-Dioxa-spiro[4.5]dec-8-yl)-(4-methyl-cyclohexanecarbonyl)-amino]-5-[4-(ethoxy-methyl-phosphinoylmethyl)-phenyl]-thiophene-2-carboxylic acid (10 mg, 19%). MS (m/z) 604.3 [M+H]$^+$ HPLC retention time: 3.575 min (5-95% acetonitrile with 0.05% TFA: water with 0.05% TFA).

Example 21

Compound 21: 5-[4-(Ethoxy-methyl-phosphinoylmethyl)-phenyl]-3-[(4-hydroxy-cyclohexyl)-(4-methyl-cyclohexanecarbonyl)-amino]-thiophene-2-carboxylic acid Scheme 12

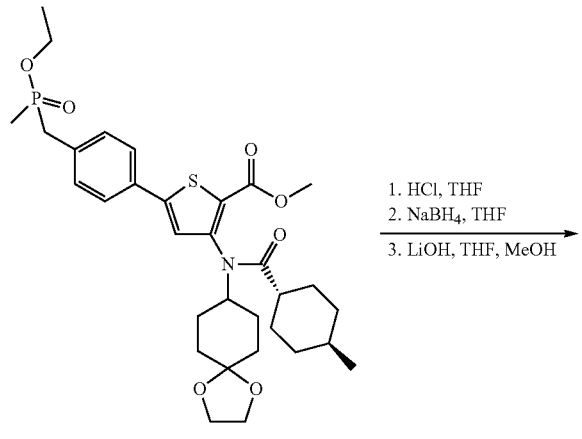

Intermediate B

Compound 21

3-[(1,4-Dioxa-spiro[4.5]dec-8-yl)-(4-methyl-cyclohexanecarbonyl)-amino]-5-[4-(ethoxy-methyl-phosphinoylmethyl)-phenyl]-thiophene-2-carboxylic acid methyl ester (204 mg, 0.331 mmol, 1 eq.) was weighed into a small flask and dissolved in 3 mL THF. Next, 2 mL of 3.6 N HCl was added and the reaction was stirred at 40° C. for 1.5 hours. The reaction was then cooled to room temperature and diluted with 40 mL water. The solution was then extracted twice with ethyl acetate. The combined ethyl acetate layers were then washed twice with saturated NaHCO$_3$, twice with water, and once with brine, dried over sodium sulfate, filtered and concentrated to afford the crude ketone (176 mg). This material (176 mg, ~0.307 mmol) was dissolved in 5 mL anhydrous THF and cooled to −25° C. using an acetonitrile/dry ice bath. Sodium borohydride (9 mg, 0.230 mmol, 0.75 eq.) was added as a solid in two portions. The reaction was stirred 1.5 hours at −25° C., then was quenched with 3 mL 2 N HCl and warmed to room temperature. The solution was then extracted twice with ethyl acetate. The combined ethyl acetate layers were washed once with brine, and then dried over sodium sulfate, filtered and concentrated. This crude product (173 mg) was dissolved in 2 mL THF. Stirring was begun and 0.5 mL methanol and a solution of lithium hydroxide monohydrate (25 mg, 0.6 mmol, 2 eq. in 0.5 mL water) were added. The reaction was stirred at 40° C. for 45 minutes whereupon the reaction was stopped by the addition of 0.35 mL 2 N HCl. The reaction was concentrated, then redissolved in methanol and purified by reverse phase preparative HPLC to afford 5-[4-(Ethoxy-methyl-phosphinoylmethyl)-phenyl]-3-[(4-hydroxy-cyclohexyl)-(4-methyl-cyclohexanecarbonyl)-amino]-thiophene-2-carboxylic acid (11 mg, 6%). MS (m/z) 562.1 [M+H]$^+$ HPLC retention time: 3.152 min (5-95% acetonitrile with 0.05% TFA: water with 0.05% TFA).

Example 22

Compound 22: 3-[(4-Hydroxy-cyclohexyl)-(4-methyl-cyclohexanecarbonyl)-amino]-5-[4-(hydroxymethyl-phosphinoylmethyl)-phenyl]-thiophene-2-carboxylic acid Scheme 13

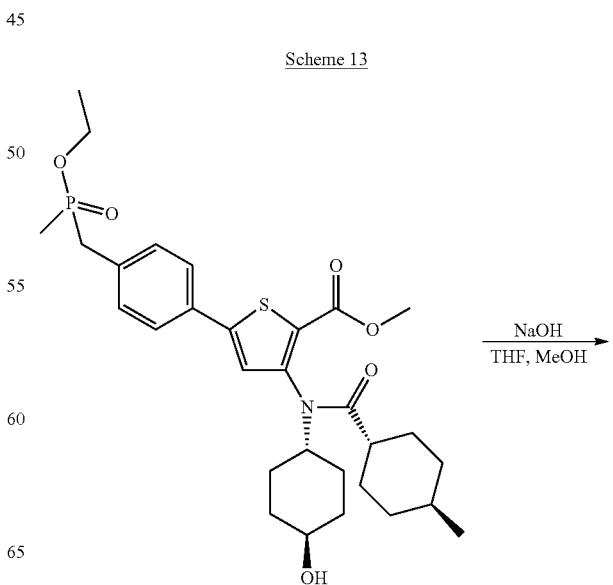

-continued

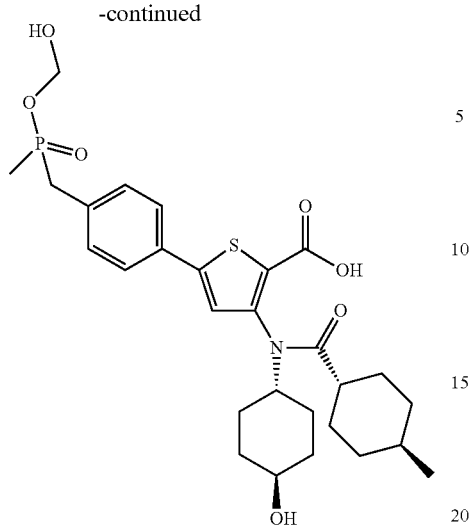

Compound 22

Following the reductive step in Example 21, the crude product (50 mg) was dissolved in 1 mL THF and 0.5 mL methanol. 10 N NaOH (0.26 mL, ~30 eq) was added, and the solution was stirred overnight at room temperature. The reaction was then neutralized with 1.3 mL 2 N HCl, concentrated, and purified by reverse phase preparative HPLC to afford (3-[(4-Hydroxy-cyclohexyl)-(4-methyl-cyclohexanecarbonyl)-amino]-5-[4-(hydroxy-methyl-phosphinoylmethyl)-phenyl]-thiophene-2-carboxylic acid (20 mg, 11%). MS (m/z) 534.2 [M+H]$^+$ HPLC retention time: 2.725 min (5-95% acetonitrile with 0.05% TFA: water with 0.05% TFA).

Example 23

Compound 23: 5-[3,3-Dimethyl-5-(tetrahydro-pyran-4-yloxy)-pent-1-ynyl]-3-[(4-(pyridin-2-yloxy)-cyclohexyl)-(4-methyl-cyclohexanecarbonyl)-amino]-thiophene-2-carboxylic acid Scheme 10

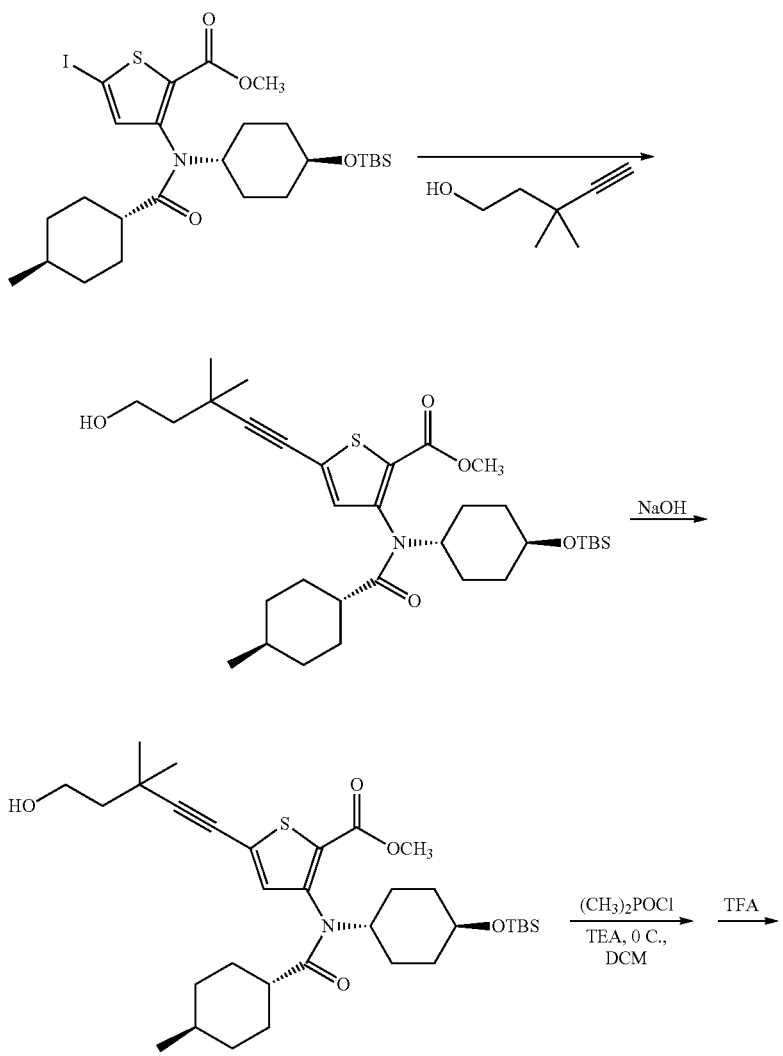

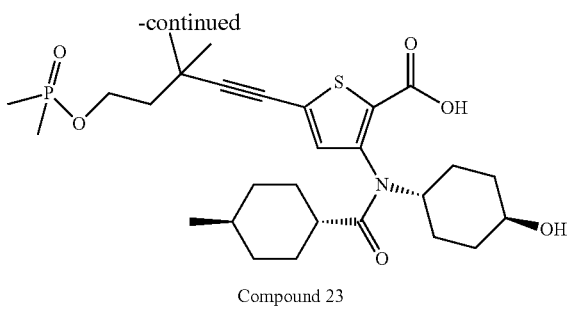

Compound 23

A solution of 3,3-dimethyl-pent-4-yn-1-ol (600 mg, 5.36 mmol), 3-[[4-(tert-Butyl-dimethyl-silanyloxy)-cyclohexyl]-(4-methyl-cyclohexanecarbonyl)-amino]-5-iodo-thiophene-2-carboxylic acid methyl ester (2767 mg, 4.46 mmol) and triethylamine (10.8 mL, 77.48 mmol) in DMF (25 mL) was degassed for 10 minutes with nitrogen. PdCl$_2$(PPh$_3$)$_2$ (314 mg, 0.45 mmol) and CuI (170 mg, 0.90 mmol) was added and the resulting mixture was degassed with nitrogen for an additional 5 minutes after which the reaction was placed in a 80° C. oil bath and heated for 3.5 h. The reaction was cooled and partitioned between ethyl acetate and sat. NaHCO$_3$. The organic layer was separated, washed with 5% LiCl, brine, dried over Na$_2$SO$_4$ and concentrated to give a dark brown foam. Purification by flash column chromatography on silica gel using 30% ethyl acetate in hexanes then 5% methanol in ethyl acetate provided 3-[[4-(tert-butyl-dimethyl-silanyloxy)-cyclohexyl]-(4-methyl-cyclohexanecarbonyl)-amino]-5-(5-hydroxy-3,3-dimethyl-pent-1-ynyl)-thiophene-2-carboxylic acid methyl ester (2.43 g, 90%) as a pale yellow foam.

After hydrolysis of the 3-[[4-(tert-butyl-dimethyl-silanyloxy)-cyclohexyl]-(4-methyl-cyclohexanecarbonyl)-amino]-5-(5-hydroxy-3,3-dimethyl-pent-1-ynyl)-thiophene-2-carboxylic acid methyl ester to the corresponding acid, Compound 23 was obtained by phosphorylated in the same manner as in Example 1.

MS=552; Hplc retention time is 3.319.

PROPHETIC EXAMPLES

The following additional examples, including enantiomers thereof, may be made using analogous methods:

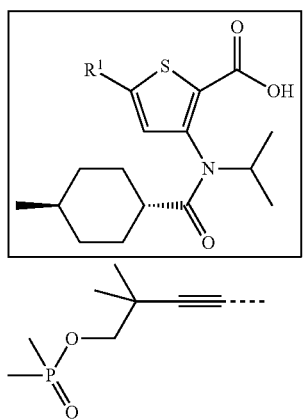

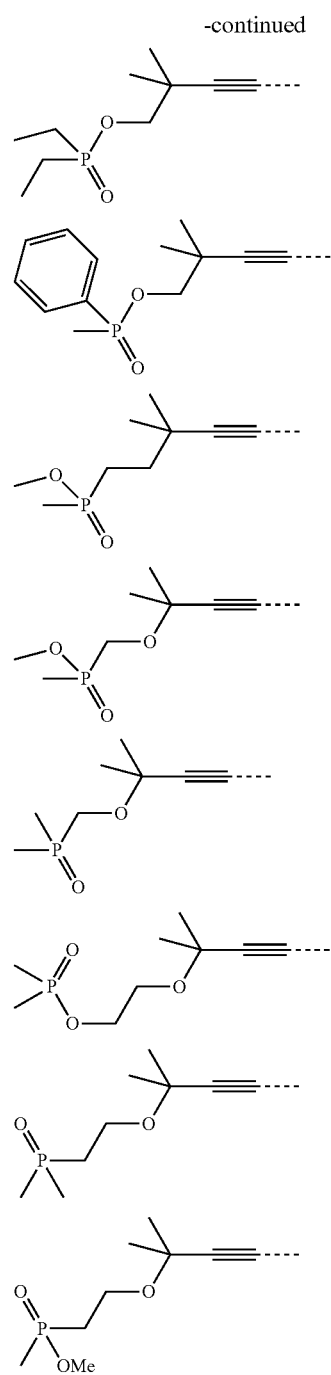

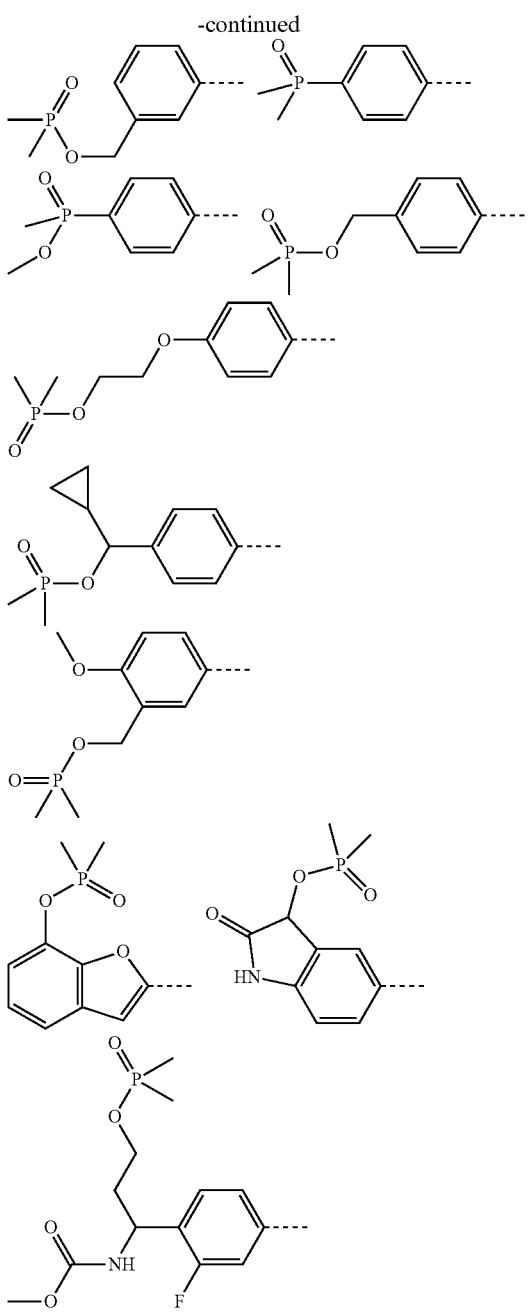

BIOLOGICAL EXAMPLES

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-based Flavivirus Immunodetection assay

BHK21 or A549 cells are trypsinized, counted and diluted to $2 \times 10^5$ cells/mL in Hams F-12 media (A549 cells) or RPMI-1640 media (BHK21 cells) supplemented with 2% fetal bovine serum (FBS) and 1% penicillin/streptomycin. $2 \times 10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5, 5'-tetramethylbenzidine (TMB) substrate solution (Sigma) is added to each well for two minutes. The reaction is stopped by addition of 0.5 M sulfuric acid. The plates are read at 450 nm abosorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4 \times 10^5$ cells/mL in RPMI-1640 media supplemented with 2% FBS and 1% penicillin/streptomycin. For testing against dengue virus, Huh7 cells are trypsinized and diluted to a concentration of $4 \times 10^5$ cells/mL in DMEM media supplemented with 5% FBS and 1% penicillin/streptomycin. A 50 microliter of cell suspension ($2 \times 10^4$ cells) is dispensed per well in a 96-well optical bottom PIT polymer-based plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Lumnescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul at al. J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq):1N NaOH (pH adjusted to 3.5): 100 mM citrate buffer pH 3.5 (0.9% v/v:2.5% v/v: 96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul at al. Cytokines are also analysed as described by Schul. NS1 protein levels are analysed using a Platelia™ kit (BioRad Laboratories). An antiviral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 uL added to the pre-specified wells in column 3 or 13 of a polypropylene 384-well plate. The rest of the 384-well plate was filled with 10 uL 100% DMSO except for columns 23 and 24, where 10 uL of 500 uM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 μL of cell media containing 1600 suspended Huh-7 HCV replicon cells was added with a Biotek uFlow Workstation. A volume of 0.4 μL of the compound solution was transferred from the serial dilution plate to the cell culture plate on a Biomek FX Workstation. The DMSO concentration in the final assay condition was 0.44%. The plates were incubated for 3 days at 37° C. with 5% CO2 and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 μL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 μL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 μL of a solution containing 1:100 mixture of Dual-Glo Stop & Glo substrate(Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[(EC_{50}/[I])^b + 1]$$

Where b is Hill's coefficient. See, for reference, Hill, A. V., *The Possible Effects of the Aggregation of the Molecules of Haemoglobin on its Dissociation Curves*, J. Physiol. 40: iv-vii. (1910).

% inhibition values at a specific concentration, for example 2 µM, can also be derived from the formula above.

When tested, certain compounds of this invention were found to inhibit viral replication as listed in Table 1:

TABLE 1

| Compound No. | % inhibition at 2 µM |
|---|---|
| 1 | 99.8 |
| 2 | 99.8 |
| 3 | 99.6 |
| 4 | 94.7 |
| 5 | 100.0 |
| 6 | 93.2 |
| 7 | 99.8 |
| 8 | 99.8 |
| 9 | 99.9 |
| 10 | 100.0 |
| 11 | 99.8 |
| 12 | 98.2 |
| 13 | 99.8 |
| 14 | 99.8 |
| 15 | 98.9 |
| 16 | 99.5 |
| 17 | 99.5 |
| 18 | 98.8 |
| 19 | 94.2 |
| 20 | 56.3 |
| 21 | 79.2 |
| 22 | 12.3 |

Preferred compounds of the invention have an $EC_{50}$ of 500 nM or less. Non-limiting examples of preferred compounds are compounds 1, 2, 3, 5, 7, 8, 9, 10, 11, 13, 14, 15, 16, 17, 18, 19, 23 and 24.

The specific pharmacological and biochemical responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of Formula I:

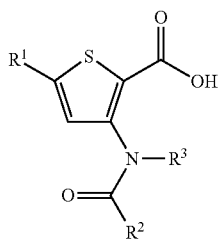

(I)

or a pharmaceutically acceptable salt or ester thereof, wherein:

$R^1$ is $-(L^1)_m-(L^2)_n-X^1$;

$L^1$ is selected from the group consisting of alkynylene and optionally substituted arylene;

m is 1;

when $L^1$ is substituted, $L^1$ is substituted with one or more $Q^6$;

$L^2$ is selected from the group consisting of —NHC(O)— and optionally substituted alkylene;

n is 0 or 1;

when $L^2$ is substituted, $L^2$ is substituted with one or more $Q^6$;

$X^1$ is selected from the group consisting of
a) —P(O)$R^xR^y$,
b) —P(O)O$R^xR^y$,
c) —OP(O)$R^xR^y$ and
d) optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

each of $R^x$ and $R^y$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^x$ and $R^y$ taken together with the atoms to which they are attached form a 3 to 10 membered heterocyclyl;

when either $R^x$ or $R^y$ is substituted, $R^x$ or $R^y$ is substituted with one or more $Q^6$;

when $X^1$ is selected from d) and is substituted, $X^1$ is substituted with one or more $Q^1$;

each $Q^1$ individually is selected from the group consisting of halogen, oxo, oxide, —NO$_2$, —SR$^{11}$, —S(O)R$^{10}$, —S(O)$_2$R$^{10}$, —S(O)$_2$NR$^{12}$R$^{11}$, —NR$^{12}$C(O)R$^{11}$, —NR$^{12}$C(O)NR$^{11}$R$^{12}$, —NR$^{11}$S(O)R$^{10}$, —NR$^{11}$S(O)$_2$R$^{10}$, —NR$^{12}$S(O)$_2$NR$^{11}$R$^{12}$, —CR$^{12}$(=NNR$^{11}$R$^{12}$), —CR$^{12}$(=NOR$^{11}$), —ONR$^{12}$R$^{11}$, —ON(=CR$^{12}$R$^{11}$), —NR$^{12}$OR$^{11}$, —OH, —NR$^{11}$R$^{12}$, —C(O)OR$^{12}$, —CN, —N$_3$, —C(=NR$^{13}$)NR$^{11}$R$^{12}$, —NR$^{12}$C(=NR$^{13}$)NR$^{11}$R$^{12}$, —NR$^{12}$C(O)OR$^{11}$, —OC(O)NR$^{11}$R$^{12}$, —OP(O)R$^{11}$R$^{12}$, —P(O)R$^{11}$R$^{12}$, —P(O)OR$^{11}$R$^{12}$, —C(O)NR$^{11}$R$^{12}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl and optionally substituted-3-10 membered heterocyclyl;

wherein each $R^{10}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{11}$ and $R^{12}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{11}$ and $R^{12}$ taken together with the atoms to which they are attached form a 4 to 10 membered heterocyclyl;

or $R^{10}$ and $R^{11}$ taken together with the atoms to which they are attached form a 4 to 10 membered heterocyclyl;

each $R^{13}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{14}$, —CHO and —S(O)$_2R^{14}$;

where each $R^{14}$ individually is optionally substituted $C_{1-12}$ alkyl;

when $Q^1$ is substituted, $Q^1$ is substituted with one or more $Q^6$;

$R^2$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein, when $R^2$ is substituted, $R^2$ is substituted with one or more $Q^2$;

where each $Q^2$ individually is selected from the group consisting of halogen, oxo, oxide, —NO$_2$, —SR$^{21}$, —S(O)R$^{20}$, —S(O)$_2$R$^{20}$, —S(O)$_2$NR$^{22}$R$^{21}$, —NR$^{22}$C(O)R$^{21}$, —NR$^{22}$C(O)NR$^{21}$R$^{22}$, —NR$^{21}$S(O)R$^{20}$, —NR$^{21}$S(O)$_2$R$^{20}$, —NR$^{22}$S(O)$_2$NR$^{21}$R$^{22}$, —CR$^{22}$(=NNR$^{21}$R$^{22}$), —CR$^{22}$(=NOR$^{21}$), —ONR$^{22}$R$^{21}$, —ON(=CR$^{22}$R$^{21}$), —NR$^{22}$OR$^{21}$, —OH, —NR$^{21}$R$^{22}$, —C(O)OR$^{22}$, —CN, —N$_3$, —C(=NR$^{23}$)NR$^{21}$R$^{22}$, —NR$^{22}$C(=NR$^{23}$)NR$^{21}$R$^{22}$, —NR$^{22}$C(O)OR$^{21}$, —OC(O)NR$^{21}$R$^{22}$, —OP(O)R$^{21}$R$^{22}$, —P(O)R$^{21}$R$^{22}$, P(O)OR$^{21}$R$^{22}$, —C(O)NR$^{21}$R$^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl and optionally substituted 3-10 membered heterocyclyl;

wherein each $R^{20}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{21}$ and $R^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{21}$ and $R^{22}$ taken together with the atoms to which they are attached form a 4 to 10 membered heterocyclyl;

or $R^{20}$ and $R^{21}$ taken together with the atoms to which they are attached form a 4 to 10 membered heterocyclyl;

each $R^{23}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{24}$, CHO and —S(O)$_2R^{24}$;

where each $R^{24}$ individually is optionally substituted $C_{1-12}$ alkyl;

when $Q^2$ is substituted, $Q^2$ is substituted with one or more $Q^6$;

$R^3$ is -(L$^3$)$_p$-(L$^4$)$_q$-(X$^3$);

L$^3$ is selected from the group consisting of optionally substituted $C_{1-12}$ alkylene, optionally substituted $C_{2-12}$ alkenylene, optionally substituted $C_{2-12}$ alkynylene, optionally substituted $C_{3-12}$ cycloalkylene, optionally substituted $C_{1-12}$ haloalkylene, optionally substituted $C_{6-14}$ arylene, optionally substituted 3-12 membered heterocyclylene, optionally substituted 3-18 membered heteroarylalkylene and optionally substituted $C_{6-18}$ arylalkylene;

p is 0 or 1;

when L$^3$ is substituted, L$^3$ is substituted with one or more $Q^3$;

each $Q^3$ individually is selected from the group consisting of halogen, oxo, oxide, —NO$_2$, —SR$^{31}$, —S(O)R$^{30}$, —S(O)$_2$R$^{30}$, —S(O)$_2$NR$^{32}$R$^{31}$, —NR$^{32}$C(O)R$^{31}$, —NR$^{32}$C(O)NR$^{31}$R$^{32}$, —NR$^{31}$S(O)R$^{30}$, —NR$^{31}$S(O)$_2$R$^{30}$, —NR$^{32}$S(O)$_2$NR$^{31}$R$^{32}$, —CR$^{32}$(=NNR$^{31}$R$^{32}$), —CR$^{32}$(=NOR$^{31}$), —ONR$^{32}$R$^{31}$, —ON(=CR$^{32}$R$^{31}$), —NR$^{32}$OR$^{31}$, —OH, —NR$^{31}$R$^{32}$, —C(O)OR$^{32}$, —CN, —N$_3$, —C(=NR$^{33}$)NR$^{31}$R$^{32}$, —NR$^{30}$C(=NR$^{33}$)NR$^{31}$R$^{32}$, —NR$^{30}$C(O)OR$^{31}$, —OC(O)NR$^{31}$R$^{32}$, —OP(O)R$^{31}$R$^{32}$, —P(O)R$^{31}$R$^{32}$, —P(O)OR$^{31}$R$^{32}$—C(O)NR$^{31}$R$^{32}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl and optionally substituted 3-10 membered heterocyclyl;

wherein each $R^{30}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{31}$ and $R^{32}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or $R^{31}$ and $R^{32}$ taken together with the atoms to which they are attached form a 4 to 10 membered heterocyclyl;

or $R^{30}$ and $R^{31}$ taken together with the atoms to which they are attached form a 4 to 10 membered heterocyclyl;

each $R^{33}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{34}$, CHO and —S(O)$_2R^{34}$;

where each $R^{34}$ individually is optionally substituted $C_{1-12}$ alkyl;

when $Q^3$ is substituted, $Q^3$ is substituted with one or more $Q^6$;

$L^4$ is selected from the group consisting of —NH—, and optionally substituted $C_{1-12}$ alkylene;

q is 0, 1 or 2;

when $L^4$ is substituted, $L^4$ is substituted with one or more $Q^6$;

$X^3$ is selected from the group consisting of:
e) —P(O)$R^xR^y$,
f) —P(O)O$R^xR^y$,
g) —OP(O)$R^xR^y$,
h) —P(O)(O$R^x$)(O$R^y$),
i)

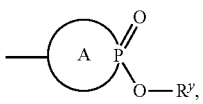

wherein each A is a 4 to 6 membered ring, including the depicted P atom, j)

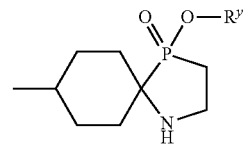

and k) optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

each of $R^x$ and $R^y$ individually is as defined above;

when $X^3$ is selected from k) and is substituted, $X^3$ is substituted with one or more $Q^4$;

each $Q^4$ individually is selected from the group consisting of halogen, oxo, oxide, —NO$_2$, —S$R^{41}$, —S(O)$R^{40}$, —S(O)$_2R^{40}$, —S(O)$_2$N$R^{42}R^{41}$, —N$R^{42}$C(O)$R^{41}$, —N$R^{42}$C(O)N$R^{41}R^{42}$, —N$R^{41}$S(O)$R^{40}$, —N$R^{41}$S(O)$_2R^{40}$, —N$R^{42}$S(O)$_2$N$R^{41}R^{42}$, —C$R^{42}$(=NN$R^{41}R^{42}$), —C$R^{42}$(=NO$R^{41}$), —ON$R^{42}R^{41}$, —ON(=C$R^{42}R^{41}$), —N$R^{42}$O$R^{41}$, —OH, —N$R^{41}R^{42}$, —C(O)O$R^{42}$, —CN, —N$_3$, —C(=N$R^{43}$)N$R^{41}R^{42}$, —N$R^{42}$C(=N$R^{43}$)N$R^{41}R^{42}$, —N$R^{42}$C(O)O$R^{41}$, and —OC(O)N$R^{41}R^{42}$, —OP(O)$R^{41}R^{42}$, —P(O)$R^{41}R^{42}$, —P(O)O$R^{41}R^{42}$, —C(O)N$R^{41}R^{42}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl and optionally substituted-3-10 membered heterocyclyl;

wherein each $R^{40}$, independently, is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

wherein each $R^{41}$ and $R^{42}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl and optionally substituted $C_{6-18}$ arylalkyl;

or R$^{41}$ and R$^{42}$ taken together with the atoms to which they are attached form a 4 to 10 membered heterocyclyl;
or R$^{40}$ and R$^{41}$ taken together with the atoms to which they are attached form a 4 to 10 membered heterocyclyl;
each R$^{43}$ independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{44}$, CHO and —S(O)$_2$R$^{44}$;
where each R$^{44}$ individually is optionally substituted C$_{1-12}$ alkyl;
when Q$^4$ is substituted, Q$^4$ is substituted with one or more Q$^6$; and
each Q$^6$ individually is selected from the group consisting of halogen, oxo, oxide, —NO$_2$, —N(=O), —SR$^{61}$, —S(O)R$^{60}$, —S(O)$_2$R$^{60}$, —S(O)$_2$NR$^{62}$R$^{61}$, —NR$^{62}$C(O)R$^{61}$, —NR$^{62}$C(O)NR$^{61}$R$^{62}$, —NR$^{61}$S(O)R$^{60}$, —NR$^{61}$S(O)$_2$R$^{60}$, —NR$^{62}$S(O)$_2$NR$^{61}$R$^{62}$, —CR$^{62}$(=NNR$^{61}$R$^{62}$), —CR$^{62}$(=NOR$^{61}$), —ONR$^{62}$R$^{61}$, —ON(=CR$^{62}$R$^{61}$), —NR$^{62}$OR$^{61}$, —OH, —NR$^{61}$R$^{62}$, —C(O)OR$^{62}$, —CN, —N$_3$, —C(=NR$^{63}$)NR$^{61}$R$^{62}$, —NR$^{62}$C(=NR$^{63}$)NR$^{61}$R$^{62}$, —NR$^{62}$C(O)OR$^{61}$, —OC(O)NR$^{61}$R$^{62}$, —OP(O)R$^{61}$R$^{62}$, —P(O)R$^{61}$R$^{62}$, —P(O)OR$^{61}$R$^{62}$, —P(O)(OR$^{61}$)OR$^{62}$, —C(O)NR$^{61}$R$^{62}$, C$_{1-6}$ alkyl, C$_{2-6}$ alkenyl, C$_{2-6}$ alkynyl, C$_{3-6}$ cycloalkyl, C$_{6-12}$ arylalkyl, C$_{6-12}$ aryl, 3-14 membered heteroaryl, C$_{1-6}$ alkyloxy, C$_{2-6}$ alkenyloxy, C$_{2-6}$ alkynyloxy, C$_{3-6}$ cycloalkyloxy, C$_{6-12}$ aryloxy, 3-14 membered heteroaryloxy, 4-12 membered heterocyclyloxy, —C(O)C$_{1-6}$ alkyl, —C(O)C$_{2-6}$ alkenyl, —C(O)C$_{2-6}$ alkynyl, —C(O)C$_{3-6}$ cycloalkyl, —C(O)C$_{1-6}$ haloalkyl, —C(O)C$_{6-12}$ aryl, —C(O)-3-14 membered heteroaryl, —C(O)C$_{6-12}$ arylalkyl and 3-10 membered heterocyclyl;
wherein each R$^{60}$, independently, is selected from the group consisting of C$_{1-12}$ alkyl, C$_{2-12}$ alkenyl, C$_{2-12}$ alkynyl, C$_{3-12}$ cycloalkyl, C$_{1-12}$ haloalkyl, C$_{6-14}$ aryl, 3-14 membered heteroaryl, 3-12 membered heterocyclyl, 3-18 membered heteroarylalkyl and C$_{6-18}$ arylalkyl;
wherein each R$^{61}$ and R$^{62}$, independently, is selected from the group consisting of H, C$_{1-12}$ alkyl, C$_{2-12}$ alkenyl, C$_{2-12}$ alkynyl, C$_{3-12}$ cycloalkyl, C$_{1-12}$ haloalkyl, C$_{6-14}$ aryl, 3-14 membered heteroaryl, 3-12 membered heterocyclyl, 3-18 membered heteroarylalkyl and C$_{6-18}$ arylalkyl;
or R$^{61}$ and R$^{62}$ taken together with the atoms to which they are attached form a 4 to 10 membered heterocyclyl;
or R$^{60}$ and R$^{61}$ taken together with the atoms to which they are attached form a 4 to 10 membered heterocyclyl;
each R$^{63}$ independently is selected from the group consisting of H, C$_{1-12}$ alkyl, C$_{2-12}$ alkenyl, C$_{2-12}$ alkynyl, C$_{3-12}$ cycloalkyl, C$_{6-14}$ aryl, 3-14 membered heteroaryl, 3-12 membered heterocyclyl, 3-18 membered heteroarylalkyl, C$_{6-18}$ arylalkyl, —CN, —C(O)R$^{64}$, —CHO and —S(O)$_2$R$^{64}$;
where each R$^{64}$ individually is C$_{1-12}$ alkyl;
provided, however, that when X$^1$ is selected from d), then X$^3$ is selected from the group consisting of e), f), g), h), i) and j).

2. The compound of claim 1, wherein L$^1$ is phenylene.

3. The compound of claim 1, wherein L$^1$ is —C≡C—;

n is 0; and
X$^1$ is optionally substituted C$_{1-12}$ alkyl.

4. The compound of claim 1, wherein the compound of Formula I is represented by a compound of Formula II:

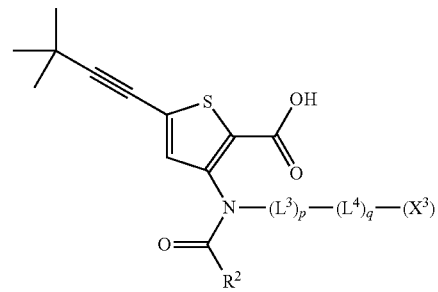

Formula II or a pharmaceutically acceptable salt or ester thereof.

5. The compound of claim 1, wherein R$^2$ is optionally substituted C$_{3-12}$ cycloalkyl.

6. The compound of claim 5, wherein R$^2$ is optionally substituted cyclohexyl.

7. The compound of claim 1, wherein R$^2$ is selected from the group consisting of:

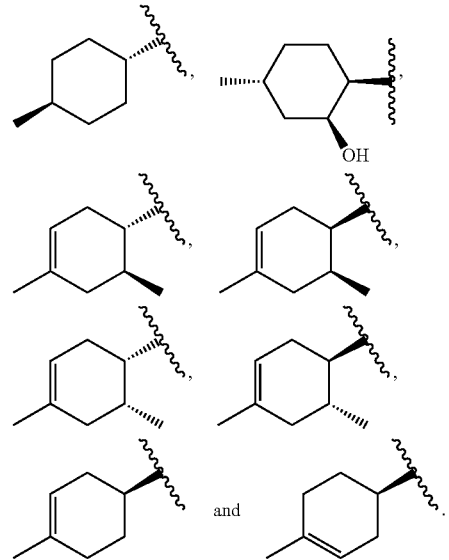

8. The compound of claim 7, wherein R$^2$ is

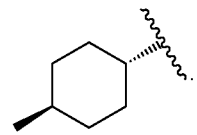

9. The compound of claim 1, wherein p is 1.

10. The compound of claim 1, wherein p is 0.

11. The compound of claim 1, wherein L$^3$ is optionally substituted C$_{3-12}$ cycloalkylene.

12. The compound of claim 11, wherein L$^3$ is optionally substituted cyclohexylene.

13. The compound of claim 1, where L³ is an optionally substituted 5-6 membered N-containing heterocyclene.

14. The compound of claim 1, wherein L³ is optionally substituted C₁₋₁₂ alkylene.

15. The compound of claim 1, wherein q is 0.

16. The compound of claim 1, wherein q is 1.

17. The compound of claim 1, wherein q is 2.

18. The compound of claim 1, wherein X³ is

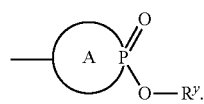

19. The compound of claim 1, wherein X³ is —P(O)RˣRʸ.

20. The compound of claim 1, wherein X³ is —P(O)ORˣRʸ.

21. The compound of claim 1, wherein X³ is —OP(O)RˣRʸ.

22. The compound of claim 1, wherein X³ is —P(O)(ORˣ)(ORʸ).

23. The compound of claim 1 selected from the group consisting of

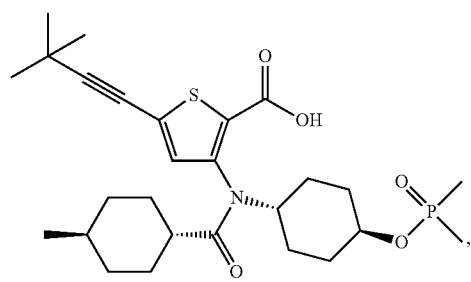

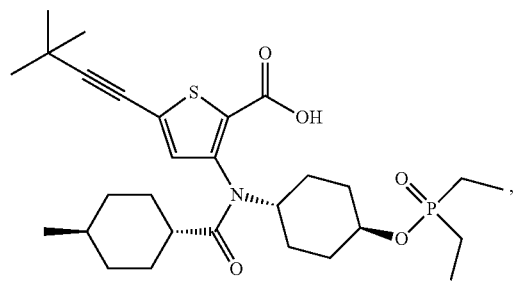

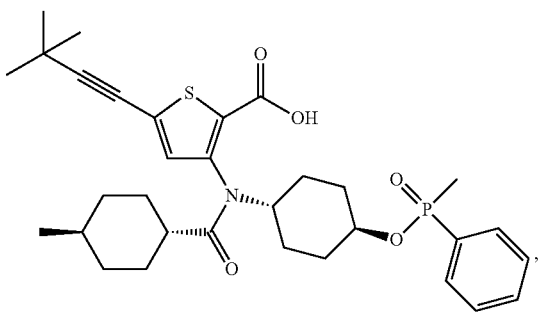

-continued

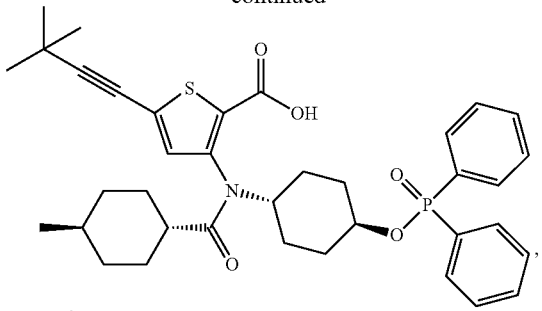

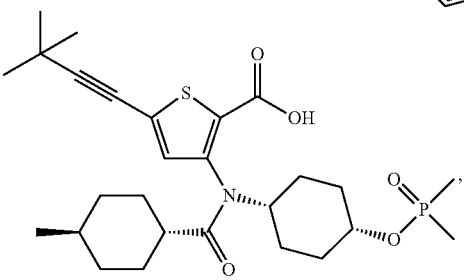

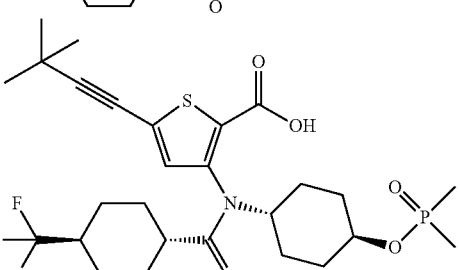

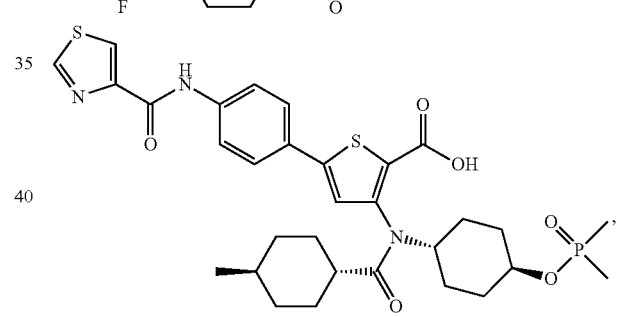

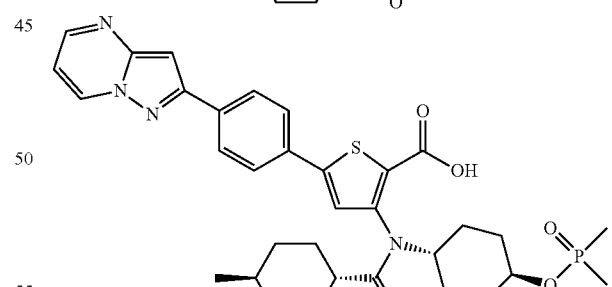

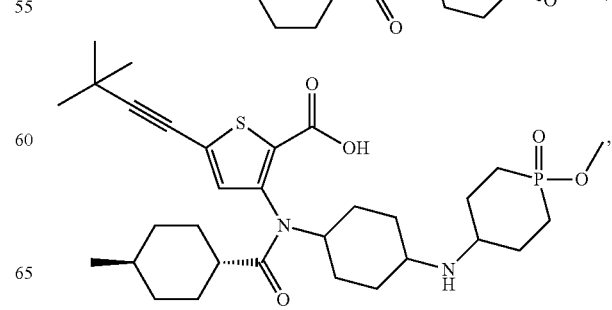

115
-continued
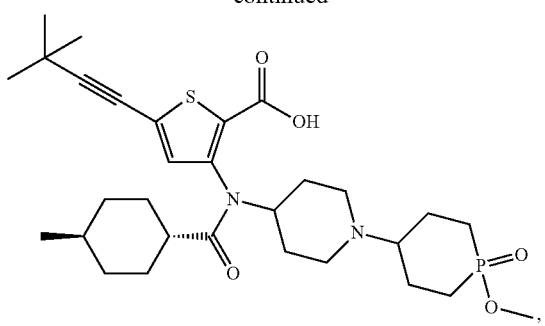
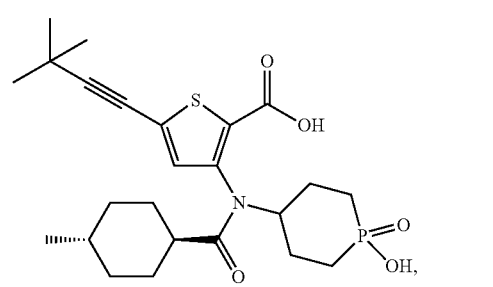
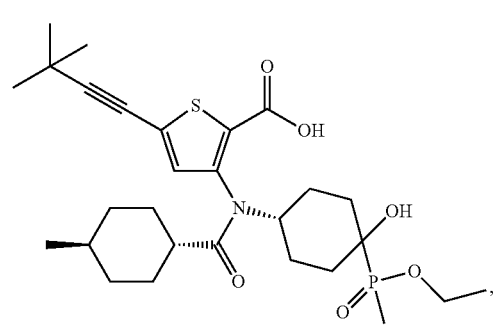
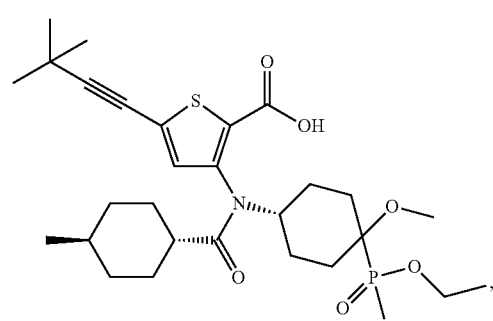
116
-continued
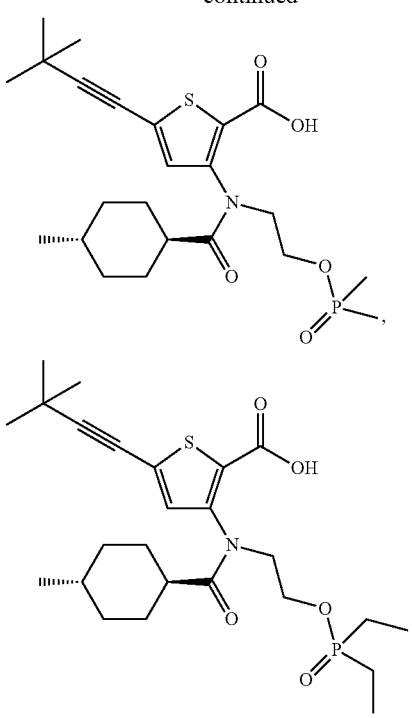
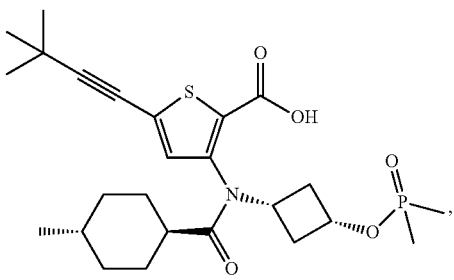
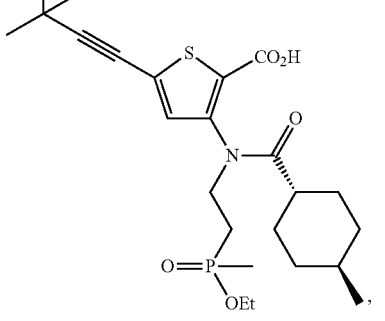
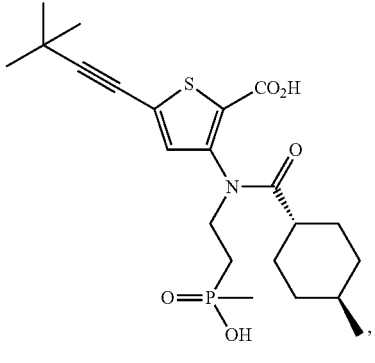

117
-continued

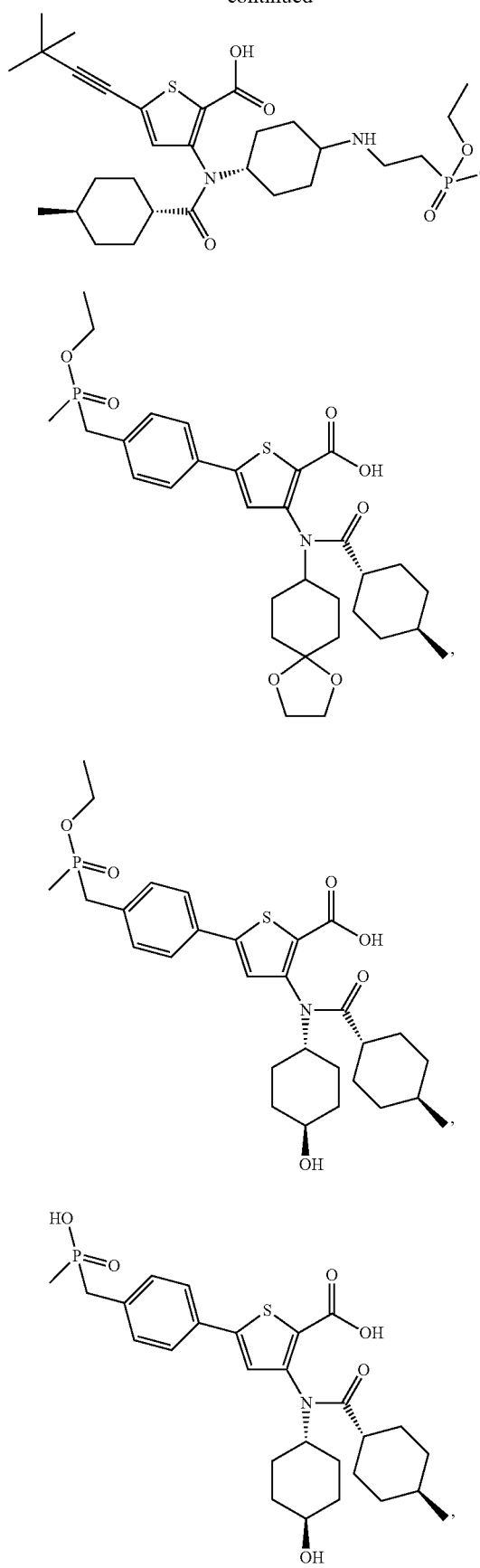

118
-continued

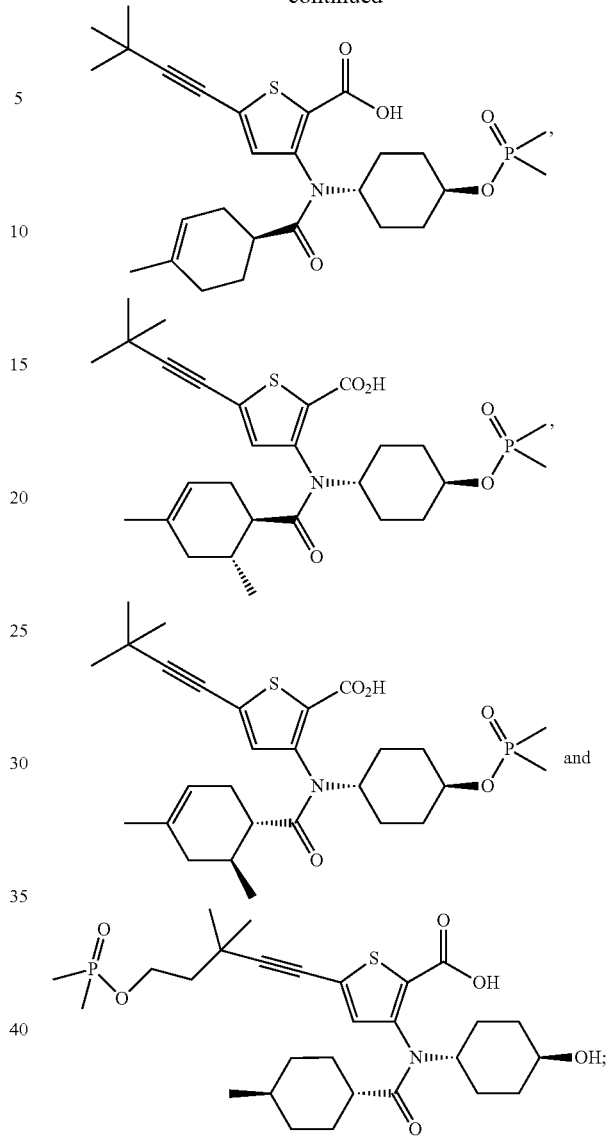

or a pharmaceutically acceptable salt or ester thereof.

24. A pharmaceutical composition comprising a therapeutically effective amount of a compound of claim 1 and a pharmaceutically acceptable carrier or excipient.

25. The pharmaceutical composition of claim 24 further comprising at least one therapeutic agent selected from the group consisting of an interferon, ribavirin or an analog thereof, an HCV NS3 protease inhibitor, an NS5a inhibitor, an alpha-glucosidase 1 inhibitor, a hepatoprotectant, a mevalonate decarboxylase antagonist, an antagonist of the renin-angiotensin system, an endothelin antagonist, other anti-fibrotic agents, a nucleoside or nucleotide inhibitor of HCV NS5B polymerase, a non-nucleoside inhibitor of HCV NS5B polymerase, an HCV NS5A inhibitor, a TLR-7 agonist, a cyclophillin inhibitor, an HCV IRES inhibitor, a pharmacokinetic enhancer and other drugs for treating HCV; or a mixture thereof.

26. A method for treating a Flaviviridae viral infection comprising administering a therapeutically effective amount of a compound of claim 1 to a mammal in need thereof.

27. The method of claim 26 wherein the viral infection is caused by a Hepatitis C virus.

28. The method of claim 27 further comprising administering at least one therapeutic agent selected from the group consisting of an interferon, ribavirin or an analog thereof, an HCV NS3 protease inhibitor, an NS5a inhibitor, an alpha-glucosidase 1 inhibitor, a hepatoprotectant, a mevalonate decarboxylase antagonist, an antagonist of the renin-angiotensin system, an endothelin antagonist, other anti-fibrotic agent, a nucleoside or nucleotide inhibitor of HCV NS5B polymerase, a non-nucleoside inhibitor of HCV NS5B polymerase, an HCV NS5A inhibitor, a TLR-7 agonist, a cyclophillin inhibitor, an HCV IRES inhibitor, a pharmacokinetic enhancer and other drugs for treating HCV; or a mixture thereof.

* * * * *

UNITED STATES PATENT AND TRADEMARK OFFICE
CERTIFICATE OF CORRECTION

PATENT NO. : 8,501,714 B2
APPLICATION NO. : 13/392467
DATED : August 6, 2013
INVENTOR(S) : Cho et al.

It is certified that error appears in the above-identified patent and that said Letters Patent is hereby corrected as shown below:

In the specification

In column 76, lines 8-11, please delete "5-(3,3-Dimethyl-but-1-ynyl)-3-[[2-(methoxy-methyl-phosphinoyl)-ethyl]-(4-methyl-cyclohexanecarbonyl)-amino]-thiophene-2-carboxy-lic acid" and insert -- 5-(3,3-Dimethyl-but-1-ynyl)-3-[[2-(ethoxy-methyl-phosphinoyl)-ethyl]-(4-methyl-cyclohexanecarbonyl)-amino]-thiophene-2-carboxy-lic acid --

In column 97, lines 1-20, please delete the compound below:

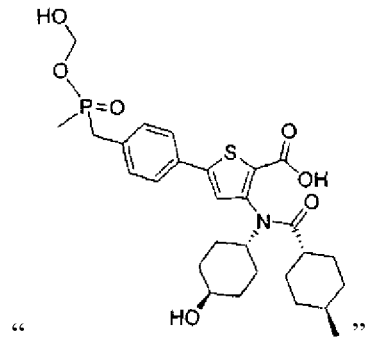

and replace it with the following compound:

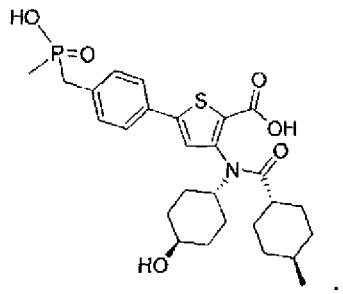

Signed and Sealed this
Twenty-seventh Day of May, 2014

Michelle K. Lee
*Deputy Director of the United States Patent and Trademark Office*